United States Patent
Peng et al.

(10) Patent No.: US 12,390,472 B2
(45) Date of Patent: Aug. 19, 2025

(54) POLYSUBSTITUTED BENZENE COMPOUND AND PREPARATION METHOD AND USE THEREOF

(71) Applicant: SUZHOU SINOVENT PHARMACEUTICALS CO., LTD., Suzhou (CN)

(72) Inventors: Wei Peng, Suzhou (CN); Jun Xian, Southborough, MA (US); Yonghan Hu, Suzhou (CN); Yuchuan Wu, Beijing (CN); Xi Chen, Beijing (CN); Shaoqiang Huang, Beijing (CN); Xiao Liu, Beijing (CN); Xin Li, Suzhou (CN); Bin Huang, Suzhou (CN); Dongdong Wu, Suzhou (CN)

(73) Assignee: EVOPOINT BIOSCIENCES CO., LTD., Suzhou (CN)

( * ) Notice: Subject to any disclaimer, the term of this patent is extended or adjusted under 35 U.S.C. 154(b) by 811 days.

(21) Appl. No.: 17/263,038

(22) PCT Filed: Jul. 26, 2019

(86) PCT No.: PCT/CN2019/098019
§ 371 (c)(1),
(2) Date: Jan. 25, 2021

(87) PCT Pub. No.: WO2020/020374
PCT Pub. Date: Jan. 30, 2020

(65) Prior Publication Data
US 2021/0308141 A1  Oct. 7, 2021

(30) Foreign Application Priority Data
Jul. 27, 2018 (WO) ................ PCT/CN2018/097635

(51) Int. Cl.
| | | |
|---|---|---|
| *A61K 31/5377* | (2006.01) |
| *A61K 31/4433* | (2006.01) |
| *A61K 31/4545* | (2006.01) |
| *A61K 31/4709* | (2006.01) |
| *A61K 31/496* | (2006.01) |
| *A61K 31/5386* | (2006.01) |
| *A61P 35/00* | (2006.01) |
| *C07D 213/64* | (2006.01) |
| *C07D 401/12* | (2006.01) |
| *C07D 405/12* | (2006.01) |
| *C07D 405/14* | (2006.01) |
| *C07D 413/12* | (2006.01) |
| *C07D 413/14* | (2006.01) |
| *C07D 493/08* | (2006.01) |
| *C07D 498/08* | (2006.01) |

(52) U.S. Cl.
CPC ...... *A61K 31/5377* (2013.01); *A61K 31/4433* (2013.01); *A61K 31/4545* (2013.01); *A61K 31/4709* (2013.01); *A61K 31/496* (2013.01); *A61K 31/5386* (2013.01); *A61P 35/00* (2018.01); *C07D 213/64* (2013.01); *C07D 401/12* (2013.01); *C07D 405/12* (2013.01); *C07D 405/14* (2013.01); *C07D 413/12* (2013.01); *C07D 413/14* (2013.01); *C07D 493/08* (2013.01); *C07D 498/08* (2013.01)

(58) Field of Classification Search
CPC C07D 213/64; A61K 31/5386; A61K 31/496; A61K 31/4433; A61K 31/5377
See application file for complete search history.

(56) References Cited

U.S. PATENT DOCUMENTS

2016/0332969 A1* 11/2016 Kuntz ................ C07D 407/12

FOREIGN PATENT DOCUMENTS

| CN | 102970869 A | 3/2013 |
|---|---|---|
| CN | 104080769 A | 10/2014 |
| CN | 105452246 A | 3/2016 |
| CN | 107573336 A | 1/2018 |
| CN | 108314677 A | 7/2018 |

(Continued)

OTHER PUBLICATIONS

Extended European Search Report for Application No. EP 19840459.2, dated Feb. 21, 2022.

(Continued)

*Primary Examiner* — Marcos L Sznaidman
(74) *Attorney, Agent, or Firm* — MARSHALL, GERSTEIN & BORUN LLP

(57) ABSTRACT

The present invention provides a novel EZH2 inhibitor compound represented by formula (I) and a use of the inhibitor compound in preventing or treating a disease mediated by EZH2.

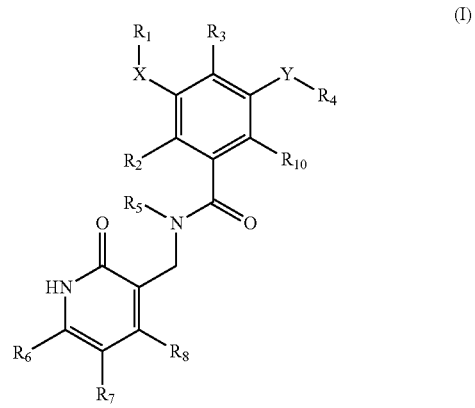

8 Claims, 2 Drawing Sheets

(56) References Cited

FOREIGN PATENT DOCUMENTS

| | | |
|---|---|---|
| EP | 3121175 | 1/2017 |
| JP | 2014513084 A | 5/2014 |
| JP | 2014516931 A | 7/2014 |
| JP | 2015511603 A | 4/2015 |
| KR | 2014-0147836 A | 12/2014 |
| WO | WO-2010090723 A2 | 8/2010 |
| WO | WO-2011140324 A1 | 11/2011 |
| WO | WO-2011140325 A1 | 11/2011 |
| WO | WO-2012051492 A2 | 4/2012 |
| WO | WO-2012118812 A2 | 9/2012 |
| WO | WO-2012142513 A1 | 10/2012 |
| WO | WO-2013075083 A1 | 5/2013 |
| WO | WO-2013173441 A2 | 11/2013 |
| WO | WO-2014049488 A1 | 4/2014 |
| WO | WO-2017025493 A1 | 2/2017 |
| WO | WO-2015200650 A9 | 4/2017 |

OTHER PUBLICATIONS

Verma, S.K. et al., "Identification of Potent, Selective, Cell-Active Inhibitors of the Histone Lysine Methyltransferase EZH2", ACS Medicinal Chemistry Letters, vol. 3, No. 12, pp. 1091-1096 (2012).

Office Action, corresponding Japanese patent application No. 2021-504181, dated Jul. 7, 2023.

International Search Report and Written Opinion for Application No. PCT/CN2019/098019, dated Nov. 5, 2019.

Kevin W. Kuntz, et al., "The Importance of Being Me: Magic Methyls, Methyltransferase Inhibitors, and the Discovery of Tazemetostat", Journal of Medicinal Chemistry, vol. 59, No. 4, pp. 1556-1564 (2019).

Ryan D. Morin et al., "Somatic mutation of EZH2 (Y641) in /Follicular and Diffuse Large B-cell Lymphomas of Germinal Center Origin," Nat Genet., vol. 42, pp. 181-185 (2010).

Ingeborg M. Bachmann et al., "EZH2 Expression Is Associated With High Proliferation Rate and Aggressive Tumor Subgroups in Cutaneous Melanoma and Cancers of the Endometrium, Prostate, and Breast", Journal of Clinical Oncology, vol. 24, No. 2, pp. 268-273 (2006).

Salman A. Aljubran et al., "Enhancer of Zeste Homolog 2 Induces Pulmonary Artery Smooth Muscle Cell Proliferation", PLoS ONE, vol. 7, Issue 5, e37712 (2012).

Giovanni Barosi, "Emerging targeted therapies in myelofibrosis", Expert Review of Hematology, vol. 5, No. 3, pp. 313-324 (2012).

Shan He et al., "Inhibition of histone methylation arrests ongoing graft-versus-host disease in mice by selectively inducing apoptosis of alloreactive effector T cells", Blood, vol. 119, No. 5, pp. 1274-1282 (2012).

William T. Gibson et al., "Mutations in EZH2 Cause Weaver Syndrome", The American Journal of Human Genetics, 90, pp. 110-118 (2012).

Peng Zhang et al., "Abnormal histone modifications in PBMCs from patients with psoriasis vulgaris", European Journal of Dermatology, vol. 21, No. 4, pp. 552-557 (2011).

Office Action, Korean patent application No. 10-2021-7005272, dated Jul. 12, 2024.

\* cited by examiner

POLYSUBSTITUTED BENZENE COMPOUND AND PREPARATION METHOD AND USE THEREOF

TECHNICAL FIELD

The present invention relates to a novel EZH2 inhibitor compound and use of the inhibitor compound in preventing or treating EZH2-mediated diseases.

BACKGROUND

Histone methyltransferases (HMTs) are a family of enzymes that control selective methylation at specific amino acid sites of the histone. Covalent modifications of the histone, such as methylation, can alter the chromatin structure of the DNA of eukaryotic cells, resulting in heritable variations in gene expression. These modifications are referred to as epigenetic modifications. Aberrant expression and/or over-activation of enzymes responsible for histone modifications will lead to the development of diseases, such as cancer. Therefore, the treatment of diseases such as cancer can be influenced by selectively inhibiting the activity of the corresponding enzyme.

Histone-lysine N-methyltransferase EZH2, a catalytic subunit of polycomb repressive complex 2 (PRC2), methylates the lysine at site 27 of specific histone H3 (H3K27), and is essential for self-renewal of cancer stem cells. EZH2 is able to silence several anti-metastasis genes, favoring cell invasion and uncontrolled cell growth. For example, a somatic mutation in tyrosine at site 641 of EZH2 has been reported to be associated with follicular lymphoma and diffuse B-cell lymphoma (Nature Genet., 2010, 42, 2, 181-185).

Elevated levels of trimethylated H3K27 due to increased expression of EZH2 contribute to the invasion and metastasis of cancer (e.g., melanoma, prostate cancer, breast cancer, and endometrial cancer) and thus the decreased survival time and increased mortality of patients (Bachmann et al, Journal of Clinical Oncology, 2006, 24, 4, 268-273). Increased expression of EZH2 also induces pulmonary artery smooth muscle proliferation (PLoS ONE, 2012, 7, 5, e37712). Increased expression of EZH2 has also been reported to be associated with myelofibrosis (Expert Review of Hematology, 2012, 5, 3, 313-324), HIV (WO2012051492A2), graft versus host disease (Blood, 2012, 119, 5, 1274-1282), Weaver syndrome (American Journal of Human Genetics, 2012, 90, 1, 110-118), psoriasis (European Journal of Dermatology, 2011, 21, 4, 552-557), and hepatic fibrosis (WO2010090723A2).

WO2011140324A1 discloses an indole compound as an EZH2 inhibitor and use for treating cancer thereof. WO2012118812A2 discloses a bicyclic heterocyclic compound as an EZH2 inhibitor and use for treating cancer thereof. WO2012142513A1 discloses a substituted benzene compound as an EZH2 inhibitor and use for treating cancer thereof.

It can be seen that inhibition of EZH2 activity can effectively reduce cell proliferation and invasion, and thus provides a treatment for EZH2-mediated diseases.

The research and development of new drugs is a rapidly developing field, and the discovery of drug candidates is accelerated by the technical progress. For these drug candidates, not only the evaluation of pharmacodynamics thereof but also the drug metabolism and kinetic properties are very important new drug screening indexes. An ideal drug needs to have a long duration of drug action and good bioavailability. A large number of drug candidates are eliminated each year because of poor pharmacokinetic parameters and metabolic characteristics. Therefore, the metabolic characteristics and pharmacokinetic parameters are important evaluation indexes for determining whether the candidate drug can be a patent medicine, and good pharmacokinetic parameters and metabolic characteristics are essential for lead compounds with development prospects. Therefore, EZH2 inhibitors with good pharmacokinetic characteristics provided would likely be more effective in vivo for pharmacodynamic effects.

The present invention aims to provide a novel EZH2 inhibitor and use of the inhibitor for treating EZH2-mediated diseases, such as cancer.

SUMMARY

According to one aspect of the present invention, a compound of formula (I) capable of inhibiting the activity of EZH2:

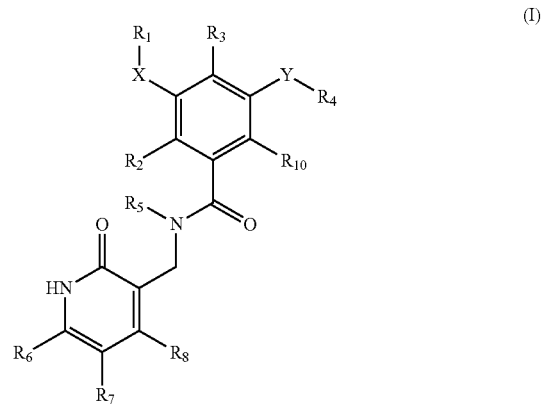

(I)

or a stereoisomer, a tautomer or a pharmaceutically acceptable salt thereof is provided, wherein, X and Y are each independently selected from a covalent bond, —$CH_2$—, —C(=O)—, —O—, —S—, —S(O)—, —S(O)$_2$—, and —$NR_9$—, wherein the $R_9$ is selected from H, $C_1$-$C_6$ alkyl, and $C_1$-$C_6$ haloalkyl;

$R_1$ is selected from $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$, $R_3$, and $R_{10}$ are each independently selected from H, hydroxy, $C_1$-$C_6$ alkyl, $C_2$-$C_6$ alkenyl, $C_2$-$C_6$ alkynyl, $C_1$-$C_6$ alkoxy, halogen, and —CN;

$R_4$ is $C_3$-$C_6$ cycloalkyl; wherein the $C_3$-$C_6$ cycloalkyl is optionally substituted with -Q-T, wherein the Q is selected from a covalent bond, —$CH_2$—, —C(=O)—, —O—, —S—, —S—(O)—, —S(O)$_2$—, and —$NR_9$'—, wherein the $R_9$' is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and $C_1$-$C_6$ alkyl; and $R_6$, $R_7$, and $R_8$ are each independently selected from H, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—, wherein the $C_1$-$C_6$ alkyl, the $C_2$-$C_6$ alkenyl, the $C_2$-$C_6$ alkynyl, the $C_1$-$C_6$ alkoxy, the $C_1$-$C_6$ alkyl-S—, the $C_1$-$C_6$ alkyl-NH—, the ($C_1$-$C_6$ alkyl)$_2$N—, the $C_1$-$C_6$ alkyl-C(=O)—, the $C_1$-$C_6$ alkyl-S(O)—, the $C_1$-$C_6$ alkyl-S(O)$_2$—, the $C_1$-$C_6$ alkyl-OC(=O)—, and the $C_1$-$C_6$ alkyl-OS(O)$_2$ are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

According to another aspect of the present invention, a method for preparing a compound of formula (I) disclosed herein or a stereoisomer, a tautomer and a pharmaceutically acceptable salt thereof is provided.

According to yet another aspect of the present invention, a pharmaceutical composition comprising a compound of formula (I) disclosed herein or a stereoisomer, a tautomer and a pharmaceutically acceptable salt thereof is provided.

According to yet another aspect of the present invention, use of a compound of formula (I) disclosed herein in preventing or treating EZH2-mediated diseases is provided.

According to yet another aspect of the present invention, a method for preventing or treating EZH2-mediated diseases is provided, which comprises administering to an individual in need a therapeutically effective amount of a compound of formula (I) disclosed herein or a stereoisomer, a tautomer thereof and a pharmaceutically acceptable salt thereof.

According to yet another aspect of the present invention, use of a compound of formula (I) disclosed herein or a stereoisomer, a tautomer and a pharmaceutically acceptable salt thereof in combination with at least one additional active therapeutic agent for treating EZH2-mediated diseases is provided.

DETAILED DESCRIPTION

Figure 1A:
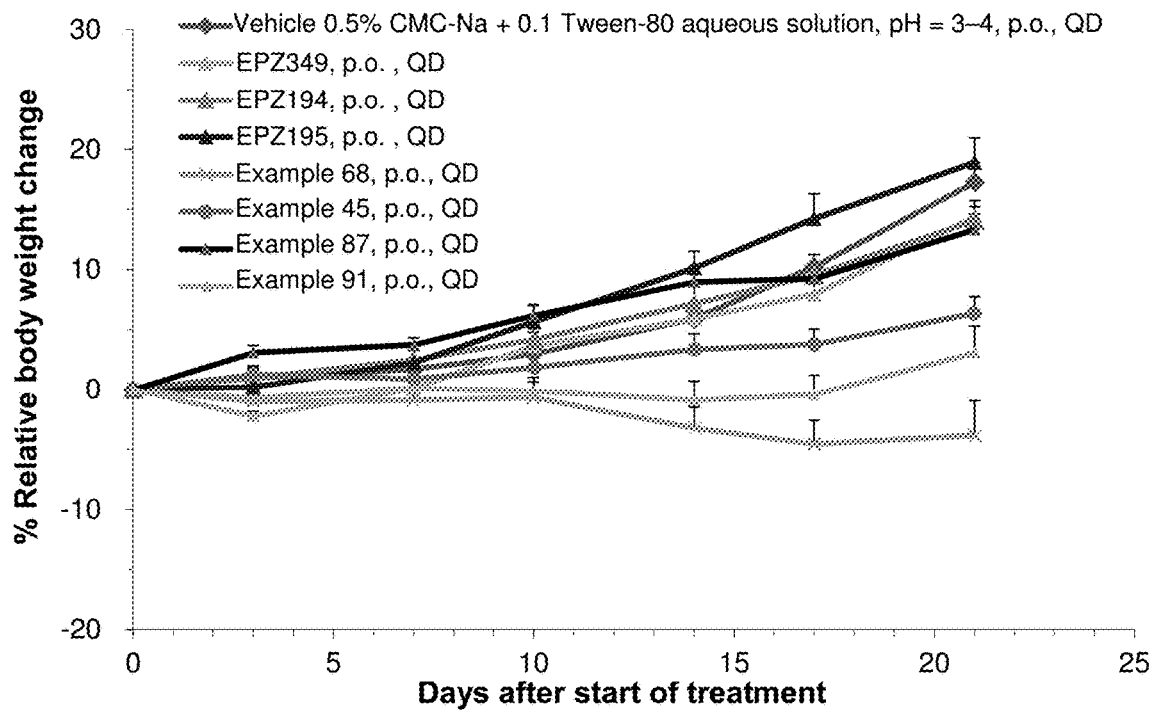
FIGS. 1A and 1B show the relative body weight change curves of mice bearing subcutaneous xenograft tumors of human B lymphocyte Pfeiffer after administering a compound of the present invention.

As used herein, the term "alkyl" refers to a linear or branched saturated hydrocarbyl having 1-12 carbon atoms. Preferably, the alkyl has 1-6 carbon atoms. More preferably, the alkyl has 1-4 carbon atoms. Examples of alkyl include, but are not limited to, methyl, ethyl, 1-propyl(n-propyl), 2-propyl(isopropyl), 1-butyl(n-butyl), 2-methyl-1-propyl (isobutyl), 2-butyl(sec-butyl), 2-methyl-2-propyl(tert-butyl), 1-pentyl(n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, 1-nonyl, 1-decyl, and the like.

As used herein, the term "alkenyl" refers to a linear or branched hydrocarbyl having 2-12 carbon atoms and having at least one carbon-carbon double bond. Preferably, the alkenyl has 2-6 carbon atoms. More preferably, the alkenyl has 2-4 carbon atoms. Examples of alkenyl include, but are not limited to, ethenyl, propenyl, allyl, 1-butenyl, 2-butenyl, 2-methylpropenyl, 1-pentenyl, 1-hexenyl, and the like.

As used herein, the term "alkynyl" refers to a linear or branched hydrocarbyl having 2-12 carbon atoms and having at least one carbon-carbon triple bond. Preferably, the alkynyl has 2-6 carbon atoms. More preferably, the alkynyl has 2-4 carbon atoms. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

As used herein, the term "aryl" refers to a group of a monocyclic or polycyclic (e.g., bicyclic or tricyclic) carbocyclic aromatic system having 6-14 ring carbon atoms ("$C_{6-14}$ aryl"). In some embodiments, the aryl has 6 ring carbon atoms ("$C_6$ aryl"; e.g., phenyl). In some embodiments, the aryl has 10 ring carbon atoms ("$C_{10}$ aryl"; e.g., naphthyl such as 1-naphthyl and 2-naphthyl). In some embodiments, the aryl has 14 ring carbon atoms ("$C_{14}$ aryl"; e.g., anthryl). "Aryl" also includes ring systems in which an aryl ring, as defined above, is fused to one or more carbocyclyl or heterocyclyl groups, where the group or attachment site is on the aryl ring, and in such cases the number of carbon atoms are still indicative of the number of carbon atoms in the aryl ring system. One or more fused carbocyclyl or heterocyclyl groups may be saturated or partially unsaturated 4-7 or 5-7 membered carbocyclyl or heterocyclyl groups optionally containing 1, 2, or 3 heteroatoms independently selected from nitrogen, oxygen, phosphorus, sulfur, silicon, and boron to form, for example, a 3,4-methylenedioxyphenyl group. As used herein, the term "halogen" refers to fluorine, chlorine, bromine, and iodine.

As used herein, the term "alkoxy" refers to an alkyl-O— group.

As used herein, the term "haloalkyl" includes alkyl groups substituted with one or more halogens (e.g., F, Cl, Br, or I). Representative examples of haloalkyl include, but are not limited to, trifluoromethyl, 2,2,2-trifluoroethyl, 2,2,2-trifluoro-1-(trifluoromethyl)ethyl, and the like.

As used herein, the term "cycloalkyl" refers to a saturated monovalent hydrocarbyl having one or more $C_3$-$C_{12}$ monocyclic rings (e.g., monocyclic, fused, bridged, and spiro rings). Examples of cycloalkyl include, but are not limited to, cyclopropyl, cyclobutyl, cyclopentyl, cyclohexyl, bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, norbornyl, norbornenyl, 6,6-dimethylbicyclo[3.1.1]heptyl, tricyclobutyl, adamantyl, and the like.

As used herein, the term "heteroaryl" refers to an aryl ring system containing one or more heteroatoms selected from N, O, and S, wherein the ring nitrogen and sulfur atoms are optionally oxidized, and the nitrogen atoms are optionally quaternized. Heteroaryl may be monocyclic or polycyclic, such as a monocyclic heteroaryl fused to one or more carbocyclic aromatic groups or other monocyclic heteroaryl. Examples include, but are not limited to, 5-6 membered heteroaryl containing 1-4 nitrogen atoms, such as pyrrolyl, imidazolyl, pyrazolyl, 2-pyridinyl, 3-pyridinyl, 4-pyridinyl, pyrimidinyl, pyrazinyl, pyridazinyl, and triazolyl (e.g., 4H-1,2,4-triazolyl, 1H-1,2,3-triazolyl, and 2H-1,2,3-triazolyl); 5-6 membered heteroaryl containing oxygen atoms, such as pyranyl, 2-furanyl, and 3-furanyl; 5-6 membered heteroaryl containing sulfur atoms, such as 2-thienyl and 3-thienyl; 5-6 membered heteroaryl containing 1-2 oxygen atoms and 1-3 nitrogen atoms, such as oxazolyl, isoxazolyl, oxadiazolyl (e.g., 1,2,4-oxadiazolyl, 1,3,4-oxadiazolyl, and 1,2,5-oxadiazolyl); and 5-6 membered heteroaryl containing 1-2 sulfur atoms and 1-3 nitrogen atoms, such as thiazolyl and thiadiazolyl (e.g., 1,2,4-thiadiazolyl, 1,3,4-thiadiazolyl, and 1,2,5-thiadiazolyl).

As used herein, the term "heterocyclyl" refers to a cyclic group that is fully saturated or may contain one or more unsaturated units (the unsaturation does not result in an aromatic ring system) and have 3-12 ring atoms in which 1-4 ring atoms are each independently a heteroatom such as nitrogen (aza), oxygen (oxa), or sulfur (thia), including but not limited to, fused, bridged, or spiro rings. According to the above definition, the heterocyclyl may simultaneously contain one or more heteroatoms, for example, the nitrogen-containing heterocyclyl may simultaneously contain oxygen and/or sulfur heteroatoms. Examples of heterocyclyl include: aziridinyl, azetidinyl, pyrrolidinyl, piperidinyl, morpholinyl, piperazinyl, homopiperazinyl, tetrahydrofuranyl, dioxanyl, indolinyl, isoindolinyl, morpholinyl, piperazinyl, piperidinyl, pyrrolidinyl, quinuclidinyl, thiomorpholinyl, tetrahydropyranyl, tetrahydrofuranyl, tetrahydroindolyl, thiomorpholinyl, azaboronyl, quinuclidinyl, isoquinuclidinyl, tropanyl, oxabicyclo[3.2.1]octyl, azabicyclo[3.2.1]octyl, oxabicyclo[2.2.1]heptyl, azabicyclo[2.2.1]heptyl, oxabicyclo[3.2.1]octyl, azabicyclo[3.2.1]octyl, oxabicyclo[3.2.2]nonyl, azabicyclo[3.2.2]nonyl, oxabicyclo[3.3.0]nonyl, azabicyclo[3.3.0]nonyl, oxabicyclo[3.3.1]nonyl, azabicyclo[3.3.1]nonyl, oxazabicyclo[3.1.1]heptyl, oxazabicyclo[3.2.1]octyl, and the like.

As used herein, the term "optionally substituted" means that a given structure or group is not substituted, or that a given structure or group is substituted with one or more specific substituents. Unless otherwise stated, optional substitution may occur at any position of the substituted group.

As used herein, "⁓" denotes the attachment site of the substituent.

As used herein, the term "stereoisomer" refers to a compound having same chemical composition and connectivity but different orientations of atoms in space, wherein the orientations cannot be rotationally interchanged through a single bond. The "stereoisomer" includes a "diastereoisomer" and an "enantiomer". The "diastereoisomer" refers to a stereoisomer having two or more chiral centers and whose molecules are not mirror images of each other. Diastereoisomers have different physical properties, such as melting points, boiling points, spectral properties, and reactivity. Mixtures of diastereoisomers can be separated in high resolution analytical procedures such as crystallization, electrophoresis, and chromatography. The "enantiomer" refers to two stereoisomers that are non-overlapping mirror images of each other.

As used herein, the term "tautomer" refers to structural isomers with different energies, which can inter-convert via a low energy barrier. For example, a proton tautomer (also referred to as a prototropic tautomer) includes the inter-conversion via proton transfer, such as keto-enol isomerization and imine-enamine isomerization. A valence tautomer includes the inter-conversion via recombination of some bonding electrons.

As used herein, the term "pharmaceutically acceptable salt" refers to a pharmaceutically acceptable organic or inorganic salt of the compound of the present invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methanesulfonate, ethanesulfonate, benzenesulfonate, p-toluenesulfonate, pamoate, ammonium salts (e.g., primary amine salts, secondary amine salts, tertiary amine salts, and quaternary ammonium salts), and metal salts (e.g., sodium salts, potassium salts, calcium salts, magnesium salts, manganese salts, iron salts, zinc salts, copper salts, lithium salts, and aluminum salts).

As used herein, the term "pharmaceutically acceptable" means that the substance or composition must be compatible chemically and/or toxicologically with the other ingredients comprised in a preparation, and/or the mammal being treated therewith.

As used herein, the term "treating" refers to therapeutic treatments and prophylactic or preventative or protective measures, which aim to prevent or slow down (alleviate) an undesired pathological change or disorder. For purposes of the present invention, beneficial or desired clinical results include, but are not limited to, alleviation of symptoms, reduction in disease severity, delay or slowing of disease progression, amelioration or palliation of the disease state, and remission (whether partial or total), whether detectable or undetectable.

As used herein, the term "therapeutically effective amount" means that an amount of a compound of the present invention that (i) treats or prevents a disease or disorder described herein, (ii) alleviates or eliminates one or more diseases or disorders described herein, or (iii) prevents or delays the onset of one or more symptoms of a disease or disorder described herein.

In one embodiment, in a compound of formula (I) or a stereoisomer, a tautomer or a pharmaceutically acceptable salt thereof provided herein: X is $NR_9$, wherein the $R_9$ is selected from H and $C_1$-$C_6$ alkyl; Y is selected from a covalent bond, —O—, —S—, —S(O)—, and —S(O)$_2$—;

$R_1$ is selected from $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$, $R_3$, and $R_{10}$ are each independently selected from H, hydroxy, $C_1$-$C_6$ alkyl, $C_2$-$C_6$ alkenyl, $C_2$-$C_6$ alkynyl, $C_1$-$C_6$ alkoxy, halogen, and —CN;

$R_4$ is $C_3$-$C_6$ cycloalkyl; wherein the $C_3$-$C_6$ cycloalkyl is optionally substituted with -Q-T, wherein the Q is selected from a covalent bond, —$CH_2$—, —C(=O)—, —O—, —S—, —S(O)—, —S(O)$_2$—, and —$NR_9'$—, wherein the $R_9'$ is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and $C_1$-$C_6$ alkyl; and $R_6$, $R_7$, and $R_8$ are each independently selected from H, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—, wherein the $C_1$-$C_6$ alkyl, the $C_2$-$C_6$ alkenyl, the $C_2$-$C_6$ alkynyl, the $C_1$-$C_6$ alkoxy, the $C_1$-$C_6$ alkyl-S—, the $C_1$-$C_6$ alkyl-NH—, the ($C_1$-$C_6$ alkyl)$_2$N—, the $C_1$-$C_6$ alkyl-C(=O)—, the $C_1$-$C_6$ alkyl-S(O)—, the $C_1$-$C_6$ alkyl-S(O)$_2$—, the $C_1$-$C_6$ alkyl-OC(=O)—, and the $C_1$-$C_6$ alkyl-OS(O)$_2$ are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a preferred embodiment, in a compound of formula (I) or a stereoisomer, a tautomer or a pharmaceutically acceptable salt thereof provided herein:

X is $NR_9$, wherein the $R_9$ is selected from H and $C_1$-$C_6$ alkyl; Y is selected from a covalent bond, —O—, —S—, —S(O)—, and —S(O)$_2$—;

$R_1$ is selected from $C_3$-$C_{12}$ cycloalkyl, 3-12 membered heterocyclyl; wherein the $C_3$-$C_{12}$ cycloalkyl and the 3-12 membered heterocyclyl are optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$, $R_3$, and $R_{10}$ are each independently selected from H, hydroxy, $C_1$-$C_6$ alkyl, $C_2$-$C_6$ alkenyl, $C_2$-$C_6$ alkynyl, $C_1$-$C_6$ alkoxy, halogen, and —CN;

$R_4$ is $C_3$-$C_6$ cycloalkyl; wherein the $C_3$-$C_6$ cycloalkyl is optionally substituted with -Q-T, wherein the Q is selected from a covalent bond, —$CH_2$—, —C(=O)—, —O—, —S—, —S(O)—, —S(O)$_2$—, and —$NR_9'$—, wherein the $R_9'$ is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and $C_1$-$C_6$ alkyl; and $R_6$, $R_7$, and $R_8$ are each independently selected from H, hydroxy, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—, wherein the $C_1$-$C_6$ alkyl, the $C_2$-$C_6$ alkenyl, the $C_2$-$C_6$ alkynyl, the $C_1$-$C_6$ alkoxy, the $C_1$-$C_6$ alkyl-S—, the $C_1$-$C_6$ alkyl-NH—, the ($C_1$-$C_6$ alkyl)$_2$N—, the $C_1$-$C_6$ alkyl-C(=O)—, the $C_1$-$C_6$ alkyl-S(O)—, the $C_1$-$C_6$ alkyl-S(O)$_2$—, the $C_1$-$C_6$ alkyl-OC(=O)—, and the $C_1$-$C_6$ alkyl-OS(O)$_2$ are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein: X is $NR_9$, wherein the $R_9$ is selected from H and $C_1$-$C_6$ alkyl; Y is selected from a covalent bond, —O—, —S—, —S(O)—, and —S(O)$_2$—;

$R_1$ is selected from $C_3$-$C_6$ cycloalkyl and 3-12 membered heterocyclyl; wherein the $C_3$-$C_6$ cycloalkyl or the 3-12 membered heterocyclyl is optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$ is selected from H, $C_1$-$C_6$ alkyl, and halogen;

$R_3$ and $R_{10}$ are H;

$R_4$ is $C_3$-$C_6$ cycloalkyl; wherein the $C_3$-$C_6$ cycloalkyl is optionally substituted with -Q-T, wherein the Q is selected from a covalent bond, —$CH_2$—, —C(=O)—, —O—, —S—, —S(O)—, —$S(O)_2$—, and —$NR_9$'—, wherein the $R_9$' is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-$S(O)_2$—, $C_1$-$C_6$ alkyl-OC(=O)—, and $C_1$-$C_6$ alkyl-$OS(O)_2$—;

$R_5$ is selected from H and $C_1$-$C_6$ alkyl; and $R_6$ and $R_8$ are each independently selected from $C_1$-$C_6$ alkyl, $C_1$-$C_6$ alkoxy, and —OH, wherein the $C_1$-$C_6$ alkyl is optionally substituted with —OH; and $R_7$ is selected from H and $C_1$-$C_6$ alkyl.

In a further preferred embodiment, in a compound of formula (I) or a stereoisomer, a tautomer or a pharmaceutically acceptable salt thereof provided herein: X is $NR_9$, wherein the $R_9$ is ethyl;

Y is selected from a covalent bond, —O—, —S—, —S(O)—, and —$S(O)_2$—;

$R_1$ is selected from $C_5$-$C_6$ cycloalkyl and 5-8 membered heterocyclyl; wherein the $C_5$-$C_6$ cycloalkyl or the 5-8 membered heterocyclyl is optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-$S(O)_2$—, $C_1$-$C_6$ alkyl-OC(=O)—, $C_1$-$C_6$ alkyl-$OS(O)_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$ is selected from H, $C_1$-$C_6$ alkyl, and halogen;

$R_3$ and $R_{10}$ are H;

$R_4$ is $C_3$-$C_6$ cycloalkyl; wherein the $C_3$-$C_6$ cycloalkyl is optionally substituted with -Q-T, wherein the Q is selected from a covalent bond, —$CH_2$—, —C(=O)—, —O—, —S—, —S(O)—, —$S(O)_2$—, and —$NR_9$'—, wherein the $R_9$' is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-$S(O)_2$—, $C_1$-$C_6$ alkyl-OC(=O)—, and $C_1$-$C_6$ alkyl-$OS(O)_2$—;

$R_5$ is selected from H and $C_1$-$C_6$ alkyl; and $R_6$ is $C_1$-$C_6$ alkyl;

$R_7$ is selected from H and $C_1$-$C_6$ alkyl; and $R_8$ is selected from $C_1$-$C_6$ alkyl, $C_1$-$C_6$ alkoxy, and —OH, wherein the $C_1$-$C_6$ alkyl is optionally substituted with —OH.

In a further preferred embodiment, in a compound of formula (I) or a stereoisomer, a tautomer or a pharmaceutically acceptable salt thereof provided herein: X is $NR_9$, wherein the $R_9$ is ethyl;

Y is selected from a covalent bond, —O—, —S—, —S(O)—, and —$S(O)_2$—;

$R_1$ is selected from $C_5$-$C_6$ cycloalkyl and 5-8 membered heterocyclyl; wherein the $C_5$-$C_6$ cycloalkyl or the 5-8 membered heterocyclyl is optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-$S(O)_2$—, $C_1$-$C_6$ alkyl-OC(=O)—, $C_1$-$C_6$ alkyl-$OS(O)_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$ is selected from H, $C_1$-$C_6$ alkyl, and halogen;

$R_3$ and $R_{10}$ are H;

$R_4$ is cyclobutyl; wherein the cyclobutyl is optionally substituted with -Q-T, wherein the Q is selected from a covalent bond, —$CH_2$—, —C(=O)—, —O—, —S—, —S(O)—, —$S(O)_2$—, and —$NR_9$'N, wherein the $R_9$' is selected from H, $C_1$-$C_6$ alkyl, and $C_1$-$C_6$ haloalkyl; and the T is selected from H, halogen, —CN, $C_1$-$C_6$ alkyl, $C_2$-$C_6$ alkenyl, $C_2$-$C_6$ alkynyl, $C_3$-$C_{12}$ cycloalkyl, 3-12 membered heterocyclyl, 6-10 membered aryl, and 5-6 membered heteroaryl; wherein the $C_1$-$C_6$ alkyl, the $C_2$-$C_6$ alkenyl, the $C_2$-$C_6$ alkynyl, the $C_3$-$C_{12}$ cycloalkyl, the 3-12 membered heterocyclyl, the 6-10 membered aryl, and the 5-6 membered heteroaryl are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-$S(O)_2$—, $C_1$-$C_6$ alkyl-OC(=O)—, and $C_1$-$C_6$ alkyl-$OS(O)_2$—;

$R_5$ is selected from H and $C_1$-$C_6$ alkyl;

$R_6$ is $C_1$-$C_6$ alkyl;

$R_7$ is H; and $R_8$ is selected from $C_1$-$C_6$ alkyl, $C_1$-$C_6$ alkoxy, and —OH, wherein the $C_1$-$C_6$ alkyl is optionally substituted with —OH.

In a further preferred embodiment, in a compound of formula (I) or a stereoisomer, a tautomer or a pharmaceutically acceptable salt thereof provided herein:

X is $NR_9$, wherein the $R_9$ is ethyl;

Y is —O—;

$R_1$ is selected from $C_5$-$C_6$ cycloalkyl and 5-8 membered heterocyclyl; wherein the $C_5$-$C_6$ cycloalkyl or the 5-8 membered heterocyclyl is optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$ is selected from H, $C_1$-$C_6$ alkyl, and halogen;

$R_3$ and $R_{10}$ are H;

$R_4$ is cyclobutyl; wherein the cyclobutyl is optionally substituted with -Q-T, wherein the Q is selected from a covalent bond and —CH$_2$—, and the T is selected from 3-12 membered heterocyclyl; wherein the 3-12 membered heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and $C_1$-$C_6$ alkyl;

$R_6$ is $C_1$-$C_6$ alkyl;

$R_7$ is H; and $R_8$ is selected from $C_1$-$C_6$ alkyl, $C_1$-$C_6$ alkoxy, and —OH, wherein the $C_1$-$C_6$ alkyl is optionally substituted with —OH.

In a further preferred embodiment, in a compound of formula (I) or a stereoisomer, a tautomer or a pharmaceutically acceptable salt thereof provided herein:

X is $NR_9$, wherein the $R_9$ is ethyl;

Y is —O—;

$R_1$ is selected from $C_5$-$C_6$ cycloalkyl and 5-8 membered heterocyclyl; wherein the $C_5$-$C_6$ cycloalkyl or the 5-8 membered heterocyclyl is optionally substituted with one or more groups selected from $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ alkyl-S—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, $C_1$-$C_6$ alkyl-OS(O)$_2$—, halogen, —CN, —OH, and $NR_1'R_1''$; wherein the $R_1'$ and the $R_1''$ are each independently selected from H, $C_1$-$C_6$ alkyl, $C_2$-$C_6$ alkenyl, and $C_2$-$C_6$ alkynyl, and wherein the $C_1$-$C_6$ alkyl, the $C_2$-$C_6$ alkenyl, and the $C_2$-$C_6$ alkynyl are optionally substituted with one or more groups selected from $C_1$-$C_6$ alkoxy, halogen, —OH, —CN, —SH, and $NH_2$;

$R_2$ is selected from H, $C_1$-$C_6$ alkyl, and halogen;

$R_3$ and $R_{10}$ are H;

$R_4$ is cyclobutyl; wherein the cyclobutyl is optionally substituted with -Q-T, wherein the Q is selected from a covalent bond and —CH$_2$—, and the T is selected from 5-8 membered nitrogen-containing heterocyclyl; wherein the 5-8 membered nitrogen-containing heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and $C_1$-$C_6$ alkyl;

$R_6$ is $C_1$-$C_6$ alkyl;

$R_7$ is H; and $R_8$ is selected from $C_1$-$C_6$ alkyl, $C_1$-$C_6$ alkoxy, and —OH, wherein the $C_1$-$C_6$ alkyl is optionally substituted with —OH.

In a further preferred embodiment, in a compound of formula (I) or a stereoisomer, a tautomer or a pharmaceutically acceptable salt thereof provided herein:

$R_4$ is

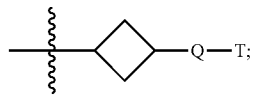

wherein the Q is selected from a covalent bond and —CH$_2$—, and the T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

$R_4$ is

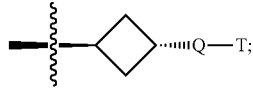

wherein the Q is selected from a covalent bond and —CH$_2$—, and the T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

$R_4$ is

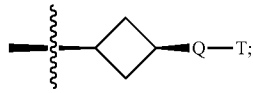

wherein the Q is selected from a covalent bond and —CH$_2$—, and the T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

$R_4$ is

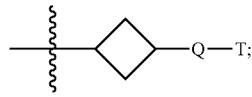

wherein the Q is selected from a covalent bond and —CH$_2$—, and the T is selected from

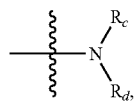

wherein the Rc and the Rd, together with the nitrogen atom to which they are attached, form 5-8 membered nitrogen-containing heterocyclyl, wherein the 5-8 membered nitrogen-containing heterocyclyl is optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

The T is selected from morpholinyl, piperidinyl, piperazinyl, 8-oxa-3-azabicyclo[3.2.1]octyl, and 6-oxa-3-azabicyclo[3.1.1]heptanyl; wherein the morpholinyl, the piperidinyl, the piperazinyl, the 8-oxa-3-azabicyclo[3.2.1]octanyl, and the 6-oxa-3-azabicyclo[3.1.1]heptanyl are optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

X is NR$_9$, wherein the R$_9$ is ethyl;
Y is —O—;
$R_1$ is selected from cyclopentyl, cyclohexyl, tetrahydrofuranyl, tetrahydropyranyl, tetrahydropyrrolyl, piperidinyl, and 8-oxabicyclo[3.2.1]octane; wherein the cyclopentyl, the cyclohexyl, the tetrahydrofuranyl, the tetrahydropyranyl, the tetrahydropyrrolyl, the piperidinyl, and the 8-oxabicyclo[3.2.1]octane are optionally substituted with one or more groups selected from $C_1$-$C_6$ alkyl, $C_1$-$C_6$ haloalkyl, halogen, —CN, and NR$_1$'R$_1$"; wherein the R$_1$' and the R$_1$" are each independently selected from H and $C_1$-$C_6$ alkyl, and wherein the $C_1$-$C_6$ alkyl is optionally substituted with one or more groups selected from $C_1$-$C_6$ alkoxy;
$R_2$ is selected from methyl, fluoro, and chloro;
$R_3$ and $R_{10}$ are H;
$R_4$ is

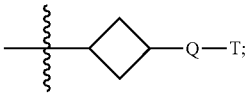

wherein the Q is selected from a covalent bond and —CH$_2$—, and the T is selected from morpholinyl, piperidinyl, piperazinyl, 8-oxa-3-azabicyclo[3.2.1]octanyl, and 6-oxa-3-azabicyclo[3.1.1]heptanyl; wherein the morpholinyl, the piperidinyl, the piperazinyl, the 8-oxa-3-azabicyclo[3.2.1]octanyl, and the 6-oxa-3-azabicyclo[3.1.1]heptanyl are optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;
$R_5$ is selected from H and methyl;
$R_6$ is methyl;
$R_7$ is H; and
$R_8$ is selected from methyl, methoxy, —OH, and —CH$_2$OH.

In a further preferred embodiment, in a compound of formula (I) or a stereoisomer, a tautomer or a pharmaceutically acceptable salt thereof provided herein:

X is NR$_9$, wherein the R$_9$ is ethyl;
Y is —O—;
$R_1$ is selected from cyclopentyl, cyclohexyl, tetrahydrofuranyl, tetrahydropyranyl, tetrahydropyrrolyl, piperidinyl, and 8-oxabicyclo[3.2.1]octane; wherein the cyclopentyl, the cyclohexyl, the tetrahydrofuranyl, the tetrahydropyranyl, the tetrahydropyrrolyl, the piperidinyl, and the 8-oxabicyclo[3.2.1]octane are optionally substituted with one or more groups selected from $C_1$-$C_6$ alkyl, $C_1$-$C_6$ haloalkyl, halogen, —CN, and NR$_1$'R$_1$"; wherein the R$_1$' and the R$_1$" are each independently selected from H and $C_1$-$C_6$ alkyl, and wherein the $C_1$-$C_6$ alkyl is optionally substituted with one or more groups selected from $C_1$-$C_6$ alkoxy;
$R_2$ is selected from methyl, fluoro, and chloro;
$R_3$ and $R_{10}$ are H;
$R_4$ is

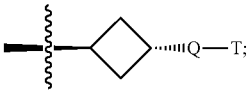

wherein the Q is selected from a covalent bond and —CH$_2$—, and the T is selected from morpholinyl, piperidinyl, piperazinyl, 8-oxa-3-azabicyclo[3.2.1]octanyl, and 6-oxa-3-azabicyclo[3.1.1]heptanyl; wherein the morpholinyl, the piperidinyl, the piperazinyl, the 8-oxa-3-azabicyclo[3.2.1]octanyl, and the 6-oxa-3-azabicyclo[3.1.1]heptanyl are optionally substituted with one or more groups selected from —OH, —SH, —NH$_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—;

$R_5$ is selected from H and methyl;

$R_6$ is methyl;

$R_7$ is H; and $R_8$ is selected from methyl, methoxy, —OH, and —CH$_2$OH.

In another preferred embodiment, in a compound of formula (I) or a stereoisomer, a tautomer or a pharmaceutically acceptable salt thereof provided herein:

X is NR$_9$, wherein the R$_9$ is ethyl;

Y is —O—;

$R_1$ is selected from cyclopentyl, cyclohexyl, tetrahydrofuranyl, tetrahydropyranyl, tetrahydropyrrolyl, piperidinyl, and 8-oxabicyclo[3.2.1]octane; wherein the cyclopentyl, the cyclohexyl, the tetrahydrofuranyl, the tetrahydropyranyl, the tetrahydropyrrolyl, the piperidinyl, and the 8-oxabicyclo[3.2.1]octane are optionally substituted with one or more groups selected from C$_1$-C$_6$ alkyl, C$_1$-C$_6$ haloalkyl, halogen, —CN, and NR$_1$'R$_1$''; wherein the R$_1$' and the R$_1$'' are each independently selected from H and C$_1$-C$_6$ alkyl, and wherein the C$_1$-C$_6$ alkyl is optionally substituted with one or more groups selected from C$_1$-C$_6$ alkoxy;

$R_2$ is selected from methyl, fluoro, and chloro;

$R_3$ and $R_{10}$ are H;

$R_4$ is

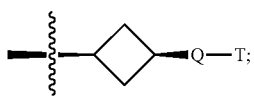

wherein the Q is selected from a covalent bond and —CH$_2$—, and the T is selected from morpholinyl, piperidinyl, piperazinyl, 8-oxa-3-azabicyclo[3.2.1]octanyl, and 6-oxa-3-azabicyclo[3.1.1]heptanyl; wherein the morpholinyl, the piperidinyl, the piperazinyl, the 8-oxa-3-azabicyclo[3.2.1]octanyl, and the 6-oxa-3-azabicyclo[3.1.1]heptanyl are optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—;

$R_5$ is selected from H and methyl;

$R_6$ is methyl;

$R_7$ is H; and $R_8$ is selected from methyl, methoxy, —OH, and —CH$_2$OH.

In a further preferred embodiment, in a compound of formula (I) or a stereoisomer, a tautomer or a pharmaceutically acceptable salt thereof provided herein:

$R_1$ is selected from

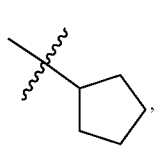, 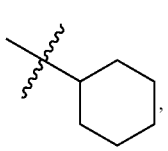, 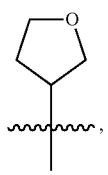, 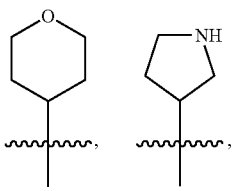 and 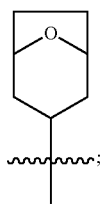;

wherein the

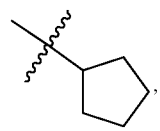 [SMILES: *C1CCCC1], the

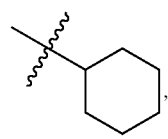 [SMILES: *C1CCCCC1], the

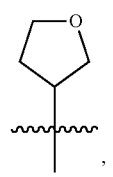 [SMILES: *C1CCOC1], the

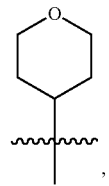, the

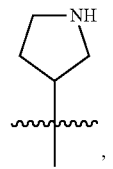 [SMILES: *C1CCNC1], the

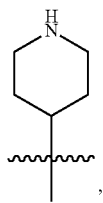, and the

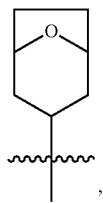, are optionally substituted with one or more groups selected from $C_1$-$C_6$ alkyl, $C_1$-$C_6$ haloalkyl, halogen, —CN, and $NR_1'R_1''$; wherein the $R_1'$ and the $R_1''$ are each independently selected from H and $C_1$-$C_6$ alkyl, and wherein the $C_1$-$C_6$ alkyl is optionally substituted with one or more groups selected from $C_1$-$C_6$ alkoxy; and the Q is selected from a covalent bond and —$CH_2$—, and the T is selected from

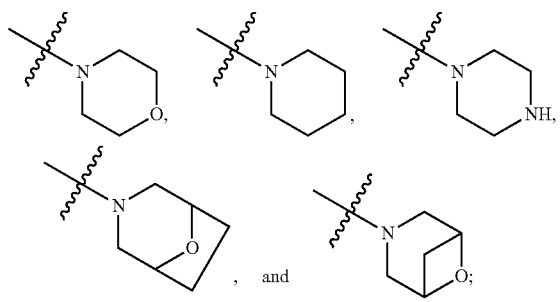

wherein the

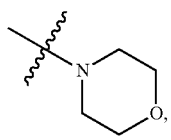 [SMILES: *N1CCOCC1], the

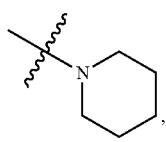 [SMILES: *N1CCCCC1 ; ","], the

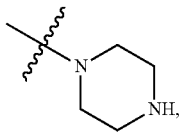, the

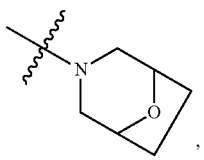 [SMILES: *N1CC2CCC(C1)O2], and the

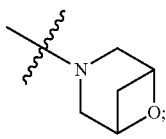 [SMILES: *N1CC2CC(C1)O2];

are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

In a further preferred embodiment, in a compound of formula (I) or a stereoisomer, a tautomer or a pharmaceutically acceptable salt thereof provided herein:

$R_1$ is selected from

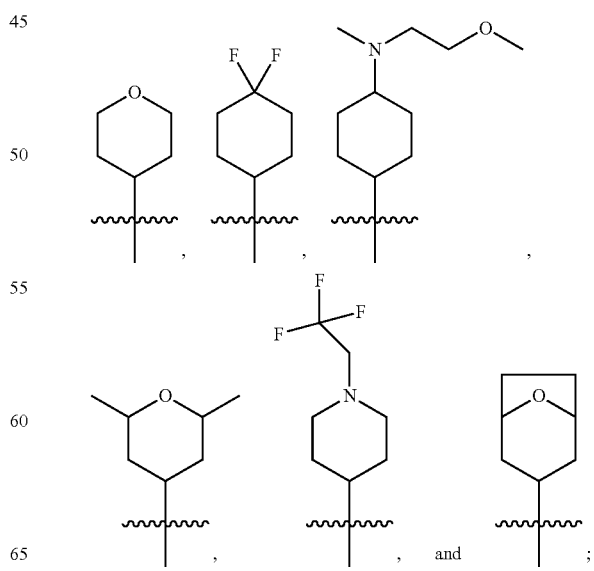

and
the Q is selected from a covalent bond and —CH₂—, and
the T is selected from:

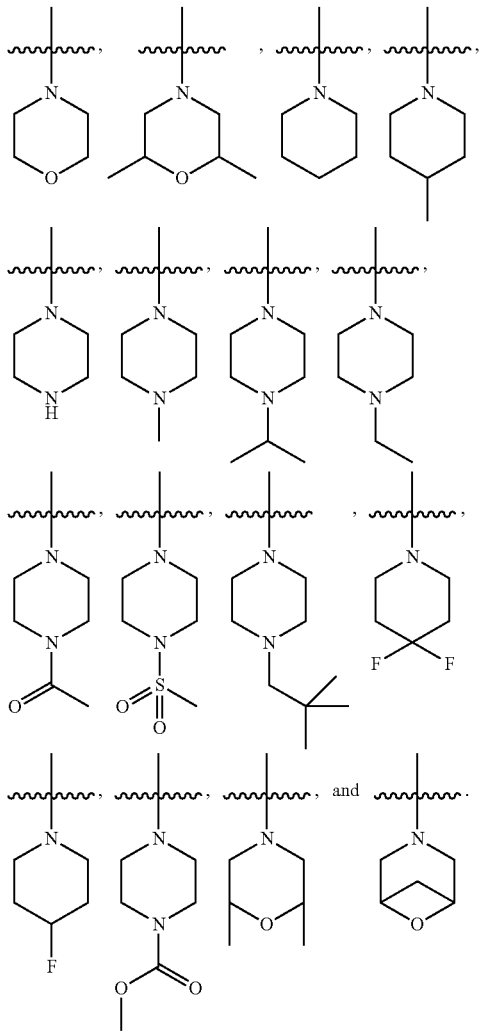

Preferred compounds of the present invention are shown below:
5-cyclobutoxy-N-((4,6-dimethyl-2-oxo-1,2-dihydropyridin-3-yl)methyl)-3-(ethyl(tetrahydro-2H-pyran-4-yl)amino)-2-methylbenzamide,
N-((4,6-dimethyl-2-oxo-1,2-dihydropyridin-3-yl)methyl)-3-(ethyl(tetrahydro-2H-pyran-4-yl) amino)-2-methyl-5-(3-methylcyclobutoxy)benzamide,
5-(3,3-difluorocyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide,
N-((4,6-dimethyl-2-oxo-1,2-dihydropyridin-3-yl)methyl)-3-(ethyl(tetrahydro-2H-pyran-4-yl)amino)-2-methyl-5-(trans-3-morpholinylcyclobutoxy)benzamide,
5-cyclobutoxy-N-((4,6-dimethyl-2-oxo-1,2-dihydropyridin-3-yl)methyl)-2-methyl-3-((tetrahydro-2H-pyran-4-yl)oxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(cis-3-(morpholinylmethyl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(trans-3-(morpholinylmethyl)cyclobutoxy)benzamide,
5-(cyclobutylthio)-N-((4,6-dimethyl-2-oxo-1,2-dihydropyridin-3-yl)methyl)-3-(ethyl (tetrahydro-2H-pyran-4-yl)amino)-2-methylbenzamide,
5-(cyclobutylsulfinyl)-N-((4,6-dimethyl-2-oxo-1,2-dihydropyridin-3-yl)methyl)-3-(ethyl (tetrahydro-2H-pyran-4-yl)amino)-2-methylbenzamide,
5-(cyclobutylsulfonyl)-N-((4,6-dimethyl-2-oxo-1,2-dihydropyridin-3-yl)methyl)-3-(ethyl (tetrahydro-2H-pyran-4-yl)amino)-2-methylbenzamide,
2-chloro-5-cyclobutoxy-N-((4,6-dimethyl-2-oxo-1,2-dihydropyridin-3-yl)methyl)-3-(ethyl (tetrahydro-2H-pyran-4-yl)amino)benzamide,
N-((4,6-dimethyl-2-oxo-1,2-dihydropyridin-3-yl)methyl)-5-(3,3-dimethylcyclobutoxy)-3-(ethyl(tetrahydro-2H-pyran-4-yl)amino)-2-methylbenzamide,
N-((4,6-dimethyl-2-oxo-1,2-dihydropyridin-3-yl)methyl)-3-(ethyl(tetrahydro-2H-pyran-4-yl)amino)-2-methyl-5-(3-(morpholine-4-carbonyl)cyclobutoxy)benzamide,
5-cyclopropyl-N-((4,6-dimethyl-2-oxo-1,2-dihydropyridin-3-yl)methyl)-3-(ethyl(tetrahydro-2H-pyran-4-yl)amino)-2-methylbenzamide,
5-cyclobutyl-N-((4,6-dimethyl-2-oxo-1,2-dihydropyridin-3-yl)methyl)-3-(ethyl(tetrahydro-2H-pyran-4-yl)amino)-2-methylbenzamide,
N-((4,6-dimethyl-2-oxo-1,2-dihydropyridin-3-yl)methyl)-3-(ethyl(tetrahydro-2H-pyran-4-yl)amino)-2-methyl-5-(3-(morpholinylmethyl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(cis-3-(piperazin-1-yl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(trans-3-(piperazin-1-yl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperazin-1-yl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperazin-1-yl)cyclobutoxy)benzamide,
N-((4,6-dimethyl-2-oxo-1,2-dihydropyridin-3-yl)methyl)-3-(ethyl(tetrahydro-2H-pyran-4-yl)amino)-5-(cis-3-(4-isopropylpiperazin-1-yl)cyclobutoxy)-2-methylbenzamide,
N-((4,6-dimethyl-2-oxo-1,2-dihydropyridin-3-yl)methyl)-3-(ethyl(tetrahydro-2H-pyran-4-yl)amino)-5-(trans-3-(4-isopropylpiperazin-1-yl)cyclobutoxy)-2-methylbenzamide,
N-((4,6-dimethyl-2-oxo-1,2-dihydropyridin-3-yl)methyl)-3-(ethyl(tetrahydro-2H-pyran-4-yl)amino)-5-(cis-3-(4-ethylpiperazin-1-yl)cyclobutoxy)-2-methylbenzamide,
N-((4,6-dimethyl-2-oxo-1,2-dihydropyridin-3-yl)methyl)-3-(ethyl(tetrahydro-2H-pyran-4-yl)amino)-5-(trans-3-(4-ethylpiperazin-1-yl)cyclobutoxy)-2-methylbenzamide,
cis-5-(3-(4-acetylpiperazin-1-yl)cyclobutoxy)-N-((4,6-dimethyl-2-oxo-1,2-dihydropyridin-3-yl)methyl)-3-(ethyl (tetrahydro-2H-pyran-4-yl)amino)-2-methylbenzamide,
trans-5-(3-(4-acetylpiperazin-1-yl)cyclobutoxy)-N-((4,6-dimethyl-2-oxo-1,2-dihydropyridin-3-yl)methyl)-3-(ethyl (tetrahydro-2H-pyran-4-yl)amino)-2-methylbenzamide,
N-((4,6-dimethyl-2-oxo-1,2-dihydropyridin-3-yl)methyl)-3-(ethyl(tetrahydro-2H-pyran-4-yl)amino)-2-methyl-5-(cis-3-(4-(methylsulfonyl)piperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(4-(methylsulfonyl)piperazin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(morpholinylmethyl)cyclobutoxy)benzamide, 2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)benzamide, N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)-2-methylbenzamide, N-((4,6-dimethyl-2-oxo-1,2-dihydropyridin-3-yl)methyl)-3-(ethyl(trans-4-((2-methoxyethyl) (methyl)amino)cyclohexyl)amino)-2-methyl-5-(trans-3-(morpholinylmethyl)cyclobutoxy)benzamide, N-((4,6-dimethyl-2-oxo-1,2-dihydropyridin-3-yl)methyl)-5-((cis-3-(cis-2,6-dimethylmorpholinyl)cyclobutoxy)-3-((cis-2,6-dimethyltetrahydro-2H-pyran-4-yl)(ethyl)amino)-2-methylbenzamide, N-((4,6-dimethyl-2-oxo-1,2-dihydropyridin-3-yl)methyl)-3-(ethyl(trans-4-((2-methoxyethyl) (methyl)amino)cyclohexyl)amino)-2-methyl-5-(3-morpholinylcyclobutoxy)benzamide, N-((4,6-dimethyl-2-oxo-1,2-dihydropyridin-3-yl)methyl)-5-(trans-3-(cis-2,6-dimethylmorpholinyl)cyclobutoxy)-3-((cis-2,6-dimethyltetrahydro-2H-pyran-4-yl)(ethyl)amino)-2-methylbenzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(piperidin-1-ylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperidin-1-yl)cyclobutoxy)benzamide, N-((4,6-dimethyl-2-oxo-1,2-dihydropyridin-3-yl)methyl)-5-((1S,3S)-3-((2S,6R)-2,6-dimethylmorpholinyl)cyclobutoxy)-3-(((2R,4s,6S)-2,6-dimethyltetrahydro-2H-pyran-4-yl) (ethyl)amino)-2-methylbenzamide, N-((4,6-dimethyl-2-oxo-1,2-dihydropyridin-3-yl)methyl)-5-(trans-3-(cis-2,6-dimethylmorpholinyl)cyclobutoxy)-3-((trans-2,6-dimethyltetrahydro-2H-pyran-4-yl)(ethyl)amino)-2-methylbenzamide, 2-chloro-N-((4,6-dimethyl-2-oxo-1,2-dihydropyridin-3-yl)methyl)-3-(ethyl(tetrahydro-2H-pyran-4-yl)amino)-5-(cis-3-morpholinylcyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-morpholinylcyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(cis-3-(piperazin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperazin-1-yl)cyclobutoxy)benzamide, N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)-2-methylbenzamide, 3-((4,4-difluorocyclohexyl)(ethyl)amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide, N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydrofuran-3-yl)amino)-2-methylbenzamide, 3-((8-oxabicyclo[3.2.1]octan-3-yl)(ethyl)amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide, 2-chloro-N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)benzamide, 5-(trans-3-(8-oxa-3-azabicyclo[3.2.1]octan-3-yl)cyclobutoxy)-2-chloro-N-((4,6-dimethyl-2-oxo-1,2-dihydropyridin-3-yl)methyl)-3-(ethyl(tetrahydro-2H-pyran-4-yl)amino)benzamide, N-((4,6-dimethyl-2-oxo-1,2-dihydropyridin-3-yl)methyl)-5-(trans-3-(cis-2,6-dimethylmorpholinyl)cyclobutoxy)-3-(ethyl (1-(2,2,2-trifluoroethyl) piperidin-4-yl)amino)-2-methylbenzamide, N-((4,6-dimethyl-2-oxo-1,2-dihydropyridin-3-yl)methyl)-3-(ethyl(tetrahydro-2H-pyran-4-yl)amino)-N,2-dimethyl-5-(trans-3-morpholinylcyclobutoxy)benzamide, N-((4,6-dimethyl-2-oxo-1,2-dihydropyridin-3-yl)methyl)-5-(trans-3-(cis-2,6-dimethylmorpholinyl)cyclobutoxy)-3-(ethyl(trans-4-((2-methoxyethyl)(methyl)amino) cyclohexyl)amino)-2-methylbenzamide, 2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)benzamide, 5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide, 5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)benzamide, N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperidin-1-yl)cyclobutoxy)benzamide, N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydro-2H-pyran-4-yl)amino)benzamide, N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydrofuran-3-yl)amino)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(4-methylpiperidin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-ylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-fluoro-5-(trans-3-(morpholinomethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-fluoro-5-(trans-3-morpholinocyclobutoxy)benzamide, 3-((4,4-difluorocyclohexyl)(ethyl)amino)-N-((4,6-dimethyl-2-oxo-1,2-dihydropyridin-3-yl)methyl)-2-methyl-5-(trans-3-morpholinocyclobutoxy)benzamide, N-((4,6-dimethyl-2-oxo-1,2-dihydropyridin-3-yl)methyl)-3-(ethyl(tetrahydrofuran-3-yl) amino)-2-methyl-5-(trans-3-morpholin-4-ylcyclobutoxy)benzamide, 2-chloro-3-((4,4-difluorocyclohexyl)(ethyl)amino)-N-((4,6-dimethyl-2-oxo-1,2-dihydropyridin-3-yl)methyl)-5-(trans-3-(4-methylpiperidin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(4,4-difluoropiperidin-1-yl)cyclobutoxy)benzamide, 3-((4,4-difluorocyclohexyl)(ethyl)amino)-N-((4,6-dimethyl-2-oxo-1,2-dihydropyridin-3-yl)methyl)-2-methyl-5-(trans-3-(piperidin-1-yl)cyclobutoxy)benzamide, 2-chloro-3-((4,4-difluorocyclohexyl)(ethyl)amino)-N-((4,6-dimethyl-2-oxo-1,2-dihydropyridin-3-yl)methyl)-5-(trans-3-(cis-2,6-dimethylmorpholino)cyclobutoxy)benzamide, 2-chloro-3-((4,4-difluorocyclohexyl)(ethyl)amino)-N-((4,6-dimethyl-2-oxo-1,2-dihydropyridin-3-yl)methyl)-5-(cis-3-(4-methylpiperidin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-5-(2-(hydroxymethyl)cyclopropyl)-2-methylbenzamide, N-((4,6-dimethyl-2-oxo-1,2-dihydropyridin-3-yl)methyl)-3-(ethyl(tetrahydro-2H-pyran-4-yl)amino)-2-methyl-5-(2-(morpholinylmethyl)cyclopropyl)benzamide, N-((4,6-dimethyl-2-oxo-1,2-dihydropyridin-3-yl)methyl)-3-(ethyl(tetrahydro-2H-pyran-4-yl)amino)-2-methyl-5-(2-(piperazin-1-ylmethyl)cyclopropyl)benzamide, N-((4,6-dimethyl-2-oxo-1,2-dihydropyridin-3-yl)methyl)-3-(ethyl(tetrahydro-2H-pyran-4-yl)amino)-2-methyl-5-(2-((4-methylpiperazin-1-yl)methyl)cyclopropyl)benzamide, N-((4,6-dimethyl-2-oxo-1,2-dihydropyridin-3-yl)methyl)-5-(2-((cis-2,6-dimethylmorpholinyl)methyl)cyclopropyl)-3-(ethyl(tetrahydro-2H-pyran-4-yl)amino)-2-methylbenzamide, N-((4,6-dimethyl-2-oxo-1,2-dihydropyridin-3-yl)methyl)-3-(ethyl(tetrahydro-2H-pyran-4-yl)amino)-2-methyl-5-(2-((4-neopentylpiperazin-1-yl)methyl)cyclopropyl)benzamide, N-((4,6-dimethyl-2-oxo-1,2-dihydropyridin-3-yl)methyl)-3-(ethyl(tetrahydro-2H-pyran-4-yl)amino)-2-methyl-5-(2-(piperidin-1-ylmethyl)cyclopropyl)benzamide, 5-(2-((4,4-difluoropiperidin-1-yl)methyl)cyclopropyl)-N-((4,6-dimethyl-2-oxo-1,2-dihydropyridin-3-yl)methyl)-3-(ethyl(tetrahydro-2H-pyran-4-yl)amino)-2-methylbenzamide, N-((4,6-dimethyl-2-oxo-1,2-dihydropyridin-3-yl)methyl)-3-(ethyl(tetrahydro-2H-pyran-4-yl)amino)-5-(2-((4-fluoropiperidin-1-yl)methyl)cyclopropyl)-2-methylbenzamide, methyl 4-((2-(3-(((4,6-dimethyl-2-oxo-1,2-dihydropyridin-3-yl)methyl) carbamoyl)-5-(ethyl(tetrahydro-2H-pyran-4-yl)amino)-4-methylphenyl)cyclopropyl)methyl)piperazine-1-carboxylate, N-((4,6-dimethyl-2-oxo-1,2-dihydropyridin-3-yl)methyl)-3-(ethyl(trans-4-((2-methoxyethyl) (methyl)amino)cyclohexyl)amino)-2-methyl-5-(2-((4-methylpiperazin-1-yl)methyl)cyclopropyl)benzamide, N-((4,6-dimethyl-2-oxo-1,2-dihydropyridin-3-yl)methyl)-3-(ethyl(trans-4-((2-methoxyethyl) (methyl)amino)cyclohexyl)amino)-2-methyl-5-(2-(morpholinylmethyl)cyclopropyl)benzamide, 2-chloro-N-((4,6-dimethyl-2-oxo-1,2-dihydropyridin-3-yl)methyl)-3-(ethyl(tetrahydro-2H-pyran-4-yl)amino)-5-(2-(piperazin-1-ylmethyl)cyclopropyl)benzamide, 2-chloro-N-((4,6-dimethyl-2-oxo-1,2-dihydropyridin-3-yl)methyl)-3-(ethyl(tetrahydro-2H-pyran-4-yl)amino)-5-(2-(morpholinylmethyl)cyclopropyl)benzamide, 2-chloro-N-((4,6-dimethyl-2-oxo-1,2-dihydropyridin-3-yl)methyl)-5-(2-(((2S,6R)-2,6-dimethylmorpholinyl)methyl)cyclopropyl)-3-(ethyl(tetrahydro-2H-pyran-4-yl)amino)benzamide, 3-((8-oxabicyclo[3.2.1]octan-3-yl)(ethyl)amino)-N-((4,6-dimethyl-2-oxo-1,2-dihydropyridin-3-yl)methyl-2-methyl-5-(trans-3-morpholinocyclobutoxy)benzamide, 3-((4,4-difluorocyclohexyl)(ethyl)amino)-5-(trans-3-(cis-2,6-dimethylmorpholino) cyclobutoxy)-N-((4-methoxy-6-methyl-2-oxo-1,2-dihydropyridin-3-yl)methyl)-2-methylbenzamide, 3-((8-oxabicyclo[3.2.1]octan-3-yl)(ethyl)amino)-N-((4-methoxy-6-methyl-2-oxo-1,2-dihydropyridin-3-yl)methyl)-5-(trans-3-(cis-2,6-dimethylmorpholino)cyclobutoxy)-2-methylbenzamide, 2-chloro-3-(ethyl(tetrahydro-2H-pyran-4-yl)amino)-N-((4-methoxy-6-methyl-2-oxo-1,2-dihydropyridin-3-yl)methyl)-5-(trans-3-(4-methylpiperazin-1-yl)cyclobutoxy)benzamide, 2-chloro-3-(ethyl(tetrahydro-2H-pyran-4-yl)amino)-N-((4-methyl-2-oxo-6-(trifluoromethyl)-1,2-dihydropyridin-3-yl)methyl)-5-(trans-3-(4-methylpiperazin-1-yl)cyclobutoxy)benzamide, 3-((4,4-difluorocyclohexyl)(ethyl)amino)-N-((4-methoxy-6-methyl-2-oxo-1,2-dihydropyridin-3-yl)methyl)-2-methyl-5-(trans-3-(piperidin-1-yl)cyclobutoxy)benzamide, N-((4,6-dimethyl-2-oxo-1,2-dihydropyridin-3-yl)methyl-3-(ethyl(tetrahydro-2H-pyran-4-yl)amino)-2-methyl-5-(trans-3 (piperidin-1-yl)cyclobutoxy)benzamide, 3-(ethyl(tetrahydro-2H-pyran-4-yl)amino)-N-((4-methoxy-6-methyl-2-oxo-1,2-dihydropyridin-3-yl)methyl)-2-methyl-5-(trans-3-(piperidin-1-yl)cyclobutoxy)benzamide, 3-((4,4-difluorocyclohexyl)(ethyl)amino)-N-((4-hydroxy-6-methyl-2-oxo-1,2-dihydropyridin-3-yl)methyl)-2-methyl-5-(trans-3-(piperidin-1-yl)cyclobutoxy)benzamide, and 3-((4,4-difluorocyclohexyl)(ethyl)amino)-N-((4-hydroxymethyl-6-methyl-2-oxo-1,2-dihydropyridin-3-yl)methyl)-2-methyl-5-(trans-3-(piperidin-1-yl)cyclobutoxy)benzamide.

According to another aspect of the present invention, a method for preparing a compound of formula (I) disclosed herein is provided:

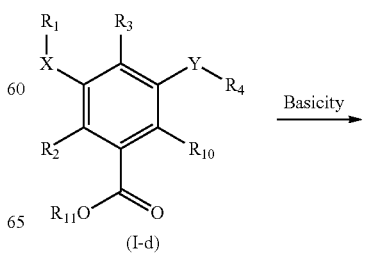

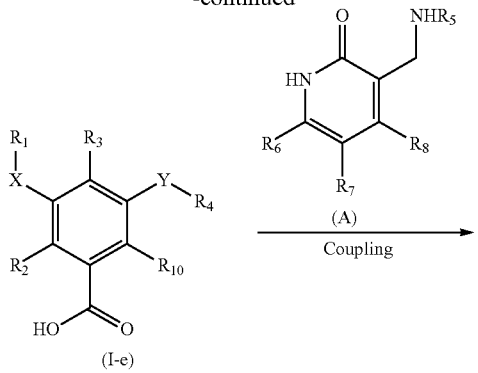

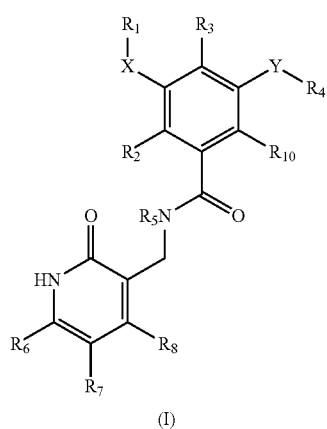

step one: hydrolyzing the intermediate (I-d) under basic conditions to give an intermediate (I-e); and step two: coupling the intermediate (I-e) with pyridone (A) to give the compound (I);

wherein $R_{11}$ is $C_1$-$C_6$ alkyl; $R_1$, $R_2$, $R_3$, $R_4$, $R_5$, $R_6$, $R_7$, $R_8$, $R_{10}$, X, and Y are as defined above for general formula (I); and the coupling reagent includes coupling reagents commonly used in the art for coupling or condensing carboxylic acids with amines, such as PyBOP, HATU, HBTU, HCTU, TBTU, TSTU, TNTU, BOP, HMPA, and PyAOP.

In a preferred embodiment, the method for preparing a compound of formula (I) disclosed herein further comprises:

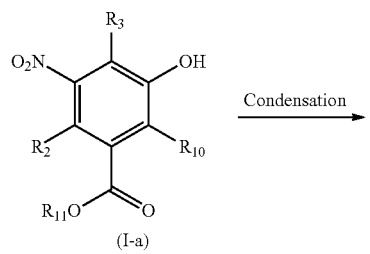

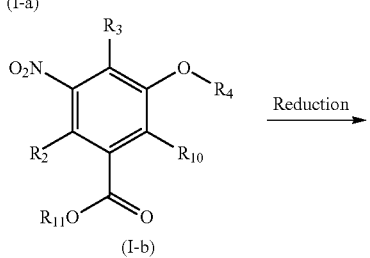

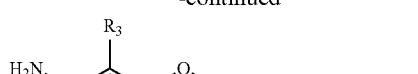

wherein $R_{11}$ is $C_1$-$C_6$ alkyl; and $R_1$, $R_2$, $R_3$, $R_4$, $R_9$, and $R_{10}$ are as defined above for formula (I);

step one: condensing the compound (I-a) with alcohol to give an intermediate (I-b); wherein the condensation reagent is a condensation reagent commonly used in the art, such as DEAD/PPh$_3$ and DIAD/PPh$_3$;

step two: reducing the intermediate (I-b) to give an intermediate (I-c); wherein the reductant includes but is not limited to iron powder, zinc powder, Pd/C/H$_2$, Raney nickel, etc.; and step three: reductively aminating the intermediate (I-c) with an amine compound to give an intermediate (I-d); wherein the reductive amination reagent includes but is not limited to sodium cyanoborohydride, sodium triacetoxyborohydride, etc.

In a preferred embodiment, the method for preparing a compound of formula (I) disclosed herein further comprises:

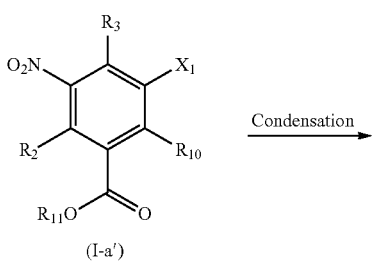

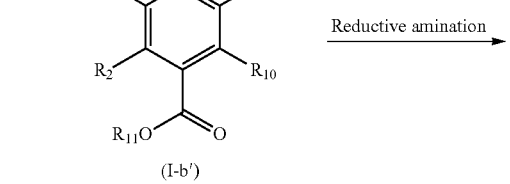

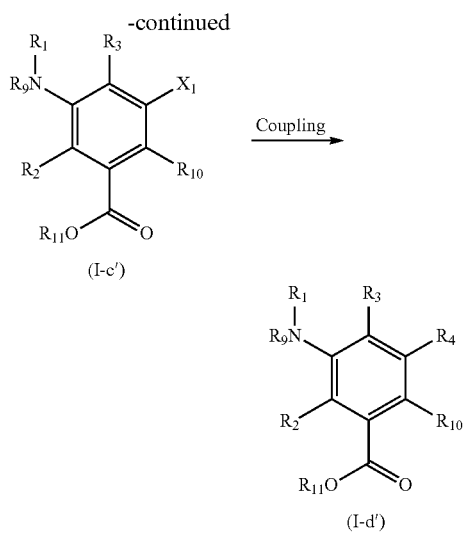

(I-c')

(I-d')

wherein $R_{11}$ is $C_1$-$C_6$ alkyl; $X_1$ is selected from halogen; and $R_1$, $R_2$, $R_3$, $R_4$, $R_9$, and $R_{10}$ are as defined above for formula (I);

step one: reducing the compound (I-a') to give an intermediate (I-b'); wherein the reductant includes but is not limited to iron powder, zinc powder, Pd/C/H$_2$, Raney nickel, etc.;

step two: reductively aminating the intermediate (I-b') with an amine compound to give an intermediate (I-c'); wherein the reductive amination reagent includes but is not limited to sodium cyanoborohydride, sodium triacetoxyborohydride, etc; and step three: coupling the intermediate (I-c') with a borane compound to give an intermediate (I-d'); the catalyst used in the reaction is a Suzuki reaction catalyst well known in the art.

In one embodiment, the present invention also provides a pharmaceutical composition comprising a compound of formula (I) or a pharmaceutically acceptable salt thereof as an active ingredient. The composition comprises the compound of the present invention or the pharmaceutically acceptable salt thereof and a pharmaceutically acceptable carrier. The pharmaceutically acceptable carrier may be a solid or a liquid. The solid carrier may be one or more substances used as excipients, diluents, sweeteners, solubilizers, lubricants, binders, tablet disintegrating agents, stabilizers, preservatives, or encapsulating materials. The liquid carrier may be a solvent or a liquid dispersion medium. Suitable solid carriers include, but are not limited to, for example, cellulose, glucose, lactose, mannitol, magnesium stearate, magnesium carbonate, sodium carbonate, sodium saccharin, sucrose, dextrin, talc, starch, pectin, gelatin, tragacanth, acacia, sodium alginate, methylparaben, methylcellulose, sodium carboxymethylcellulose, low-melting-point wax, cocoa butter, and the like. Suitable liquid carriers include, but are not limited to, water, ethanol, polyols (e.g., glycerol, propylene glycol, liquid polyethylene glycols, and the like), vegetable oils (e.g., peanut oil, cottonseed oil, safflower oil, sesame oil, olive oil, corn oil, and soybean oil), glycerides, agar, pyrogen-free water, isotonic saline, Ringer's solutions, and mixtures thereof.

The method for preparing the pharmaceutical composition disclosed herein is generally known in the art. Generally known methods for preparing the pharmaceutical composition disclosed herein include conventional mixing, granulating, tableting, coating, dissolving or lyophilizing processes.

The therapeutically effective amount of the compound or the pharmaceutical composition comprising the same described herein may be readily determined by routine experimentations. The most effective and convenient route of administration may be determined by routine experimentations.

The pharmaceutical composition disclosed herein may be administered to a patient or subject in need of treatment by any suitable route of administration, including oral administration, parenteral administration (including subcutaneous, intramuscular, intravenous, and intradermal administration), nasal spray administration, topical administration, rectal administration, intraperitoneal administration, buccal administration, vaginal administration or administration via an implantable reservoir. In some embodiments, the pharmaceutical composition disclosed herein may be intravenously and/or intraperitoneally administered.

The term "parenteral" as used herein includes subcutaneous, intravenous, intramuscular, intraocular, intravitreal, intraarticular, intrasynovial, intrasternal, intrathecal, intrahepatic, intraperitoneal, intralesional and intracranial injection or infusion techniques. Preferably, these pharmaceutical compositions are administered orally, subcutaneously, intraperitoneally or intravenously.

The orally administered compositions in the present invention include solid dosage forms such as pills, tablets, caplets, capsules (including immediate release, timed release and sustained release formulations), granules and powder; and liquid dosage forms such as solutions, syrups, elixirs, emulsions and suspensions. Sterile solutions or ocular drug delivery devices are intended for ocular administration. Sterile solutions, emulsions and suspensions are intended for parenteral administration.

The pharmaceutical composition disclosed herein may generally comprise about 1% to 99%, for example about 5% to 70% or about 10% to 50% (by weight) of a compound of formula (I) disclosed herein or a stereoisomer, a tautomer or a pharmaceutically acceptable salt thereof. The amount of the compound of formula (I) disclosed herein or a stereoisomer, a tautomer and a pharmaceutically acceptable salt thereof in the pharmaceutical composition may be 5 mg to 500 mg.

The dosage depends on various factors including the age, weight and condition of a patient and the route of administration. The exact dosage to be administered is left to the discretion of the attending physician. The actual dosage levels and time frame of active ingredients of the pharmaceutical composition disclosed herein may be varied so as to obtain an amount of the active ingredient that, for a particular patient, composition, and route of administration, may achieve the desired therapeutic response without posing toxicity to the patient.

The pharmaceutical composition disclosed herein may also comprise one or more additional therapeutically active agents. In this context, the additional one or more therapeutically active agents may include antimicrotubule agents (diterpenes (paclitaxel, docetaxel)), vinca alkaloids (vinblastine, vincristine, vinorelbine), platinum complexes (cisplatin, carboplatin), alkylation groups (mechlorethamine (cyclophosphamide, melphalan, chlorambucil)), alkylsulfonates (busulfan), nitrosoureas (carmustine), triazenes (dacarbazine), topoisomerase I inhibitors (irinotecan, topotecan), topoisomerase II inhibitors (etoposide, teniposide), antimetabolite neoplasias (fluorouracil, methotrexate, cytarabine, mercaptopurine, thioguanine, gemcitabine), histones and histone analogs (retinoic acid, histone deacetylase inhibitors), DNA methyltransferase inhibitors (azacitidine, decitabine), non-receptor tyrosine kinase angiogenesis inhibitors (endostatin, angiostatin), antibiotics (daunorubicin, doxorubicin, bleomycin), growth factor receptor inhibitors (VEGFR inhibitors (pazopanib, ZD6474, AZD2171, vatalanib, sunitinib, sorafenib), trastuzumab, cetuximab, bevacizumab, lapatinib, erlotinib, gefitinib, imatinib, ibrutinib, cell cycle signaling inhibitors (CDK inhibitors (ABT-751, vilipanib), PI3K inhibitors), anti-CD20 antibody drugs (such as rituximab, benituximab), anti-CD30 antibody drugs, PD-1 antibodies, PD-L1 antibodies, lenalidomide, bendamustine, BTK inhibitors, Bcl-2 inhibitors, CAR-T cell therapy, Aurora-A inhibitors, and the like.

The compound disclosed herein or the stereoisomer, tautomer or pharmaceutically acceptable salt thereof and a pharmaceutical composition comprising the same can be used for treating and/or preventing EZH2-mediated diseases. In one embodiment, EZH2-mediated diseases include cancer, pulmonary hypertension, myelofibrosis, human immunodeficiency virus (HIV) disease, graft versus host disease (GVHD), Weaver syndrome, psoriasis, hepatic fibrosis.

In one embodiment, EZH2-mediated disease is cancer. Cancer includes metastatic or malignant tumors.

In one embodiment, cancer includes brain cancer, thyroid cancer, cardiac sarcoma, lung cancer, oral cancer, stomach cancer, liver cancer, kidney cancer, pancreatic cancer, esophageal cancer, nasopharyngeal cancer, laryngeal cancer, colorectal cancer, breast cancer, prostate cancer, bladder cancer, ovarian cancer, uterine cancer, osteocarcinoma, melanoma, glioblastoma, lymphoma, leukemia, adrenal neuroblastoma, skin cancer, astrocytoma, and the like.

The present invention is further illustrated by the following specific examples, which are not intended to limit the present invention. Many modifications and variations may be made by those skilled in the art in light of the above teachings without departing from the spirit and scope of the present invention.

Example 1: Preparation of the Compound 5-cyclobutoxy-N-((4,6-dimethyl-2-oxo-1,2-dihydropyridin-3-yl)methyl)-3-(ethyl(tetrahydro-2H-pyran-4-yl)amino)-2-methylbenzamide (1)

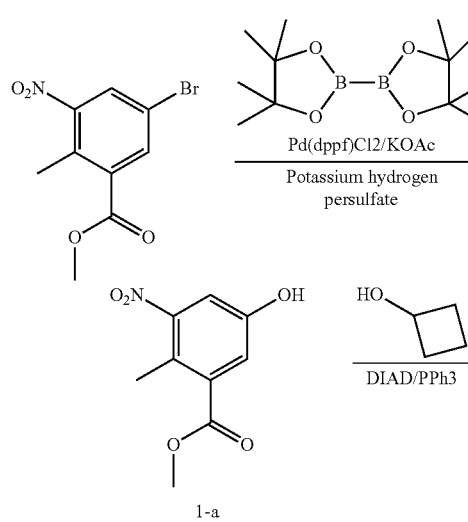

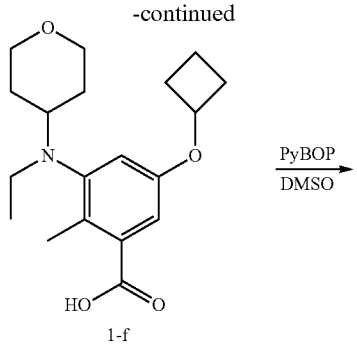

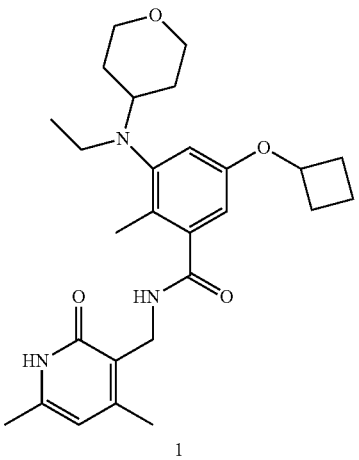

Preparation of Intermediate 1-a:

4,4,4',4',5,5,5',5'-octamethyl-2,2'-bi(1,3,2-dioxaborolane) (18.61 g, 73.26 mmol, 2 eq), Pd(dppf)Cl₂ (5.362 g, 7.326 mmol, 0.2 eq), and KOAc (8.974 g, 91.58 mmol, 2.5 eq) were added to a solution of methyl 5-bromo-2-methyl-3-nitrobenzoate (10 g, 36.64 mmol, 1 eq) in 1,4-dioxane (500 mL). The reaction mixture was stirred at 80° C. overnight under $N_2$ atmosphere. After TLC showed the reaction was completed, the mixture was filtered through celite and the solvent was removed under reduced pressure. The crude product was used in the next step directly without further purification. To a solution of methyl 2-methyl-3-nitro-5-(4,4,5,5-tetramethyl-1,3,2-dioxaborolan-2-yl)benzoate in ACN (100 mL) was added aqueous potassium hydrogen persulfate solution (100 mL) with stirring. The resulting reaction mixture was stirred at room temperature for 3 h. The reaction was quenched with aqueous $NaHSO_3$ solution. The solvent was removed under reduced pressure. The mixture was diluted with ethyl acetate and washed with saturated brine. The organic phase was dried over $Na_2SO_4$, filtered and evaporated to give the crude product. The crude product was purified by column chromatography (100-200 mesh silica gel), and eluted with ethyl acetate and petroleum ether to give the title compound methyl 5-hydroxy-2-methyl-3-nitrobenzoate (8.8 g, 61.5%) in the form of a white solid. 1H NMR (400 MHz, DMSO-d₆) δ 10.54-10.49 (s, 1H), 7.41-7.34 (m, 2H), 3.85-3.82 (s, 3H), 2.35-2.30 (s, 3H).

Preparation of Intermediate 1-b:

To a solution of methyl 5-hydroxy-2-methyl-3-nitrobenzoate (1 g, 4.74 mmol, 1 eq) in THF (15 mL) were added cyclobutanol (512 mg, 7.11 mmol, 1.5 eq) and PPh₃ (2.48 g, 9.48 mmol, 2 eq) with stirring. After stirring at 60° C. for 0.5 h, DIAD (1.91 g, 9.48 mmol, 2 eq) was added. The reaction mixture was stirred at 60° C. for 2 h. The solvent was removed under reduced pressure. The crude product was purified by TLC (PE:EA=10:1) to give the target product (870 mg, 69%) in the form of a light red oil. 1H NMR (300 MHz, DMSO-d₆) δ 7.55-7.51 (m, 1H), 7.47-7.43 (d, J=2.8 Hz, 3H), 4.90-4.74 (p, J=7.1 Hz, 1H), 3.89-3.87 (s, 3H), 2.49-2.40 (m, 2H), 2.39-2.35 (d, J=2.9 Hz, 3H), 2.17-1.95 (m, 6H), 1.90-1.55 (m, 6H).

Preparation of Intermediate 1-c:

To a solution of methyl 5-cyclobutoxy-2-methyl-3-nitrobenzoate (870 mg, 3.28 mmol, 1 eq) in ethanol (10 mL) was added an aqueous ammonium chloride (348 mg, 6.56 mmol, 2 eq) solution (10 mL) with stirring. Iron powder (919 mg, 16.4 mmol, 5 eq) was added with stirring. The resulting reaction mixture was heated at 80° C. for 2 h. After the reaction was completed, the reaction mixture was added with water and filtered through celite, and the brown filter cake was washed with ethyl acetate. The filtrate was extracted with ethyl acetate. The combined organic phases were washed with water, dried and concentrated under reduced pressure to give the crude product. The crude product was purified by TLC (PE:EA=2:1) to give the target compound (588 mg, 76.2%). M/z (ES⁺), [M+H]⁺=236; HPLC $t_R$=1.028 min. 1H NMR (400 MHz, DMSO-d₆) δ 6.39-6.30 (s, 7H), 5.11-5.04 (d, J=6.9 Hz, 2H), 4.62-4.49 (p, J=7.1 Hz, 1H), 3.79-3.75 (d, J=1.6 Hz, 15H), 2.49-2.31 (m, 2H), 2.12-2.07 (d, J=5.3 Hz, 3H), 2.06-1.92 (s, 2H), 1.82-1.70 (q, J=10.2 Hz, 1H), 1.71-1.56 (m, 1H).

Preparation of Intermediate 1-d:

To a solution of methyl 3-amino-5-cyclobutoxy-2-methylbenzoate (588 mg, 2.5 mmol, 1 eq) and dihydro-2H-pyran-4 (3H)-one (750.6 mg, 7.5 mmol, 3 eq) in methanol (65 mL) was added acetic acid (375 mg, 6.25 mmol, 2.5 eq) with stirring, and the reaction mixture was stirred at room temperature for 3 h. Then the reaction mixture was added with sodium cyanoborohydride (473 mg, 7.5 mmol, 3 eq) and stirred overnight. After the reaction was completed, the solvent was removed under reduced pressure. The reaction was quenched with aqueous $Na_2CO_3$ and ethyl acetate was added for extraction. The combined organic phases were washed with brine and dried over $Na_2SO_4$ to give the crude product. The crude product was used in the next step directly without further purification. M/z (ES⁺), [M+H]⁺=320; HPLC $t_R$=1.214 min.

Preparation of Intermediate 1-e:

To a solution of methyl 5-cyclobutoxy-2-methyl-3-((tetrahydro-2H-pyran-4-yl)amino) benzoate (1.22 g, 3.824 mmol, 1 eq) in dichloroethane (15 mL) were added acetaldehyde (637.2 mg, 15.3 mmol, 4 eq) and acetic acid (1.38 g, 22.94 mmol, 6 eq) with stirring. The resulting reaction mixture was stirred at room temperature for 30 min. Then the reaction mixture was added with sodium triacetoxyborohydride (724.5 mg, 11.5 mmol, 3 eq) at 0° C., and stirred at room temperature for 2 h. After the reaction was completed, aqueous sodium bicarbonate solution was added into the reaction mixture until pH=8. The organic phase was separated and the aqueous phase was extracted with ethyl acetate. The combined organic phases were dried over anhydrous sodium sulfate, filtered, and concentrated under reduced pressure. The crude product was purified by TLC (PE:EA=5:1) to give the title compound methyl 5-cyclobutoxy-3-(ethyl(tetrahydro-2H-pyran-4-yl)amino)-2-methylbenzoate (480 mg, 36.1%) in the form of a brown oil. m/z (ES⁺), [M+H]⁺=348; HPLC $t_R$=0.851 min. 1H NMR (300 MHz, DMSO-d₆) δ 6.97-6.80 (m, 2H), 4.78-4.62 (p, J=7.2 Hz, 1H), 3.88-3.77 (s, 5H), 3.31-3.18 (t, J=10.8 Hz, 2H), 3.08-2.88 (m, 3H), 2.47-2.34 (m, 2H), 2.33-2.27 (d, J=3.8 Hz, 27H), 2.12-1.94 (m, 6H), 1.83-1.39 (m, 6H), 0.84-0.73 (t, J=7.0 Hz, 3H).

Preparation of Intermediate 1-f:

LiOH (332 mg, 13.8 mmol, 10 eq) was added to a solution of methyl 5-cyclobutoxy-3-(ethyl(tetrahydro-2H-pyran-4-yl)amino)-2-methylbenzoate (480 mg, 1.38 mmol, 1 eq) in MeOH/H$_2$O (6 mL/3 mL). The resulting suspension was stirred at 60° C. for 1 h. The solvent was removed under reduced pressure. The reaction mixture was acidified with saturated citric acid. The reaction mixture was extracted with ethyl acetate (50 mL). The organic phase was dried over Na$_2$SO$_4$, filtered and evaporated to give the crude product (483 mg, crude) in the form of a yellow oil. The product was used in the next step directly without further purification. 1H NMR (400 MHz, DMSO-d$_6$) δ 6.88-6.80 (dd, J=9.1, 2.5 Hz, 1H), 6.76-6.71 (d, J=2.5 Hz, 1H), 4.71-4.59 (p, J=7.1 Hz, 1H), 3.83-3.75 (d, J=11.6 Hz, 6H), 3.27-3.17 (t, J=11.0 Hz, 2H), 3.02-2.86 (m, 3H), 2.45-2.26 (m, 5H), 2.07-1.92 (m, 2H), 1.81-1.55 (m, 4H), 1.52-1.37 (qd, J=12.1, 4.2 Hz, 2H), 0.80-0.72 (t, J=6.9 Hz, 3H).

Preparation of Compound 1:

A solution of 3-(aminomethyl)-4,6-dimethylpyridin-2 (1H)-one (440.8 mg, 2.9 mmol, 2 eq), PyBop (2.264 g, 4.35 mmol, 3 eq), DIEA (750 mg, 5.8 mmol, 4 eq) and 5-cyclobutoxy-3-(ethyl (tetrahydro-2H-pyran-4-yl)amino)-2-methylbenzoic acid (483 mg, 1.45 mmol, 1 eq) in DMSO (5 mL) was stirred at 30° C. for 1 h. The crude product was purified by Prep-HPLC (XBridge Prep C18 OBD column, 5μ silica gel, 19 mm in diameter, 150 mm in length) using a mixture of water (containing 10 mmol NH$_4$HCO$_3$) and acetonitrile with decreasing polarity as the eluent. The fractions containing the desired compound were evaporated to dryness to give 5-cyclobutoxy-N-((4,6-dimethyl-2-oxo-1,2-dihydropyridin-3-yl)methyl)-3-(ethyl(tetrahydro-2H-pyran-4-yl)amino)-2-methylbenzamide (26.9 mg, 4%). m/z (ES+), [M+H]$^+$=468; HPLC t$_R$=1.613 min. 1H NMR (400 MHz, methanol-d$_4$) δ 6.80-6.67 (m, 1H), 6.66-6.53 (dd, J=42.6, 2.6 Hz, 1H), 6.13-6.08 (s, 1H), 4.68-4.59 (m, 1H), 4.47-4.42 (s, 2H), 3.94-3.86 (d, J=10.9 Hz, 1H), 3.39-3.33 (d, J=9.9 Hz, 2H), 3.10-2.97 (m, 3H), 2.52-2.39 (dd, J=29.8, 7.4 Hz, 2H), 2.40-2.35 (s, 3H), 2.26-2.21 (s, 3H), 2.21-2.15 (d, J=5.5 Hz, 3H), 2.13-2.03 (m, 2H), 1.87-1.77 (d, J=10.0 Hz, 1H), 1.77-1.65 (d, J=11.0 Hz, 2H), 1.65-1.54 (m, 1H), 0.88-0.80 (t, J=7.0 Hz, 3H).

Example 2: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(3-methylcyclobutoxy)benzamide (2)

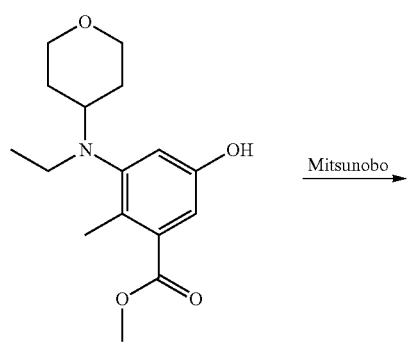

Mitsunobo →

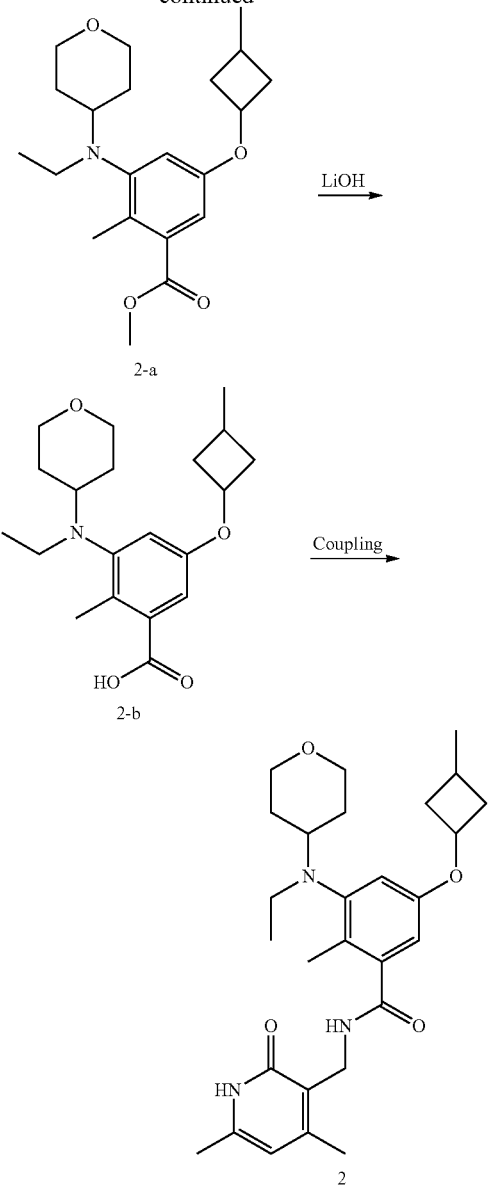

Preparation of Intermediate 2-a:

To a solution of methyl 3-(ethyl(tetrahydro-2H-pyran-4-yl)amino)-5-hydroxy-2-methylbenzoate (225 mg, 0.768 mmol, 1 eq) in THF (5 mL) were added 3-methylcyclobutan-1-ol (9.072 mg, 1.152 mmol, 1.5 eq) and PPh$_3$ (402.432 mg, 1.536 mmol, 2 eq) with stirring. After stirring for 10 min, TMAD (264.2 mg, 1.536 mmol, 2 eq) was added. The resulting reaction mixture was stirred at 60° C. for 2 h under N$_2$ atmosphere. After the reaction was completed, the reaction mixture was added with water and extracted with ethyl acetate. The combined organic phases were washed with brine, dried over anhydrous sodium sulfate, and concentrated under reduced pressure. The crude compound was purified by TLC (PE:EA=2:1) to give the title compound methyl 3-(ethyl(tetrahydro-2H-pyran-4-yl)amino)-2-methyl-5-(3-methylcyclobutoxy)benzoate (107 mg, 44.13%). m/z (ES+), [M+H]$^+$=322; HPLC t$_R$=1.466 min.

Preparation of Intermediate 2-b:

LiOH (71 mg, 2.96 mmol, 10 eq) was added to a solution of methyl 3-(ethyl(tetrahydro-2H-pyran-4-yl)amino)-2- methyl-5-(3-methylcyclobutoxy)benzoate (107 mg, 0.296 mmol, 1 eq) in MeOH/H₂O (4 mL/2 mL). The resulting suspension was stirred at 60° C. for 1 h. The reaction mixture was acidified with saturated citric acid. The reaction mixture was diluted with ethyl acetate (50 mL). The organic phase was dried over Na₂SO₄, filtered and evaporated to give the crude product (55 mg) in the form of a brown oil. The product was used in the next step without further separation. m/z (ES+), [M+H]⁺=348; HPLC $t_R$=0.724 min.

Preparation of Compound 2:

A solution of 3-(aminomethyl)-4,6-dimethylpyridin-2(1H)-one (59.6 mg, 0.318 mmol, 2 eq), PyBop (123.7 mg, 0.2385 mmol, 1.5 eq), DIEA (81.9 mg, 0.636 mmol, 4 eq) and 3-(ethyl(tetrahydro-2H-pyran-4-yl)amino)-2-methyl-5-(3-methylcyclobutoxy)benzoic acid (55 mg, 0.159 mmol, 1 eq) in DMSO (2 mL) was stirred at 30° C. for 1 h. The crude product was purified by Prep-HPLC (XBridge Prep C18 OBD column, 5μ silica gel, 19 mm in diameter, 150 mm in length) using a mixture of water (containing 10 mmol/L NH₄HCO₃+0.1% NH₃·H₂O) and MeCN with decreasing polarity as the eluent. The fractions containing the desired compound were evaporated to dryness to give N-((4,6-dimethyl-2-oxo-1,2-dihydropyridin-3-yl)methyl)-3-(ethyl(tetrahydro-2H-pyran-4-yl)amino)-2-methyl-5-(3-methylcyclobutoxy)benzamide (23.3 mg, 30.6%). m/z (ES⁺), [M+H]⁺=481; HPLC $t_R$=1.604 min. 1H NMR (400 MHz, DMSO-d₆) δ 11.55-11.43 (s, 1H), 8.08-8.00 (s, 1H), 6.65-6.58 (m, 1H), 6.45-6.39 (dd, J=11.4, 2.5 Hz, 1H), 5.90-5.83 (s, 1H), 4.87-4.77 (m, 1H), 4.28-4.21 (d, J=4.9 Hz, 2H), 3.87-3.77 (d, J=10.9 Hz, 2H), 3.28-3.17 (t, J=11.0 Hz, 2H), 3.04-2.85 (m, 3H), 2.43-2.31 (s, 1H), 2.25-2.13 (s, 4H), 2.12-1.86 (m, 8H), 1.67-1.42 (m, 5H), 1.19-1.06 (dd, J=30.5, 6.8 Hz, 3H), 0.82-0.73 (t, J=6.9 Hz, 3H).

Example 3: Preparation of the Compound 5-(3,3-difluorocyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide (3)

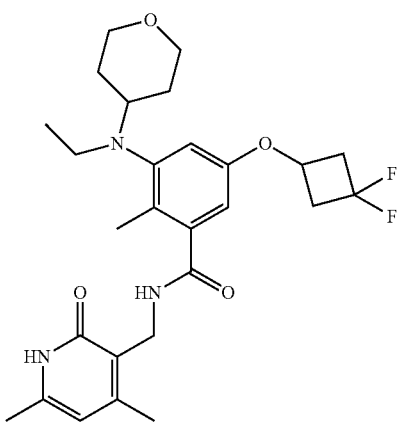 [SMILES: CCN(c1cc(OC2CC(F)(F)C2)cc(C(=O)NCc2c(C)cc(C)[nH]c2=O)c1C)C1CCOCC1]

The title compound was prepared by referring to Example 1 with cyclobutanol replaced by 3,3-difluorocyclobutanol.

m/z (ES+), [M+H]⁺=504; HPLC $t_R$=0.936 min. 1H NMR (400 MHz, DMSO-d₆) δ 11.55 11.39 (s, 1H), 8.11-8.04 (t, J=4.9 Hz, 1H), 6.72-6.66 (d, J=2.5 Hz, 1H), 6.52-6.46 (d, J=2.5 Hz, 1H), 5.89-5.84 (s, 1H), 4.81-4.71 (s, 1H), 4.29-4.22 (d, J=4.9 Hz, 2H), 3.86-3.79 (d, J=9.9 Hz, 2H), 3.29-3.24 (s, 1H), 3.24-3.08 (m, 3H), 3.05-2.92 (dd, J=16.8, 9.7 Hz, 3H), 2.74-2.57 (qd, J=14.4, 4.8 Hz, 2H), 2.23-2.18 (s, 3H), 2.14-2.09 (s, 6H), 1.65-1.57 (d, J=10.3 Hz, 2H), 1.56-1.43 (m, 2H), 0.83-0.75 (t, J=6.9 Hz, 3H). 19F NMR (376 MHz, DMSO-d6) δ −81.96-−83.28 (d, J=195.4 Hz), −92.75-−93.77 (d, J=195.4 Hz).

Example 4: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-morpholinylcyclobutoxy)benzamide (4)

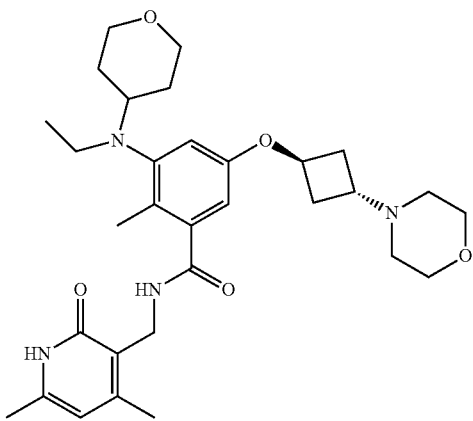 [SMILES: CCN(c1cc(O[C@H]2C[C@H](N3CCOCC3)C2)cc(C(=O)NCc2c(C)cc(C)[nH]c2=O)c1C)C1CCOCC1]

The title compound was prepared by referring to Example 1 with cyclobutanol replaced by cis-3-morpholinylcyclobutyl-1-ol. The cis-3-morpholinylcyclobutyl-1-ol was prepared as follows:

3-benzyloxy-cyclobutyl-1-one (3 g, 17 mmol, 1 eq) and morpholine (2.97 g, 34 mmol, 2 eq) were dissolved in DCE (30 mL). After stirring at room temperature for 0.5 h, the solution was added with NaBH(OAc)₃ (7.23 g, 34 mmol, 2 eq) and stirred at room temperature for 2 h. The reaction mixture was concentrated under reduced pressure to remove the solvent, adjusted to basicity with aqueous NaHCO₃ solution, and extracted with ethyl acetate. The organic phase was washed with brine, dried over anhydrous sodium sulfate, filtered, and concentrated under reduced pressure to give a crude product, which was purified by a phase preparative column to give 4-(3-(benzyloxy)cyclobutyl) morpholine (2.9 g). M/z (ES+), [M+H]⁺=248.

4-(3-(benzyloxy)cyclobutyl) morpholine (2.9 g, 117.4 mmol) and methane sulfonic acid (20 mL) was added to dichloromethane (40 mL). The mixture was stirred overnight at room temperature and concentrated under reduced pressure to remove the solvent to give a crude product, which was purified by a preparative column to give cis-3-morpholinylcyclobutyl-1-ol; m/z (ES+), [M+H]⁺=158. The trans-3-morpholinylcyclobutyl-1-ol can also be separated and obtained by this method.

m/z (ES+), [M+H]+=553; HPLC $t_R$=1.296 min. 1H NMR (400 MHz, DMSO-$d_6$) δ 11.53-11.42 (s, 1H), 8.08-8.00 (s, 1H), 6.63-6.58 (d, J=2.4 Hz, 1H), 6.44-6.38 (d, J=2.5 Hz, 1H), 5.89-5.84 (s, 1H), 4.28-4.22 (d, J=4.7 Hz, 2H), 3.63-3.57 (d, J=4.0 Hz, 4H), 3.29-3.17 (t, J=10.5 Hz, OH), 3.02-2.87 (m, 0H), 2.39-2.25 (d, J=19.9 Hz, 6H), 2.22-2.17 (s, 3H), 2.15-2.03 (d, J=2.9 Hz, 8H), 1.67-1.57 (d, J=10.7 Hz, 2H), 1.53-1.42 (d, J=8.4 Hz, 2H), 0.82-0.76 (t, J=6.9 Hz, 3H). No isomerization was found in chiral HPLC.

Example 5: Preparation of the Compound 5-cyclobutoxy-N-((4,6-dimethyl-2-oxo-1,2-dihydropyridin-3-yl)methyl)-2-methyl-3-((tetrahydro-2H-pyran-4-yl)oxy)benzamide (5)

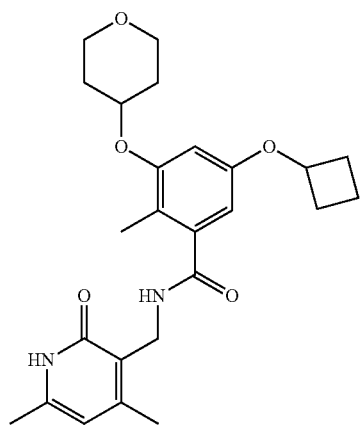 [SMILES: Cc1cc(C)c(CNC(=O)c2cc(OC3CCC3)cc(OC3CCOCC3)c2C)c(=O)[nH]1]

First the Compound 1c was prepared by referring to Example 1 and then Compound 5-b was prepared from Compound 1c, and then the title compound was prepared by referring to Example 1.

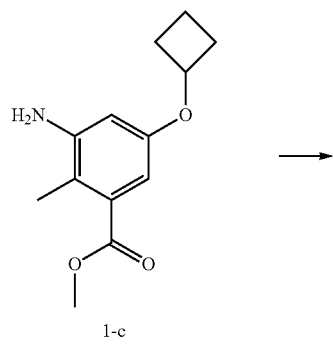

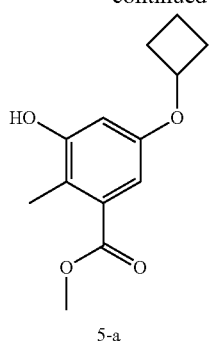 

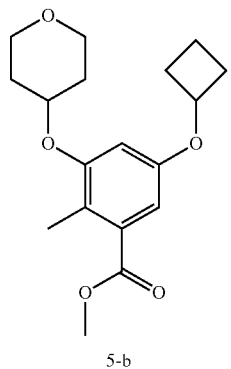

10% sulfuric acid (17.28 mL, 32.4 mmol, 6 eq) was added dropwise to a mixed solution of Compound 1c (1.27 g, 5.4 mmol, 1 eq) and methanol (12 mL). The mixture was cooled to 0° C., added with sodium nitrite (745.2 mg, 10.8 mmol) and water (17.28 mL) dropwise within 15 min, and stirred at 0° C. for 1 h. After being heated to room temperature, the mixture was added with 50% sulfuric acid solution, and then stirred for 1 h after being heated to 100° C. Then the mixture was poured into ice water and filtered. The filter cake was washed with water and dried under vacuum to give 5-a (323 mg, 25.4%) in the form of a yellow solid, m/z (ES+), [M+H]+=237; acid, HPLC $t_R$=0.89 min.

A mixed solution of Compound 5-a (323 mg, 1.37 mmol, 1 eq), 4-bromotetrahydropyran (1.348 g, 8.22 mmol, 6 eq), potassium carbonate (756.24 mg, 5.48 mmol, 4 eq) and DMF (4 mL) was heated to 100° C., and stirred for 2 h, then cooled and extracted with ethyl acetate. The organic phase was washed with aqueous sodium chloride solution, dried over anhydrous sodium sulfate, filtered, concentrated under reduced pressure, and purified by Prep-TLC to give 5-b (275 mg, 62.9%) in the form of a brown to yellow oil, m/z (ES+), base, [M+H]+=321, acid, HPLC $t_R$=1.299 min.

m/z (ES+), [M+H]+=441; HPLC $t_R$=1.338 min. 1H NMR (400 MHz, methanol-$d_4$) δ 6.54-6.49 (d, J=2.3 Hz, 1H), 6.40-6.34 (d, J=2.4 Hz, 1H), 6.15-6.10 (s, 1H), 4.72-4.51 (m, 2H), 4.49-4.44 (s, 2H), 3.99-3.89 (ddd, J=10.7, 6.5, 3.7 Hz, 2H), 3.67-3.57 (ddd, J=11.4, 7.9, 3.3 Hz, 2H), 2.50-2.36 (m, 5H), 2.29-2.24 (s, 3H), 2.17-1.96 (m, 7H), 1.91-1.64 (m, 4H).

Example 6: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(cis-3-(morpholinylmethyl)cyclobutoxy)benzamide (6)

Example 7: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(morpholinylmethyl)cyclobutoxy)benzamide (7)

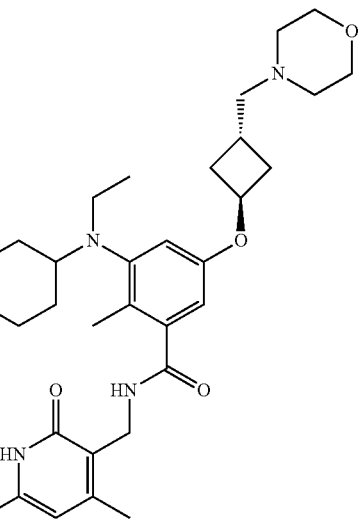

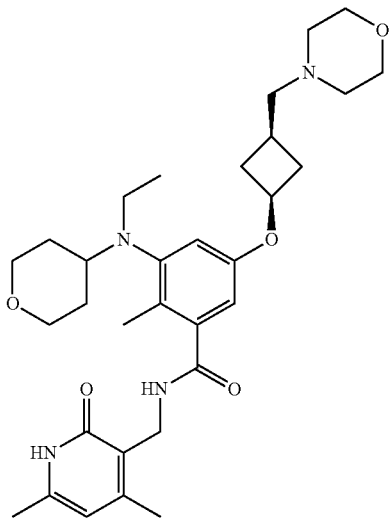 [SMILES: CCN(c1cc(O[C@H]2C[C@@H](CN3CCOCC3)C2)cc(C(=O)NCc2c(C)cc(C)[nH]c2=O)c1C)C1CCOCC1]

The title compound was prepared by referring to Example 2 and Example 4.

m/z (ES+), [M+H]$^+$=567; HPLC $t_R$=0.784 min. 1H NMR (400 MHz, methanol-$d_4$) δ 7.17-7.07 (s, 1H), 6.95-6.85 (s, 1H), 6.20-6.14 (s, 1H), 4.53-4.44 (s, 2H), 4.16-3.96 (s, 5H), 3.85-3.72 (d, J=12.5 Hz, 3H), 3.70-3.55 (s, 2H), 3.52-3.44 (s, 2H), 3.43-3.34 (d, J=7.5 Hz, 6H), 3.23-3.13 (m, 2H), 3.01-2.91 (m, 1H), 2.52-2.42 (t, J=5.2 Hz, 4H), 2.42-2.38 (s, 3H), 2.34-2.23 (d, J=13.1 Hz, 6H), 1.89-1.65 (s, 3H), 1.05-0.95 (t, J=6.9 Hz, 3H).

Example 8: Preparation of the Compound 5-(cyclobutylthio)-N-((4,6-dimethyl-2-oxo-1,2-dihydropyridin-3-yl)methyl)-3-(ethyl(tetrahydro-2H-pyran-4-yl)amino)-2-methylbenzamide (8)

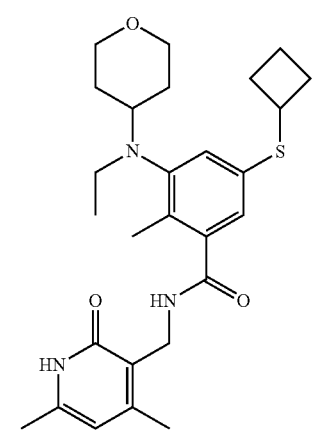 [SMILES: CCN(c1cc(SC2CCC2)cc(C(=O)NCc2c(C)cc(C)[nH]c2=O)c1C)C1CCOCC1]

The title compound was prepared by referring to Example 2 and Example 4.

m/z (ES+), [M+H]$^+$=567; HPLC $t_R$=1.650 min. 1H NMR (400 MHz, methanol-$d_4$) δ 7.13-6.95 (s, 2H), 6.18-6.13 (s, 1H), 4.51-4.46 (s, 2H), 4.17-4.04 (d, J=12.4 Hz, 4H), 3.77-3.72 (s, 2H), 3.49-3.43 (d, J=12.0 Hz, 3H), 3.26-3.11 (d, J=9.1 Hz, 2H), 3.11-2.98 (s, 1H), 2.88-2.83 (s, 1H), 2.70-2.65 (s, 11H), 2.62-2.48 (s, 2H), 2.44-2.34 (s, 4H), 2.35-2.31 (d, J=5.2 Hz, 3H), 2.29-2.21 (s, 4H), 2.11-1.83 (d, J=41.1 Hz, 3H), 1.78-1.51 (s, 3H), 1.43-1.30 (dd, J=6.7, 3.2 Hz, 2H), 1.11-0.98 (s, 3H).

The title compound was prepared from Compound 8-d by referring to Example 1. The 8-d was prepared as follows:

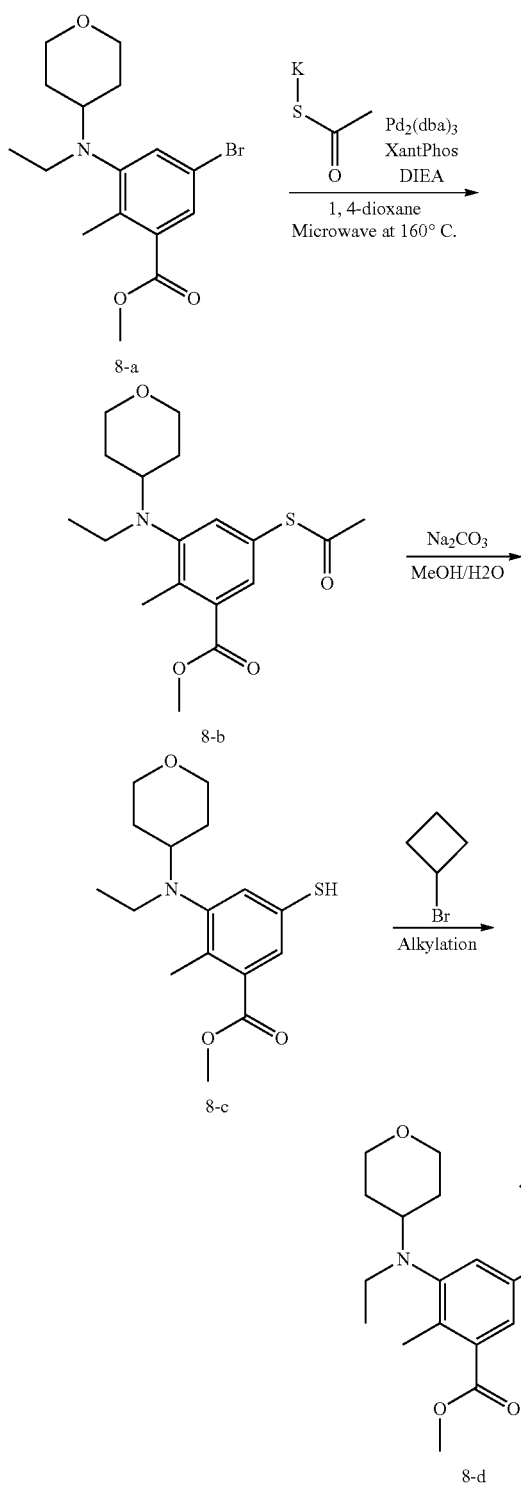

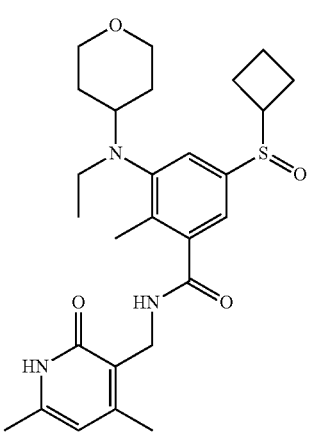 [SMILES: CCN(c1cc(S(=O)C2CCC2)cc(C(=O)NCc2c(C)cc(C)[nH]c2=O)c1C)C1CCOCC1]

To a mixed solution of Compound 8-a (3 g, 8.43 mmol, 1 eq) and 1, 4-dioxane (80 mL) was added potassium thioacetate (1.92 g, 16.86 mmol, 2 eq), Pd$_2$(dba)$_3$ (1.156 g, 1.265 mmol, 0.15 eq), Xantphos (2.4 g, 2.529 mmol, 0.3 eq), and DIEA (3.26 g, 25.29 mmol, 3 eq). The mixture was heated to 160° C. by microwave for 25 min, and filtered, and the filtrate was extracted with ethyl acetate. The organic phase was dried over anhydrous sodium sulfate, filtered, and concentrated under reduced pressure, and the residue was purified by silica gel column chromatography to give 8-b (805 mg, 27.2) in the form of a yellow oil. M/z (ES+)=352, base, HPLC tR=1.308 min. 1H NMR (400 MHz, DMSO-d6) δ 7.52-7.48 (d, J=1.7 Hz, 1H), 7.39-7.36 (d, J=1.7 Hz, 6H), 3.86-3.80 (d, J=9.7 Hz, 9H), 3.31-3.21 (t, J=10.8 Hz, 2H), 3.16-2.93 (m, 3H), 2.46-2.42 (d, J=2.4 Hz, 6H), 1.68-1.60 (d, J=10.7 Hz, 2H), 1.57-1.43 (qd, J=12.0, 4.4 Hz, 2H), 0.87-0.77 (t, J=7.0 Hz, 3H).

To a mixture of Compound 8-b (805 mg, 2.293 mmol, 1 eq) and MeOH/H$_2$O (8 mL/4 mL) was added Na$_2$CO$_3$ (486.12 mg, 4.586 mmol, 2 eq). After stirring at room temperature for 3 h, the reaction mixture was adjusted to pH=7-8 with 1M hydrochloric acid and extracted with ethyl acetate. The organic phase was concentrated under reduced pressure to give a crude product 8-c (775 mg), which was used directly in the next step. m/z (ES+), [M+H]$^+$=310; base, HPLC t$_R$=0.658 min.

To a mixture of Compound 8-c (775 mg, 2.51 mmol, 1 eq, crude), bromocyclobutane (2 g, 15.06 mmol, 6 eq) and DMF (8 mL) was added Na$_2$CO$_3$ (797 mg, 7.53 mmol, 3 eq) and the resulting mixture was heated to 70° C. and stirred for 2 h. After cooling, the mixture was extracted with ethyl acetate. The organic phases were combined, washed with water, dried, and concentrated under reduced pressure. The residue was purified by Prep-TLC to give 8-d (342 mg, 37.6%) in the form of a yellow oil. m/z (ES+), [M+Na]$^+$=386; acid, HPLC t$_R$=1.301 min. 1H NMR (400 MHz, DMSO-d$_6$) δ 7.34-7.30 (d, J=1.8 Hz, 1H), 7.22-7.17 (d, J=1.8 Hz, 1H), 4.06-3.92 (ddt, J=10.9, 7.7, 4.5 Hz, 1H), 3.85-3.80 (s, 5H), 3.31-3.21 (m, 2H), 3.09-2.89 (m, 3H), 2.47-2.34 (m, 5H), 2.03-1.88 (p, J=5.1, 4.5 Hz, 4H), 1.66-1.58 (d, J=10.9 Hz, 2H), 1.56-1.41 (qd, J=11.9, 4.3 Hz, 2H), 0.83-0.75 (t, J=7.0 Hz, 3H).

m/z (ES+), [M+H]$^+$=484; HPLC t$_R$=2.833 min. 1H NMR (400 MHz, methanol-d$_4$) δ 7.48-7.29 (s, 1H), 7.28-7.14 (s, 1H), 6.18-6.13 (s, 1H), 4.51-4.46 (s, 2H), 4.12-3.91 (d, J=10.4 Hz, 3H), 3.85-3.46 (s, 3H), 3.44-3.34 (s, 14H), 2.55-2.48 (d, J=7.3 Hz, 2H), 2.42-2.37 (s, 3H), 2.36-2.31 (s, 3H), 2.30-2.25 (s, 3H), 2.11-2.01 (m, 4H), 1.95-1.62 (s, 4H), 1.03-0.95 (t, J=6.8 Hz, 3H).

Example 9: Preparation of the Compound 5-(cyclobutylsulfinyl)-N-((4,6-dimethyl-2-oxo-1,2-dihydropyridin-3-yl)methyl)-3-(ethyl(tetrahydro-2H-pyran-4-yl)amino)-2-methylbenzamide (9)

To a mixed solution of Compound 8 (100 mg, 0.207 mmol, 1 eq) and DCM/TEA (6:1, 2 mL) was added NCS (221.2 mg, 0.828 mmol, 4 eq). The mixture was stirred at room temperature for 5 h, and concentrated under reduced pressure. The residue was separated and purified by Prep-HPLC (XBridge Prep C18 OBD column, 5μ silica gel, 19 mm in diameter, 150 mm in length) to give the target compound (0.72 mg, 0.7%) in the form of a yellow oil.

m/z (ES+), [M+H]$^+$=500; HPLC $t_R$=0.933 min. 1H NMR (400 MHz, methanol-$d_4$) δ 7.62-7.55 (s, 1H), 7.36-7.28 (s, 1H), 6.22-6.12 (s, 1H), 4.52-4.47 (s, 2H), 3.99-3.92 (d, J=11.0 Hz, 2H), 3.77-3.68 (p, J=8.3 Hz, 1H), 3.41-3.36 (m, 0H), 3.30-3.19 (d, J=6.9 Hz, 3H), 2.48-2.35 (m, 0H), 2.29-2.23 (s, 0H), 2.08-1.88 (m, 3H), 1.79-1.65 (dd, J=12.1, 8.7 Hz, 5H), 0.94-0.85 (t, J=7.0 Hz, 3H).

Example 10: Preparation of the Compound 5-(cyclobutylsulfonyl)-N-((4,6-dimethyl-2-oxo-1,2-dihydropyridin-3-yl)methyl)-3-(ethyl(tetrahydro-2H-pyran-4-yl)amino)-2-methylbenzamide (10)

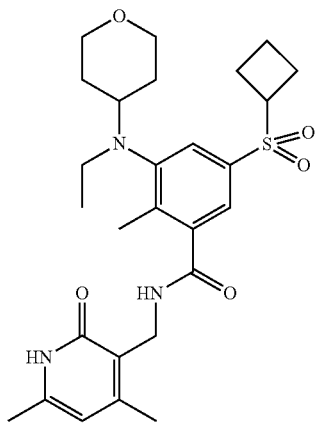 [SMILES: CCN(c1cc(S(=O)(=O)C2CCC2)cc(C(=O)NCc2c(C)cc(C)[nH]c2=O)c1C)C1CCOCC1]

To a mixed solution of Compound 8 (50 mg, 0.104 mmol, 1 eq) and MeOH/H$_2$O (1 mL/0.5 mL) was added potassium peroxymonosulfate (127.3 mg, 0.208 mmol, 2 eq). After stirring at room temperature for 2 h, the mixture was added with aqueous NaHSO$_3$ solution and extracted with ethyl acetate (50 mL×3). The organic phase was concentrated under reduced pressure, and the residue was separated and purified by Prep-HPLC (XBridge Prep C18 OBD column, 5μ silica gel, 19 mm in diameter and 150 mm in length) to give the title compound (10.4 mg, 19.5%) in the form of a white solid.

m/z (ES+), [M+H]$^+$=516; HPLC $t_R$=2.650 min. 1H NMR (400 MHz, DMSO-$d_6$) δ 11.55-11.50 (s, 1H), 8.43-8.38 (s, 1H), 7.54-7.49 (s, 1H), 7.37-7.32 (s, 1H), 5.91-5.86 (s, 1H), 4.33-4.26 (d, J=4.8 Hz, 2H), 4.16-4.09 (m, 1H), 3.89-3.80 (d, J=11.6 Hz, 0H), 3.31-3.24 (d, J=9.3 Hz, 2H), 3.12-2.97 (m, 0H), 2.37-2.26 (m, 0H), 2.24-2.19 (s, 3H), 2.15-2.04 (s, 0H), 1.96-1.83 (dd, J=14.9, 6.8 Hz, 0H), 1.66-1.49 (s, 4H), 0.84-0.76 (t, J=6.9 Hz, 3H).

Example 11: Preparation of the Compound 2-chloro-5-cyclobutoxy-N-((4,6-dimethyl-2-oxo-1,2-dihydropyridin-3-yl)methyl)-3-(ethyl(tetrahydro-2H-pyran-4-yl)amino) benzamide (11)

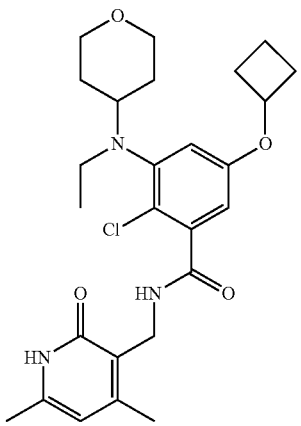

The title compound was prepared by referring to Example 2.

m/z (ES+), [M+H]$^+$=487; HPLC $t_R$=1.32 min. 1H NMR (400 MHz, DMSO-$d_6$) δ11.62-11.36 (s, 1H), 8.41-8.12 (t, J=8 Hz, 1H), 6.87-6.62 (d, J=4 Hz, 1H), 6.59-6.40 (d, J=4 Hz, 1H), 6.01-5.81 (s, 1H), 4.88-4.61 (p, J=9.5 Hz, 1H), 4.40-4.16 (d, J=4 Hz, 2H), 4.01-3.74 (d, J=6.3 Hz, 2H), 3.32-3.20 (t, J=8.5 Hz, 2H), 3.20-2.97 (m, J=7.6 Hz, 3H), 2.45-2.30 (m, J=5.2 Hz, 2H), 2.28-2.17 (s, 3H), 2.16-2.08 (s, 3H), 2.07-1.93 (m, J=5.8 Hz, 2H), 1.83-1.70 (q, J=6.7 Hz 1H), 1.69-1.47 (m, J=9.7 Hz, 5H), 0.91-0.74 (t, J=7.5 Hz, 3H).

Example 12: Preparation of the Compound N-((4,6-dimethyl-2-oxo-1,2-dihydropyridin-3-yl)methyl)-5-(3,3-dimethylcyclobutoxy)-3-(ethyl(tetrahydro-2H-pyran-4-yl)amino)-2-methylbenzamide (12)

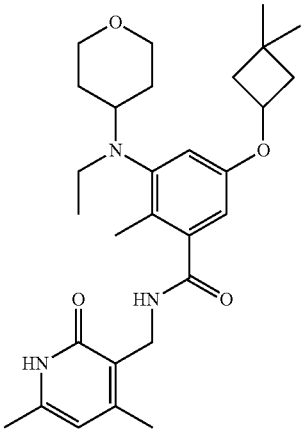

The title compound was prepared by referring to Example 2.

m/z (ES+), [M+H]$^+$=496; HPLC $t_R$=1.679 min. 1H NMR (400 MHz, DMSO-$d_6$) δ 11.49-11.44 (s, 1H), 8.07-7.99 (t, J=4.9 Hz, 1H), 6.63-6.57 (d, J=2.4 Hz, 1H), 6.44-6.39 (d, J=2.4 Hz, 1H), 5.89-5.84 (s, 1H), 4.73-4.65 (m, 1H), 4.28-4.22 (d, J=4.9 Hz, 2H), 3.87-3.78 (d, J=10.9 Hz, 2H), 3.29-3.18 (t, J=11.0 Hz, 2H), 3.03-2.88 (m, 3H), 2.57-2.53 (s, 13H), 2.30-2.17 (m, 5H), 2.14-2.07 (d, J=6.2 Hz, 6H), 1.85-1.75 (m, 2H), 1.62-1.57 (s, 2H), 1.53-1.46 (d, J=8.4 Hz, 2H), 1.19-1.11 (d, J=13.1 Hz, 6H), 0.83-0.74 (t, J=6.9 Hz, 3H).

Example 13: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(3-(morpholine-4-carbonyl)cyclobutoxy)benzamide (13)

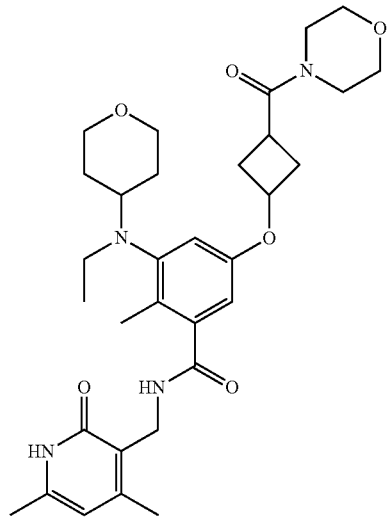 [SMILES: CCN(c1cc(OC2CC(C(=O)N3CCOCC3)C2)cc(C(=O)NCc2c(C)cc(C)[nH]c2=O)c1C)C1CCOCC1]

By referring to Example 2, the Compound 13-c was prepared first and the title compound was then prepared. The 13-c was prepared as follows:

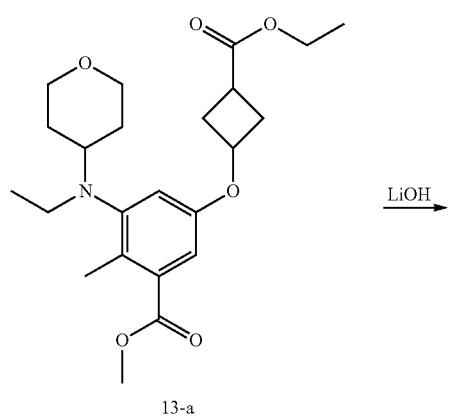

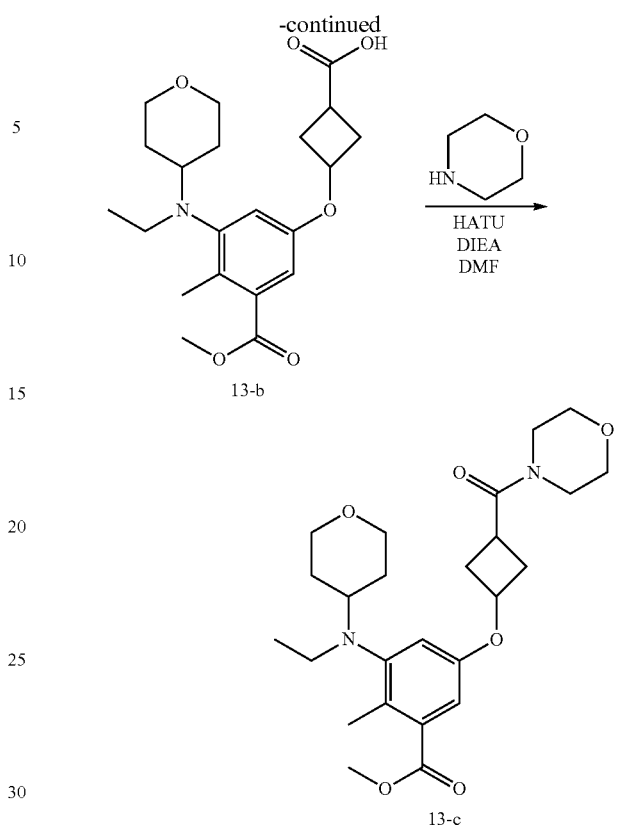

Lithium hydroxide (74.5 mg, 0.62 mmol, 2 eq) was added to a solution of Compound 13-a (130 mg, 0.31 mmol, 1 eq) and MeOH/H$_2$O (4 mL/2 mL). After reacting at 0° C. for 2 h, the reaction mixture was neutralized with 1M hydrochloric acid and added with ethyl acetate (50 mL). The organic phase was dried over anhydrous sodium sulfate and concentrated under reduced pressure, and the residue was purified by C-18 flash column chromatography to give 13-b (100 mg, 82.4%) in the form of a white solid. 1H NMR (400 MHz, DMSO-d$_6$) δ 6.89-6.79 (dd, J=20.2, 2.6 Hz, 2H), 4.88-4.77 (p, J=6.5 Hz, 1H), 3.86-3.79 (s, 4H), 3.29-3.20 (t, J=10.9 Hz, 4H), 3.13-2.89 (dtt, J=23.3, 16.2, 7.9 Hz, 5H), 2.67-2.56 (ddt, J=11.1, 7.0, 4.1 Hz, 2H), 2.38-2.26 (m, 4H), 1.65-1.58 (d, J=11.0 Hz, 2H), 1.55-1.40 (qd, J=12.2, 4.5 Hz, 2H), 1.31-1.19 (d, J=9.8 Hz, 2H), 0.82-0.74 (t, J=7.0 Hz, 3H).

To a solution of compound 13-b (100 mg, 0.256 mmol, 1 eq) and DMF (5 mL) were added morpholine (44.5 mg, 0.512 mmol, 2 eq), HATU (145.9 mg, 0.384 mmol, 1.5 eq), and DIEA (99.2 mg, 0.768 mmol, 3 eq). The mixture was stirred at room temperature for 2 h, and extracted with ethyl acetate (50 mL×3). The organic phases were combined, dried over anhydrous ammonium sulfate, filtered, and concentrated under reduced pressure, and the residue was separated by Prep-TLC to give Compound 13-c (73 mg, 85%) in the form of a yellow oil. m/z (ES+), [M+H]$^+$=461; acid, HPLC t$_R$=0.811 min.

m/z (ES+), [M+H]$^+$=581; HPLC t$_R$=0.85 min. 1H NMR (400 MHz, DMSO-d6) δ 11.50-11.45 (s, 1H), 8.08-8.01 (d, J=5.0 Hz, 1H), 6.63-6.58 (d, J=2.4 Hz, 1H), 6.42-6.37 (d, J=2.4 Hz, 1H), 5.89-5.84 (s, 1H), 4.69-4.63 (d, J=5.7 Hz, 1H), 4.29-4.23 (d, J=4.9 Hz, 2H), 3.87-3.78 (d, J=10.7 Hz, 2H), 3.59-3.50 (m, 4H), 3.51-3.45 (d, J=4.8 Hz, 2H), 3.44-3.37 (d, J=4.9 Hz, 2H), 3.28-3.19 (t, J=10.7 Hz, 2H), 3.02-2.88 (m, 0H), 2.69-2.59 (d, J=25.2 Hz, 2H), 2.35-2.24 (d, J=25.6 Hz, 2H), 2.22-2.17 (s, 3H), 2.14-2.05 (d, J=4.1 Hz, 0H), 1.65-1.57 (d, J=11.7 Hz, 2H), 1.56-1.44 (d, J=8.2 Hz, 2H), 0.83-0.75 (t, J=7.0 Hz, 3H).

Example 14: Preparation of the Compound 5-cyclopropyl-N-((4,6-dimethyl-2-oxo-1,2-dihydropyridin-3-yl)methyl)-3-(ethyl(tetrahydro-2H-pyran-4-yl)amino)-2-methylbenzamide (14)

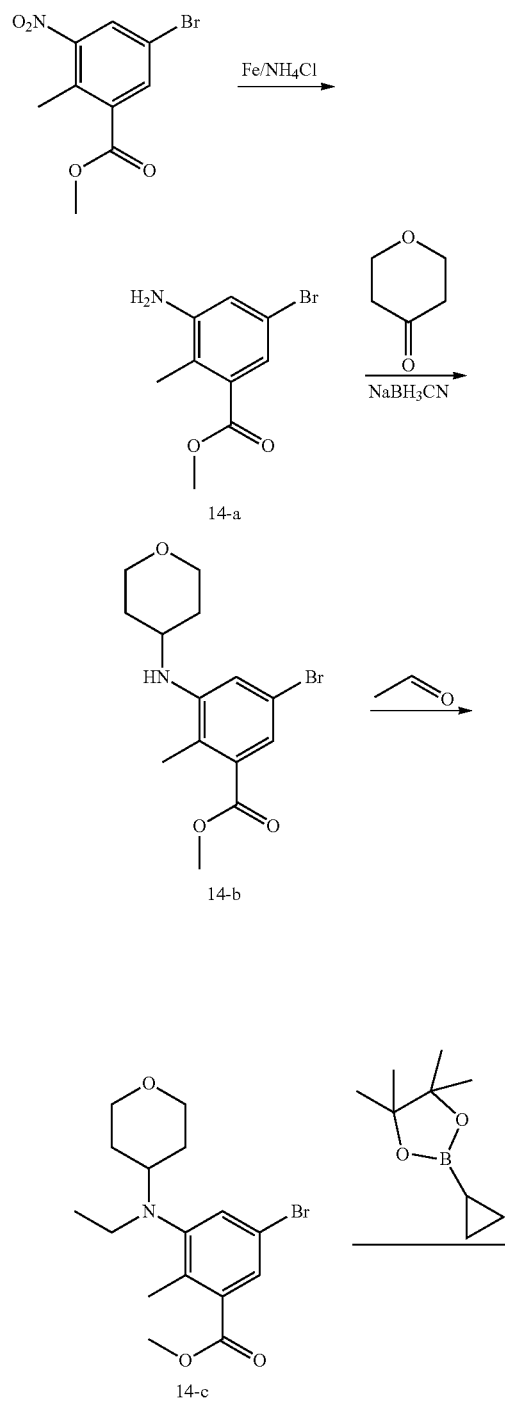

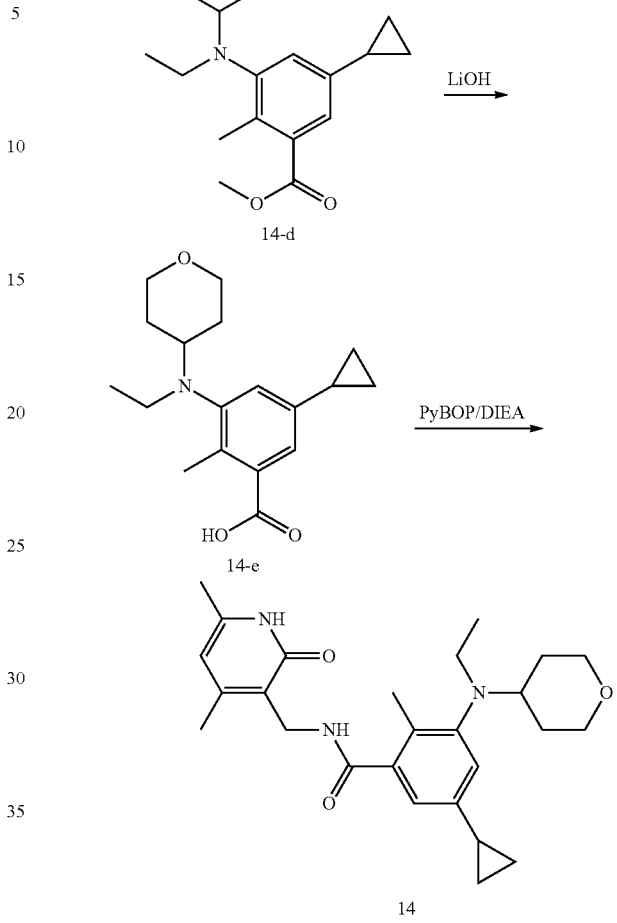

Preparation of Intermediate 14-a:
To a solution of methyl 5-bromo-2-methyl-3-nitrobenzoate (10 g, 36.5 mmol) in MeOH/H$_2$O (50 mL) were added iron powder (10 g, 180 mmol) and ammonium chloride (2 g, 72 mmol) at 20° C. The mixture was stirred at 100° C. for 12 h. The mixture was filtered, concentrated, and extracted with ethyl acetate (100 mL×3). The organic phase was washed with brine, dried over Na$_2$SO$_4$, and concentrated. The crude product was purified by silica gel chromatography (PE/EA=3/1) to give methyl 3-amino-5-bromo-2-methylbenzoate (4.4 g, 49.4%) in the form of a yellow oil. m/z (ES+), [M+H]$^+$=244,246; HPLC t$_R$=1.116 min.

Preparation of Intermediate 14-b:
To a stirred solution of methyl 3-amino-5-bromo-2-methylbenzoate (4.4 g, 18 mmol) in MeOH (100 mL) was added acetic acid (11 g, 180 mmol) and tetrahydro-4H-pyran-4-one (7.2 g, 72 mmol) successively at 0° C. The mixture was stirred at 20° C. for 3 h. Sodium cyanoborohydride (5.7 g, 90 mmol) was then added at 0° C. After stirring for 12 h, the mixture was concentrated, then basified with saturated sodium bicarbonate solution to pH=8 and extracted with ethyl acetate (100 mL×3). The organic phase was washed with brine, dried over Na$_2$SO$_4$, and concentrated to give the crude product. The crude product was purified by silica gel chromatography (PE/EA=2/1) to give methyl 5-bromo-2-methyl-3-((tetrahydro-2H-pyran-4-yl)amino)benzoate (2.4 g, 40.5%) in the form of a yellow oil. m/z (ES+), [M+H]+ =328,330; HPLC $t_R$=1.148 min.

Preparation of Intermediate 14-c:

To a solution of methyl 5-bromo-2-methyl-3-((tetrahydro-2H-pyran-4-yl)amino) benzoate (2.4 g, 7.3 mmol) in 1,2-dichloroethane (100 mL) were added acetic acid (2.7 g, 44 mmol) and acetaldehyde (1.3 g, 30 mmol) successively at 0° C. The mixture was stirred at 20° C. for 0.5 h, and then sodium triacetoxyborohydride (4.7 g, 24 mmol) was added at 0° C. After stirring for 12 h, the mixture was concentrated, then basified with saturated sodium bicarbonate to pH=8 and extracted with ethyl acetate (50 mL×3). The organic phase was washed with brine, dried over $Na_2SO_4$, and concentrated to give the crude product. The crude product was purified by silica gel chromatography (PE/EA=2/1) to give methyl 5-bromo-3-(ethyl(tetrahydro-2H-pyran-4-yl)amino)-2-methylbenzoate (2.3 g, 88.2%) in the form of a yellow oil. m/z (ES+), [M+H]+=356,358; acid, HPLC $t_R$=1.331 min.

Preparation of Intermediate 14-d:

To a solution of methyl 5-bromo-3-(ethyl(tetrahydro-2H-pyran-4-yl)amino)-2-methylbenzoate (250 mg, 0.7 mmol) in 1,4-dioxane/$H_2O$ (4/1) (20 mL) were added $Cs_2CO_3$ (460 mg, 1.4 mmol), Pd(dppf)$Cl_2$ (20 mg), and 2-cyclopropyl-4,4,5,5-tetramethyl-1,3,2-dioxaborolane (180 mg, 1.05 mmol) successively at 20° C. The mixture was stirred at 80° C. for 8 h. The mixture was filtered, and extracted with ethyl acetate (50 mL×3). The organic phase was washed with brine, dried over $Na_2SO_4$, concentrated, and purified by silica gel chromatography (PE/EA=5/1) to give the product methyl 5-cyclopropyl-3-(ethyl(tetrahydro-2H-pyran-4-yl) amino)-2-methylbenzoate (100 mg, 44.9%) in the form of a yellow oil. m/z (ES+), [M+H]+=318; HPLC $t_R$=0.944 min.

Preparation of Intermediate 14-e:

To a solution of methyl 5-cyclopropyl-3-(ethyl(tetrahydro-2H-pyran-4-yl)amino)-2-methylbenzoate (100 mg, 0.3 mmol) in THF/$H_2O$ (4/1) (50 mL) was added LiOH (80 mg, 3 mmol) at 20° C. The mixture was stirred at 20° C. for 6 h. The mixture was then acidified with citric acid to pH=5 at 0° C., and extracted with ethyl acetate (20 mL×3). The organic phase was washed with brine, dried over $Na_2SO_4$, concentrated, and purified by Prep-HPLC (column: XSelect CSH OBD column 30×150 mm 5 um n; mobile phase A: water (0.05% TFA), mobile phase B: ACN; flow rate: 60 mL/min; gradient: 12% B to 22% B over 7 min; 254; 220 nm; Rt: 6.37 min) to give the compound 5-cyclopropyl-3-(ethyl(tetrahydro-2H-pyran-4-yl)amino)-2-methylbenzoic acid (90 mg, 94%) in the form of a colorless solid. m/z (ES+), [M+H]+=304; HPLC $t_R$=0.794 min.

Preparation of Compound 14:

To a solution of 5-cyclopropyl-3-(ethyl(tetrahydro-2H-pyran-4-yl)amino)-2-methylbenzoic acid (90 mg, 0.3 mmol) in DMSO (20 mL) were added 3-(aminomethyl)-4,6-dimethylpyridin-2 (1H)-one hydrochloride (120 mg, 0.6 mmol), PyBop (470 mg, 0.9 mmol), and DIEA (200 mg, 1.5 mmol) successively at 20° C. The mixture was stirred at 20° C. for 6 h. The mixture was then added with water and extracted with ethyl acetate (10 mL×3). The organic phase was washed with brine, dried over $Na_2SO_4$, and concentrated. The crude product was purified by Prep-HPLC (column: XBridge Prep OBD C18 column 30×150 mm 5 um; mobile phase A: water (10 mmol/L $NH_4HCO_3$+0.1% $NH_3 \cdot H_2O$), mobile phase B: ACN; flow rate: 60 mL/min; gradient: 25% B to 54% B over 8 min; 254/220 nm; Rt: 7.40 min) to give 5-cyclopropyl-N-((4,6-dimethyl-2-oxo-1,2-dihydropyridin-3-yl)methyl)-3-(ethyl(tetrahydro-2H-pyran-4-yl)amino)-2-methylbenzamide (36 mg, 27.7% mg, 94%). m/z (ES+), [M+H]+=438; HPLC $t_R$=1.928 min. 1H NMR (300 MHz, methanol-$d_4$) δ 6.98 (d, J=1.9 Hz, 1H), 6.74 (d, J=1.8 Hz, 1H), 6.11 (s, 1H), 4.45 (s, 2H), 3.90 (d, J=11.5 Hz, 2H), 3.46-3.30 (m, 2H), 3.13-2.92 (m, 3H), 2.37 (s, 3H), 2.23 (d, J=7.1 Hz, 6H), 1.85 (ddd, J=13.5, 8.6, 5.1 Hz, 1H), 1.75-1.48 (m, 4H), 0.99-0.86 (m, 2H), 0.83 (t, J=7.0 Hz, 3H), 0.68-0.56 (m, 2H).

Example 15: Preparation of the Compound 5-cyclobutyl-N-((4,6-dimethyl-2-oxo-1,2-dihydropyridin-3-yl)methyl)-3-(ethyl(tetrahydro-2H-pyran-4-yl) amino)-2-methylbenzamide (15)

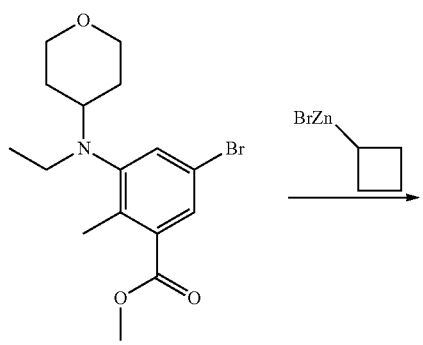

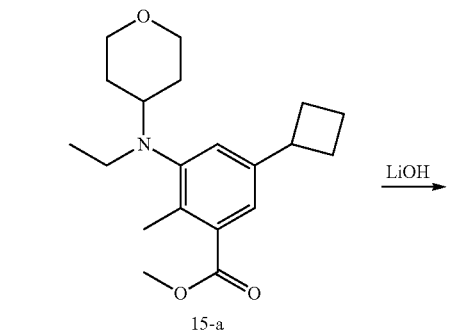

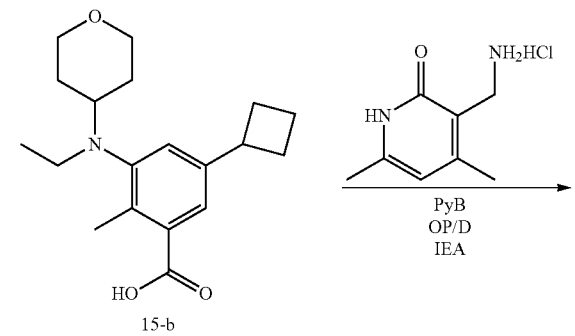

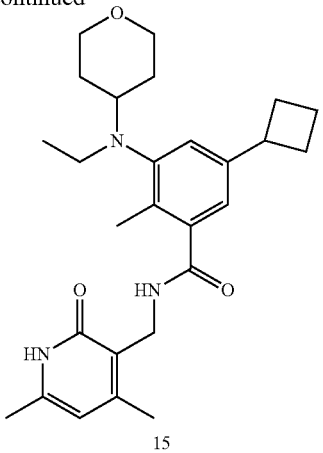

15

Preparation of Intermediate 15-a:

To a stirred solution of methyl 5-bromo-3-(ethyl(tetrahydro-2H-pyran-4-yl)amino)-2-methylbenzoate (300 mg, 0.85 mmol) in THF (50 mL) were added $Pd_2(dba)_3$ (50 mg) and x-phos (50 mg) at 20° C., followed by addition of cyclobutylzinc (II) bromide (900 mg, 4.5 mmol) at 0° C. under $N_2$ atmosphere. The mixture was stirred at 70° C. for 8 h. A saturated solution of $NH_4Cl$ was added and the mixture was filtered. The filtrate was extracted with ethyl acetate (50 mL×3). The organic layer was washed with brine, dried over $Na_2SO_4$, and concentrated. The crude product was purified by silica gel chromatography (PE/EA=3/1) to give methyl 5-cyclobutyl-3-(ethyl(tetrahydro-2H-pyran-4-yl)amino)-2-methylbenzoate (272 mg, 97%). m/z (ES+), [M+H]$^+$=332; HPLC $t_R$=1.012 min.

Preparation of Intermediate 15-b:

To a solution of methyl 5-cyclobutyl-3-(ethyl(tetrahydro-2H-pyran-4-yl)amino)-2-methylbenzoate (272 mg, 0.82 mmol) in THF/$H_2O$ (4/1) (25 mL) was added LiOH (200 mg, 8.2 mmol) at 20° C. The mixture was stirred at 20° C. for 6 h. The mixture was then acidified to pH=5 with 1M HCl at 0° C., and extracted with ethyl acetate (20 mL×3). The organic phase was washed with brine, dried over $Na_2SO_4$, and concentrated to give 5-cyclobutyl-3-(ethyl(tetrahydro-2H-pyran-4-yl)amino)-2-methylbenzoic acid (176 mg, 67.5%) in the form of a yellow solid. m/z (ES+), [M+H]$^+$=318; HPLC $t_R$=0.867 min.

Preparation of Compound 15:

To a solution of 5-cyclobutyl-3-(ethyl(tetrahydro-2H-pyran-4-yl)amino)-2-methylbenzoic acid (176 mg, 0.55 mmol) in DMSO (50 mL) were added 3-(aminomethyl)-4,6-dimethylpyridin-2 (1H)-one hydrochloride (210 mg, 1.1 mmol), PyBop (870 mg, 1.6 mmol), and DIEA (360 mg, 2.8 mmol) successively at 20° C. The mixture was stirred at 20° C. for 6 h. The mixture was then added with water and extracted with ethyl acetate (20 mL×3). The organic phase was washed with brine, dried over $Na_2SO_4$, and concentrated. The crude product was purified by Prep-HPLC (column: XBridge Prep OBD C18 column 30×150 mm 5 um; mobile phase A: water (10 mmol/L $NH_4HCO_3$+0.1% $NH_3·H_2O$), mobile phase B: ACN; flow rate: 60 mL/min; 254/220 nm; Rt: 7.53 min) to give 5-cyclobutyl-N-((4,6-dimethyl-2-oxo-1,2-dihydropyridin-3-yl)methyl)-3-(ethyl(tetrahydro-2H-pyran-4-yl)amino)-2-methylbenzamide (101.2 mg, 40%). m/z (ES+), [M+H]$^+$=452; HPLC $t_R$=2.184 min. 1H NMR (300 MHz, methanol-$d_4$) δ 7.08 (s, 1H), 6.93 (d, J=1.8 Hz, 1H), 6.11 (s, 1H), 4.46 (s, 2H), 3.90 (d, J=11.4 Hz, 2H), 3.49 (d, J=8.6 Hz, 1H), 3.40-3.32 (m, 2H), 3.16-2.94 (m, 3H), 2.38 (s, 3H), 2.36-2.14 (m, 8H), 2.14-1.95 (m, 3H), 1.85 (t, J=7.7 Hz, 1H), 1.74-1.51 (m, 4H), 0.83 (t, J=7.0 Hz, 3H).

Example 16: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(3-(morpholinylmethyl)cyclobutoxy)benzamide (16)

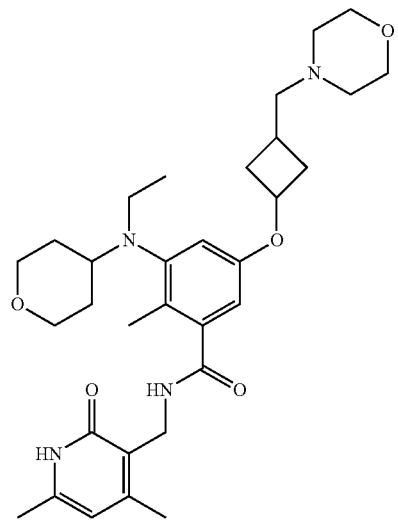 [SMILES: CCN(c1cc(OC2CC(CN3CCOCC3)C2)cc(C(=O)NCc2c(C)cc(C)[nH]c2=O)c1C)C1CCOCC1]

The title compound was prepared by referring to Example 2 and Example 4.

m/z (ES+), [M+H]$^+$=567; HPLC $t_R$=1.042 min. 1H NMR (400 MHz, methanol-$d_4$) δ 6.85-6.79 (d, J=2.5 Hz, 1H), 6.74-6.64 (m, 3H), 6.60-6.50 (dd, J=16.5, 2.6 Hz, 2H), 6.16-6.11 (s, 2H), 4.80-4.72 (m, 2H), 4.50-4.45 (s, 4H), 3.97-3.89 (m, 5H), 3.75-3.68 (m, 8H), 3.41-3.34 (d, J=10.2 Hz, 5H), 3.12-2.99 (m, 6H), 2.70-2.63 (d, J=7.1 Hz, 2H), 2.61-2.48 (m, 8H), 2.42-2.37 (s, 7H), 2.32-2.24 (d, J=4.5 Hz, 11H), 2.24-2.17 (d, J=5.5 Hz, 6H), 1.84-1.72 (dd, J=21.1, 8.8 Hz, 5H), 1.74-1.59 (m, 8H), 0.91-0.82 (m, 7H).

Example 17: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(cis-3-(piperazin-1-yl)cyclobutoxy)benzamide (17)

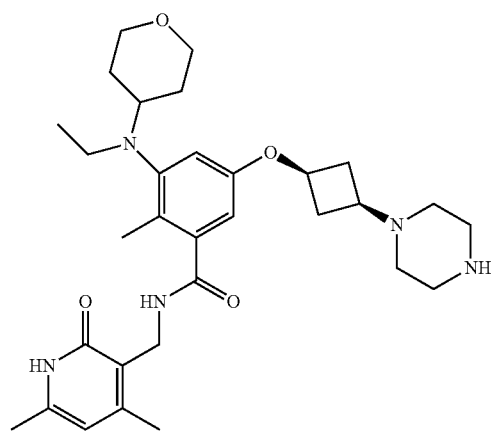 [SMILES: CCN(c1cc(O[C@H]2C[C@@H](N3CCNCC3)C2)cc(C(=O)NCc2c(C)cc(C)[nH]c2=O)c1C)C1CCOCC1]

The title compound was prepared by referring to Example 2 and Example 4.

m/z (ES+); [M+H]$^+$=552; HPLC $t_R$=1.246 min. 1H NMR (300 MHz, methanol-$d_4$) δ 6.73-6.69 (d, J=2.4 Hz, 1H), 6.55-6.51 (d, J=2.4 Hz, 1H), 6.16-6.10 (s, 1H), 4.81-4.69 (m, 1H), 4.50-4.44 (s, 2H), 3.99-3.88 (d, J=11.1 Hz, 2H), 3.42-3.35 (s, 30H), 3.14-2.99 (dd, J=11.8, 7.4 Hz, 4H), 2.98-2.88 (t, J=4.8 Hz, 4H), 2.55-2.23 (d, J=40.1 Hz, 14H), 2.23-2.18 (s, 3H), 1.78-1.58 (m, 3H), 0.91-0.83 (t, J=7.0 Hz, 3H).

Example 18: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(piperazin-1-yl)cyclobutoxy)benzamide (18)

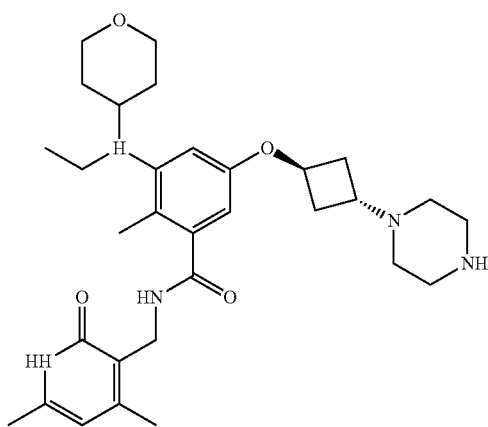

The title compound was prepared by referring to Example 2 and Example 4.

m/z (ES+), [M+H]$^+$=552; HPLC $t_R$=1.221 min. 1H NMR (300 MHz, methanol-$d_4$) δ 6.77-6.70 (d, J=2.5 Hz, 1H), 6.62-6.55 (d, J=2.5 Hz, 1H), 6.16-6.10 (s, 1H), 4.53-4.42 (d, J=4.8 Hz, 3H), 3.98-3.88 (d, J=11.7 Hz, 2H), 3.42-3.35 (d, J=12.0 Hz, 2H), 3.14-2.99 (dt, J=12.2, 6.0 Hz, 3H), 2.95-2.85 (t, J=4.8 Hz, 4H), 2.77-2.65 (m, 2H), 2.61-2.50 (m, 1H), 2.46-2.36 (s, 4H), 2.30-2.17 (d, J=18.7 Hz, 6H), 2.04-1.89 (q, J=8.4 Hz, 2H), 1.78-1.56 (m, 1H), 0.92-0.81 (t, J=7.0 Hz, 3H).

Example 19: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperazin-1-yl)cyclobutoxy)benzamide (19)

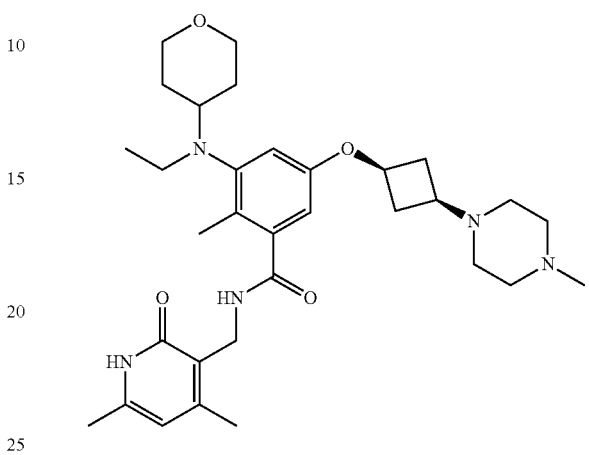

The title compound was prepared by referring to Example 2 and Example 4.

m/z (ES+), [M+H]$^+$=566; HPLC $t_R$=1.238 min. 1H NMR (400 MHz, methanol-$d_4$) δ 6.74-6.68 (d, J=2.5 Hz, 1H), 6.55-6.50 (d, J=2.5 Hz, 1H), 6.15-6.10 (s, 1H), 4.78-4.73 (s, 1H), 4.50-4.45 (s, 2H), 3.41-3.35 (d, J=11.7 Hz, 2H), 3.13-3.00 (m, 4H), 2.46-2.15 (m, 18H), 1.75-1.58 (m, 4H), 0.91-0.83 (t, J=7.0 Hz, 3H).

Example 20: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperazin-1-yl)cyclobutoxy)benzamide (20)

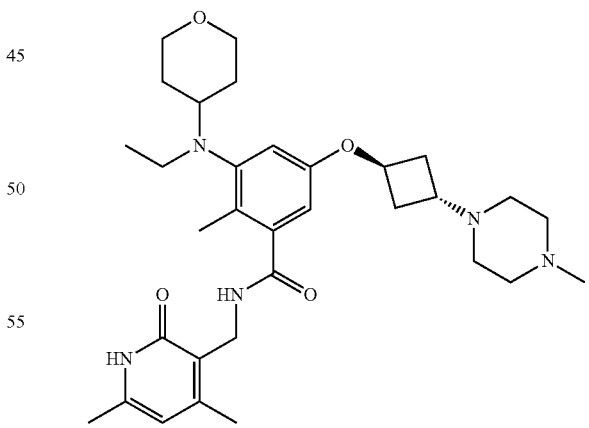

The title compound was prepared by referring to Example 2 and Example 4.

m/z (ES+), [M+H]$^+$=566; HPLC $t_R$=1.213 min. 1H NMR (400 MHz, methanol-d4) δ 6.76-6.71 (s, 1H), 6.61-6.56 (s, 1H), 6.15-6.10 (s, 1H), 4.65-4.57 (s, 2H), 4.55-4.30 (s, 2H), 3.97-3.89 (d, J=11.0 Hz, 2H), 3.41-3.35 (d, J=12.0 Hz, 3H), 3.14-2.97 (m, 4H), 2.77-2.65 (d, J=6.5 Hz, 3H), 2.61-2.52

(m, 2H), 2.43-2.38 (s, 3H), 2.35-2.30 (s, 3H), 2.28-2.24 (s, 3H), 2.22-2.17 (s, 3H), 2.04-1.93 (d, J=9.4 Hz, 2H), 1.75-1.55 (m, 4H), 1.37-1.25 (s, 1H), 0.91-0.82 (t, J=6.9 Hz, 3H).

Example 21: Preparation of the Compound N-((4,6-dimethyl-2-oxo-1,2-dihydropyridin-3-yl)methyl)-3-(ethyl(tetrahydro-2H-pyran-4-yl)amino)-5-(cis-3-(4-isopropylpiperazin-1-yl)cyclobutoxy)-2-methylbenzamide (21)

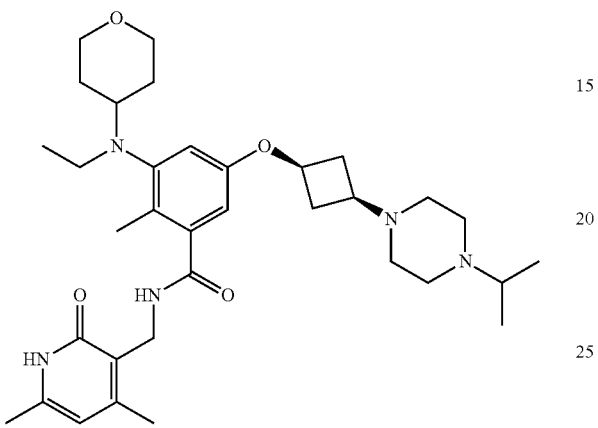

The title compound was prepared by referring to Example 2 and Example 4.

m/z (ES+), [M+H]$^+$=594; HPLC $t_R$=1.388 min. 1H NMR (300 MHz, methanol-$d_4$) δ 6.73-6.70 (d, J=2.5 Hz, 1H), 6.55-6.51 (d, J=2.5 Hz, 1H), 6.15-6.11 (s, 1H), 4.82-4.72 (m, 1H), 4.50-4.44 (s, 2H), 3.98-3.87 (d, J=11.2 Hz, 1H), 3.42-3.35 (s, 2H), 3.14-3.01 (q, J=6.9 Hz, 4H), 2.92-2.53 (s, 7H), 2.51-2.34 (s, 3H), 2.33-2.17 (d, J=18.5 Hz, 8H), 1.78-1.68 (d, J=10.3 Hz, 1H), 1.67-1.56 (d, J=8.5 Hz, 1H), 1.17-1.08 (d, J=6.5 Hz, 6H), 0.91-0.81 (t, J=7.0 Hz, 3H).

Example 22: Preparation of the Compound N-((4,6-dimethyl-2-oxo-1,2-dihydropyridin-3-yl)methyl)-3-(ethyl(tetrahydro-2H-pyran-4-yl)amino)-5-(trans-3-(4-isopropylpiperazin-1-yl)cyclobutoxy)-2-methylbenzamide (22)

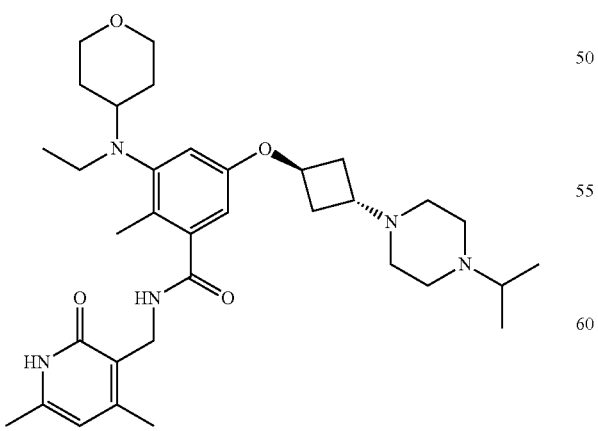

The title compound was prepared by referring to Example 2 and Example 4.

m/z (ES+), [M+H]$^+$=594; HPLC $t_R$=1.371 min. 1H NMR (400 MHz, methanol-$d_4$) δ 6.77-6.71 (d, J=2.5 Hz, 1H), 6.61-6.56 (d, J=2.6 Hz, 1H), 6.15-6.10 (s, 1H), 4.52-4.43 (d, J=5.4 Hz, 3H), 3.99-3.88 (d, J=10.5 Hz, 2H), 3.42-3.35 (d, J=11.8 Hz, 2H), 3.13-2.94 (m, 2H), 2.77-2.46 (m, 10H), 2.40-2.35 (s, 3H), 2.29-2.24 (s, 3H), 2.23-2.18 (s, 3H), 2.02-1.93 (m, 1H), 1.76-1.68 (d, J=11.3 Hz, 1H), 1.66-1.57 (d, J=8.3 Hz, 1H), 1.19-1.06 (d, J=6.5 Hz, 4H), 0.91-0.82 (t, J=7.0 Hz, 3H).

Example 23: Preparation of the Compound N-((4,6-dimethyl-2-oxo-1,2-dihydropyridin-3-yl)methyl)-3-(ethyl(tetrahydro-2H-pyran-4-yl)amino)-5-(cis-3-(4-ethylpiperazin-1-yl)cyclobutoxy)-2-methylbenzamide (23)

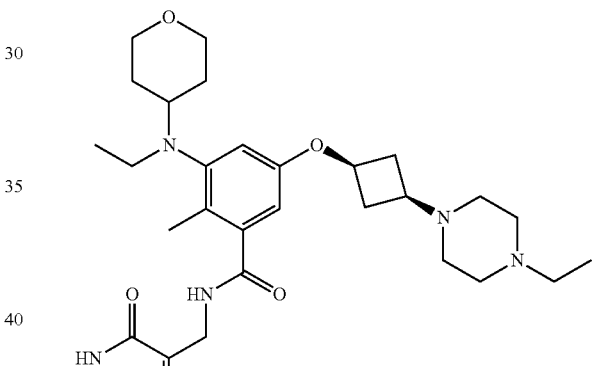

The title compound was prepared by referring to Example 2 and Example 4.

m/z (ES+), [M+H]$^+$=580; HPLC $t_R$=1.304 min. 1H NMR (400 MHz, methanol-$d_4$) δ 7.13-6.98 (s, 1H), 6.93-6.79 (s, 1H), 6.17-6.12 (s, 1H), 4.51-4.46 (s, 2H), 4.05-3.96 (d, J=10.1 Hz, 1H), 3.81-3.48 (d, J=20.7 Hz, 4H), 3.46-3.36 (d, J=11.2 Hz, 3H), 3.31-3.09 (q, J=7.3 Hz, 3H), 2.92-2.50 (dt, J=13.0, 6.4 Hz, 2H), 2.42-2.33 (m, 5H), 2.32-2.24 (d, J=10.8 Hz, 6H), 1.98-1.66 (s, 4H), 1.41-1.33 (t, J=7.3 Hz, 3H), 1.04-0.95 (t, J=6.8 Hz, 3H).

Example 24: Preparation of the Compound N-((4,6-dimethyl-2-oxo-1,2-dihydropyridin-3-yl)methyl)-3-(ethyl(tetrahydro-2H-pyran-4-yl)amino)-5-(trans-3-(4-ethylpiperazin-1-yl)cyclobutoxy)-2-methylbenzamide (24)

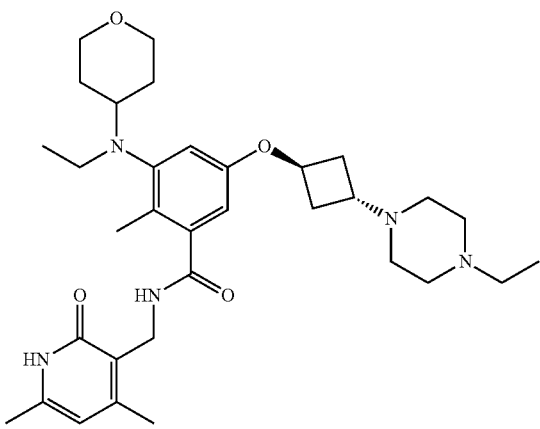 [SMILES: CCN1CCN([C@H]2C[C@H](Oc3cc(C(=O)NCc4c(C)cc(C)[nH]c4=O)c(C)c(N(CC)C4CCOCC4)c3)C2)CC1]

The title compound was prepared by referring to Example 2 and Example 4.

m/z (ES+), [M+H]$^+$=580; HPLC $t_R$=1.288 min. 1H NMR (400 MHz, methanol-$d_4$) δ 6.77-6.71 (d, J=2.5 Hz, 1H), 6.61-6.55 (d, J=2.5 Hz, 1H), 6.15-6.10 (s, 1H), 4.52-4.43 (d, J=5.1 Hz, 3H), 3.99-3.89 (d, J=11.4 Hz, OH), 3.41-3.35 (d, J=11.9 Hz, 1H), 3.18-2.96 (m, OH), 2.82-2.16 (m, 21H), 2.03-1.93 (m, 2H), 1.75-1.56 (m, 4H), 1.17-1.08 (t, J=7.2 Hz, 3H), 0.91-0.82 (t, J=7.0 Hz, 3H).

Example 25: Preparation of the Compound cis-5-(3-(4-acetylpiperazin-1-yl) cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide (25)

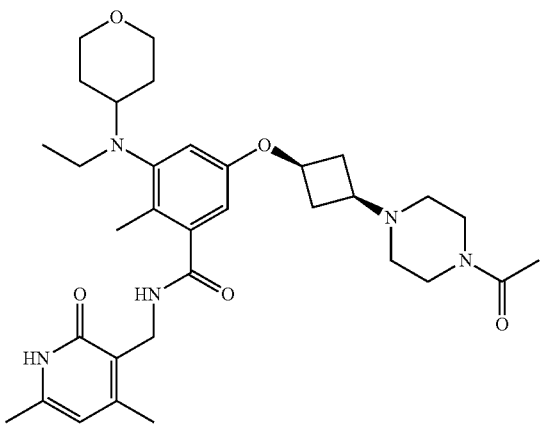 [SMILES: CCN(c1cc(O[C@H]2C[C@@H](N3CCN(C(C)=O)CC3)C2)cc(C(=O)NCc2c(C)cc(C)[nH]c2=O)c1C)C1CCOCC1]

The title compound was prepared by referring to Example 2 and Example 4.

m/z (ES+), [M+H]$^+$=594; HPLC $t_R$=1.221 min. 1H NMR (300 MHz, methanol-$d_4$) δ 6.74-6.69 (d, J=2.5 Hz, 1H), 6.55-6.51 (d, J=2.5 Hz, 1H), 6.15-6.12 (s, 1H), 4.82-4.73 (s, 1H), 4.50-4.44 (s, 2H), 3.99-3.88 (d, J=10.6 Hz, 2H), 3.68-3.54 (m, 4H), 3.41-3.35 (s, 2H), 3.12-3.01 (m, 4H), 2.52-2.34 (d, J=13.2 Hz, 4H), 2.33-2.16 (d, J=18.6 Hz, 8H), 2.15-2.08 (s, 3H), 1.78-1.56 (m, 5H), 0.92-0.82 (t, J=7.0 Hz, 3H).

Example 26: Preparation of the Compound trans-5-(3-(4-acetylpiperazin-1-yl) cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide (26)

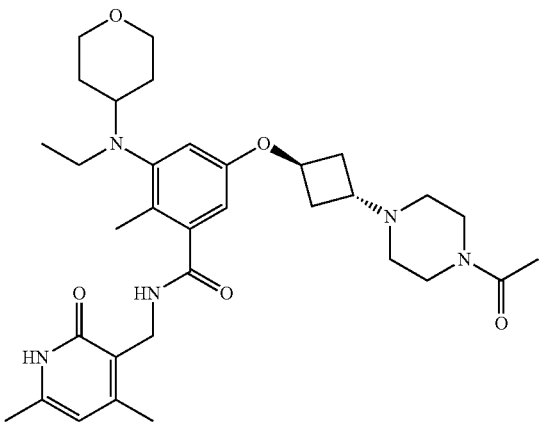 [SMILES: CCN(c1cc(O[C@H]2C[C@H](N3CCN(C(C)=O)CC3)C2)cc(C(=O)NCc2c(C)cc(C)[nH]c2=O)c1C)C1CCOCC1]

The title compound was prepared by referring to Example 2 and Example 4.

m/z (ES+), [M+H]$^+$=594; HPLC $t_R$=1.204 min. 1H NMR (400 MHz, methanol-$d_4$) δ 6.77-6.71 (d, J=2.5 Hz, 1H), 6.61-6.56 (d, J=2.5 Hz, 1H), 6.15-6.10 (s, 1H), 4.92-4.87 (s, 22H), 4.53-4.45 (d, J=11.0 Hz, 2H), 3.99-3.90 (d, J=11.5 Hz, 2H), 3.63-3.53 (m, 4H), 3.41-3.35 (d, J=11.4 Hz, 21H), 3.13-3.02 (q, J=6.9 Hz, 3H), 2.77-2.68 (m, 2H), 2.61-2.54 (d, J=7.4 Hz, 1H), 2.49-2.35 (s, 5H), 2.29-2.24 (s, 3H), 2.23-2.18 (s, 3H), 2.14-2.09 (s, 3H), 2.05-1.94 (m, 2H), 1.76-1.59 (m, 1H), 0.91-0.82 (t, J=7.0 Hz, 3H).

Example 27: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(cis-3-(4-(methylsulfonyl)piperazin-1-yl) cyclobutoxy)benzamide (27)

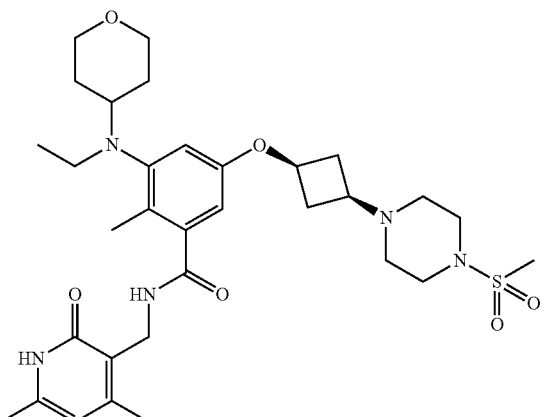

The title compound was prepared by referring to Example 2 and Example 4.

m/z (ES+), [M+H]$^+$=630; HPLC $t_R$=1.329 min. 1H NMR (400 MHz, methanol-$d_4$) δ 6.74-6.70 (d, J=2.6 Hz, 1H), 6.55-6.52 (d, J=2.5 Hz, 1H), 6.15-6.12 (s, 1H), 4.81-4.73 (s, 1H), 4.50-4.45 (s, 2H), 3.97-3.89 (d, J=10.5 Hz, 2H), 3.41-3.35 (d, J=11.8 Hz, 1H), 3.31-3.22 (m, 4H), 3.16-3.00 (m, 0H), 2.90-2.85 (s, 3H), 2.57-2.48 (s, 4H), 2.46-2.36 (s, 0H), 2.33-2.24 (m, 0H), 2.23-2.18 (s, 3H), 1.78-1.68 (d, J=11.4 Hz, 2H), 1.67-1.57 (m, 2H), 0.91-0.83 (t, J=7.0 Hz, 3H).

Example 28: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(4-(methylsulfonyl)piperazin-1-yl)cyclobutoxy)benzamide (28)

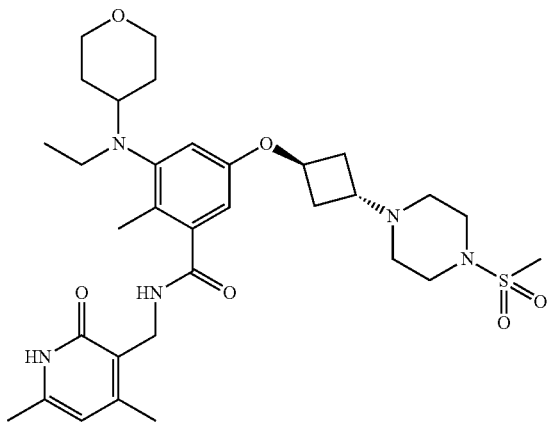 [SMILES: CCN(c1cc(O[C@H]2C[C@H](N3CCN(S(C)(=O)=O)CC3)C2)cc(C(=O)NCc2c(C)cc(C)[nH]c2=O)c1C)C1CCOCC1]

The title compound was prepared by referring to Example 2 and Example 4.

m/z (ES+), [M+H]$^+$=630; HPLC $t_R$=1.296 min. 1H NMR (400 MHz, methanol-$d_4$) δ 6.75-6.73 (d, J=2.4 Hz, 1H), 6.60-6.57 (d, J=2.3 Hz, 1H), 6.14-6.11 (s, 1H), 4.48-4.45 (s, 1H), 3.97-3.89 (d, J=10.7 Hz, 2H), 3.41-3.36 (s, 2H), 3.30-3.22 (s, 1H), 3.11-3.02 (dt, J=16.9, 8.5 Hz, 3H), 2.89-2.84 (s, 3H), 2.77-2.70 (d, J=6.8 Hz, 2H), 2.64-2.58 (m, 1H), 2.53-2.47 (s, 1H), 2.42-2.37 (s, 3H), 2.29-2.24 (s, 3H), 2.23-2.17 (s, 3H), 2.01-1.93 (m, 1H), 1.76-1.70 (d, J=11.0 Hz, 2H), 1.68-1.59 (m, 2H), 0.90-0.84 (t, J=7.0 Hz, 3H).

Example 29: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(morpholinylmethyl)cyclobutoxy)benzamide (29)

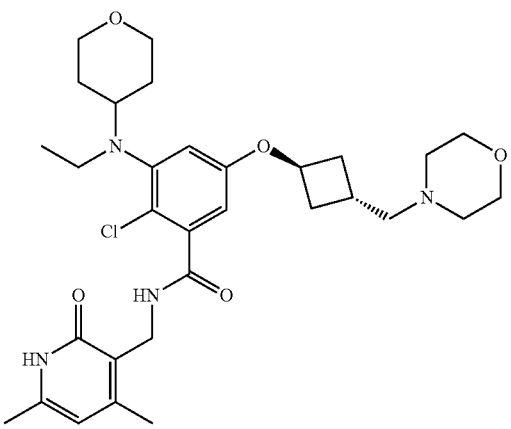 [SMILES: CCN(c1cc(O[C@H]2C[C@H](CN3CCOCC3)C2)cc(C(=O)NCc2c(C)cc(C)[nH]c2=O)c1Cl)C1CCOCC1]

The title compound was prepared by referring to Example 2 and Example 4.

m/z (ES+), [M+H]$^+$=587; HPLC $t_R$=0.96 min. 1H NMR (400 MHz, DMSO-$d_6$) δ 11.47 (s, 1H), 8.23 (t, J=4.9 Hz, 1H), 6.67 (d, J=2.8 Hz, 1H), 6.43 (d, J=2.8 Hz, 1H), 5.87 (s, 1H), 4.86-4.78 (m, 1H), 4.26 (d, J=5.0 Hz, 2H), 3.85 (d, J=11.3 Hz, 2H), 3.60-3.52 (m, 4H), 3.24 (t, J=10.4 Hz, 2H), 3.10-3.01 (m, 2H), 2.42 (d, J=7.3 Hz, 2H), 2.34 (s, 3H), 2.15 (d, J=30.8 Hz, 9H), 1.68-1.50 (m, 4H), 0.82 (t, J=6.9 Hz, 3H).

Example 30: Preparation of the Compound 2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)benzamide (30)

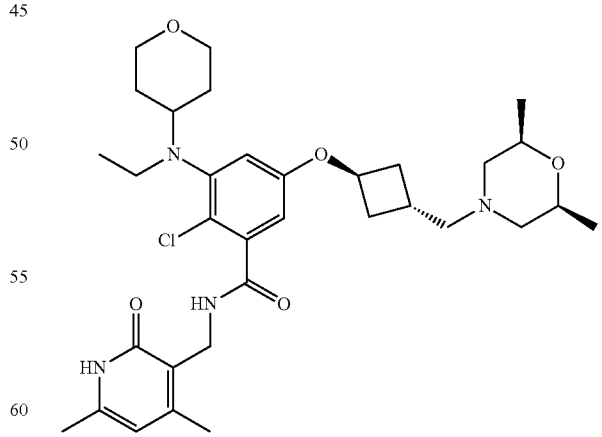

The title compound was prepared by referring to Example 1, Example 2, and Example 4.

m/z (ES+), [M+H]$^+$=615; HPLC $t_R$=1.471 min. 1H NMR (400 MHz, methanol-$d_4$) δ 6.76-6.72 (d, J=2.8 Hz, 1H), 6.59-6.55 (d, J=2.8 Hz, 1H), 6.16-6.11 (s, 1H), 4.82-4.75 (t, J=5.8 Hz, 1H), 4.52-4.46 (s, 1H), 4.00-3.90 (d, J=11.6 Hz, 2H), 3.73-3.63 (m, 2H), 3.41-3.35 (m, 2H), 3.29-3.22 (dd, J=10.0, 4.8 Hz, 1H), 3.18-3.10 (q, J=7.0 Hz, 2H), 2.83-2.77 (d, J=11.2 Hz, 1H), 2.72-2.64 (m, 1H), 2.57-2.51 (d, J=7.4 Hz, 2H), 2.42-2.38 (s, 2H), 2.34-2.21 (m, 6H), 1.81-1.63 (m, 5H), 1.17-1.11 (d, J=6.3 Hz, 5H), 0.95-0.86 (t, J=7.0 Hz, 2H).

Example 31: Preparation of the Compound N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)-2-methylbenzamide (31)

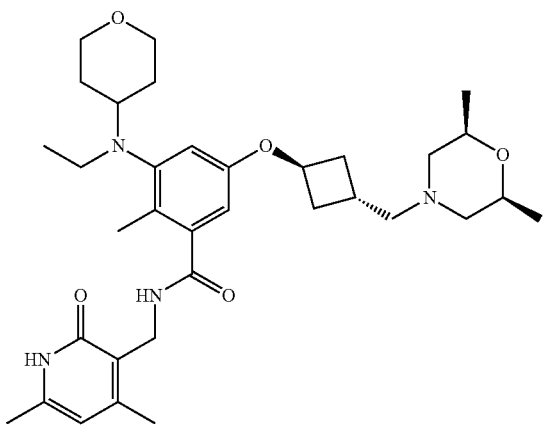

The title compound was prepared by referring to Example 1, Example 2, and Example 4.

m/z (ES+), [M+H]$^+$=595; HPLC t$_R$=0.767 min. 1H NMR (400 MHz, methanol-d$_4$) δ 6.72-6.68 (d, J=2.6 Hz, 1H), 6.54-6.51 (d, J=2.5 Hz, 1H), 6.15-6.11 (s, 1H), 4.78-4.73 (t, J=5.9 Hz, 1H), 4.49-4.45 (s, 2H), 3.98-3.90 (d, J=11.5 Hz, 2H), 3.73-3.66 (d, J=7.5 Hz, 2H), 3.41-3.35 (d, J=11.2 Hz, 2H), 3.11-3.01 (q, J=7.1 Hz, 2H), 2.81-2.74 (d, J=11.4 Hz, 2H), 2.69-2.62 (m, 1H), 2.56-2.49 (d, J=7.5 Hz, 2H), 2.41-2.38 (s, 2H), 2.34-2.24 (d, J=5.6 Hz, 6H), 2.21-2.15 (s, 2H), 1.78-1.69 (m, 3H), 1.67-1.59 (m, 1H), 1.17-1.13 (d, J=6.3 Hz, 5H), 0.90-0.84 (t, J=7.0 Hz, 2H).

Example 32: Preparation of the Compound N-((4,6-dimethyl-2-oxo-1,2-dihydropyridin-3-yl)methyl)-3-(ethyl(trans-4-((2-methoxyethyl)(methyl)amino)cyclohexyl)amino)-2-methyl-5-(trans-3-(morpholinylmethyl)cyclobutoxy)benzamide (32)

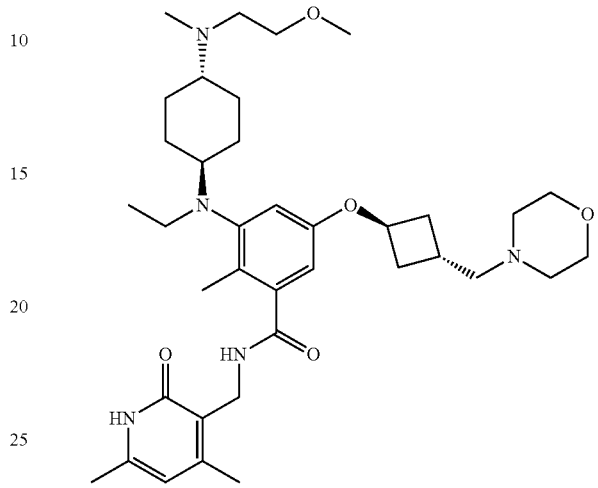

The title compound was prepared by referring to Example 1, Example 2, and Example 4.

m/z (ES+), [M+H]$^+$=652; HPLC t$_R$=0.733 min. 1H NMR (400 MHz, methanol-d$_4$) δ 6.70-6.64 (d, J=2.6 Hz, 1H), 6.54-6.51 (d, J=2.5 Hz, 1H), 6.15-6.12 (s, 1H), 4.79-4.72 (t, J=5.8 Hz, 1H), 4.50-4.44 (s, 1H), 3.75-3.60 (dt, J=35.4, 5.1 Hz, 4H), 3.55-3.48 (t, J=5.8 Hz, 2H), 3.47-3.40 (s, 1H), 3.22-3.11 (s, 1H), 3.09-2.97 (d, J=7.0 Hz, 1H), 2.73-2.63 (m, 2H), 2.58-2.51 (d, J=7.5 Hz, 2H), 2.51-2.44 (d, J=5.5 Hz, 3H), 2.43-2.38 (s, 2H), 2.36-2.32 (s, 2H), 2.30-2.10 (s, 8H), 2.04-1.94 (s, 1H), 1.71-1.61 (d, J=13.1 Hz, 1H), 1.50-1.36 (d, J=12.0 Hz, 3H), 0.94-0.83 (t, J=7.0 Hz, 2H).

Example 33: Preparation of the Compound N-((4,6-dimethyl-2-oxo-1,2-dihydropyridin-3-yl)methyl)-5-((cis-3-(cis-2,6-dimethylmorpholinyl)cyclobutoxy)-3-((cis-2,6-dimethyltetrahydro-2H-pyran-4-yl)(ethyl)amino)-2-methylbenzamide (33)

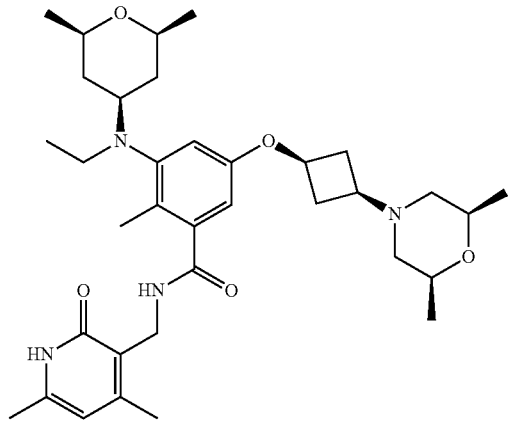

The title compound was prepared by referring to Example 1, Example 2, and Example 4.

m/z (ES+), [M+H]$^+$=609; HPLC $t_R$=2.491 min. 1H NMR (400 MHz, methanol-d$_4$) δ 6.20-6.11 (s, 1H), 4.50-4.45 (s, 1H), 4.05-3.97 (d, J=8.7 Hz, 1H), 3.91-3.82 (s, 2H), 3.58-3.44 (s, 4H), 2.91-2.72 (s, 2H), 2.68-2.54 (t, J=11.6 Hz, 3H), 2.45-2.37 (s, 3H), 2.31-2.18 (d, J=14.4 Hz, 5H), 1.85-1.72 (s, 1H), 1.37-1.24 (d, J=6.2 Hz, 6H), 1.23-1.06 (d, J=6.1 Hz, 5H), 0.96-0.87 (s, 2H).

Example 34: Preparation of the Compound N-((4,6-dimethyl-2-oxo-1,2-dihydropyridin-3-yl)methyl)-3-(ethyl(trans-4-((2-methoxyethyl)(methyl)amino)cyclohexyl)amino)-2-methyl-5-(3-morpholinylcyclobutoxy)benzamide (34)

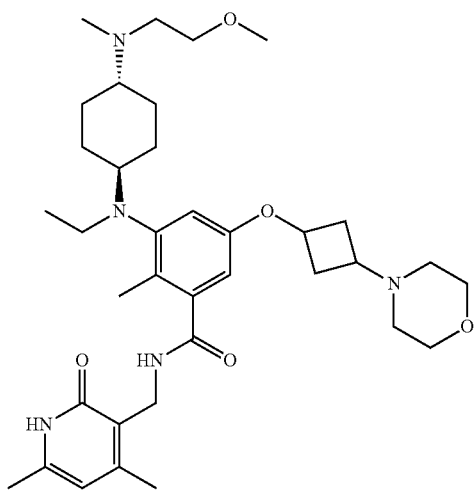 [SMILES: CCN(c1cc(OC2CC(N3CCOCC3)C2)cc(C(=O)NCc2c(C)cc(C)[nH]c2=O)c1C)[C@H]1CC[C@H](N(C)CCOC)CC1]

The title compound was prepared by referring to Example 1, Example 2, and Example 4.

m/z (ES+), [M+H]$^+$=638.6; HPLC $t_R$=0.867 min. 1H NMR (400 MHz, methanol-d$_4$) δ 6.83-6.72 (s, 1H), 6.66-6.56 (s, 1H), 6.20-6.12 (s, 1H), 4.53-4.41 (s, 2H), 4.18-3.99 (dq, J=15.6, 9.0, 7.8 Hz, 3H), 3.88-3.68 (m, 4H), 3.62-3.56 (s, 1H), 3.55-3.46 (s, 2H), 3.46-3.40 (s, 3H), 3.39-3.35 (s, 1H), 3.28-3.21 (m, 1H), 3.18-2.91 (s, 4H), 2.90-2.74 (m, 5H), 2.64-2.51 (ddd, J=14.2, 8.2, 2.6 Hz, 2H), 2.48-2.15 (m, 9H), 2.12-1.31 (m, 7H), 0.99-0.87 (t, J=7.0 Hz, 3H).

Example 35: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-((cis-2,6-dimethyltetrahydro-2H-pyran-4-yl)(ethyl)amino)-2-methylbenzamide (35)

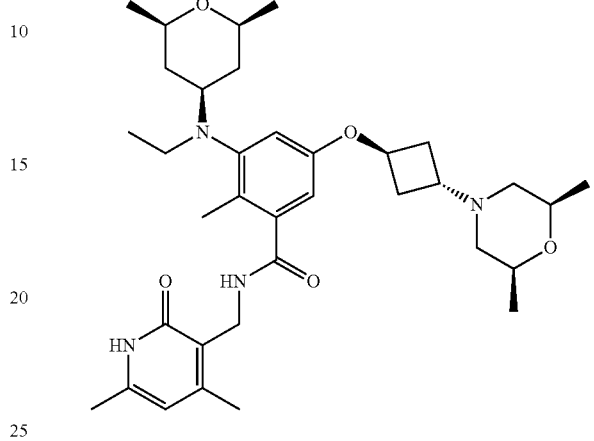

The title compound was prepared by referring to Example 1, Example 2, and Example 4.

m/z (ES+), [M+H]$^+$=609; HPLC $t_R$=1.579 min. 1H NMR (400 MHz, methanol-d$_4$) δ 7.13-6.94 (s, 1H), 6.89-6.74 (s, 1H), 6.17-6.10 (s, 1H), 4.52-4.43 (s, 2H), 4.09-3.94 (t, J=7.8 Hz, 1H), 3.94-3.79 (q, J=6.2 Hz, 2H), 3.78-3.34 (d, J=11.8 Hz, 7H), 2.89-2.76 (s, 2H), 2.68-2.52 (q, J=11.4, 10.7 Hz, 4H), 2.45-2.35 (s, 3H), 2.33-2.21 (d, J=3.3 Hz, 5H), 1.98-1.71 (s, 2H), 1.46-1.11 (dd, J=31.2, 6.2 Hz, 13H), 1.04-0.89 (d, J=7.2 Hz, 3H).

Example 36: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(piperidin-1-ylmethyl)cyclobutoxy)benzamide (36)

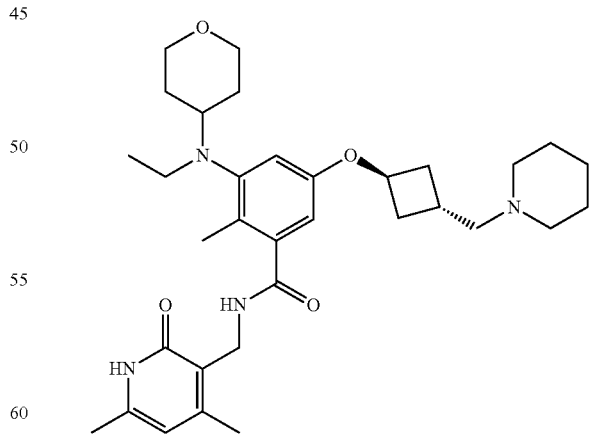

The title compound was prepared by referring to Example 1, Example 2, and Example 4.

m/z (ES+), [M+H]$^+$=565.6; HPLC $t_R$=0.834 min. 1H NMR (400 MHz, methanol-d$_4$) δ 6.74-6.67 (d, J=2.5 Hz, 1H), 6.57-6.52 (d, J=2.5 Hz, 1H), 6.16-6.12 (s, 1H), 4.82-

4.74 (d, J=7.5 Hz, 1H), 4.50-4.44 (s, 2H), 3.98-3.88 (d, J=11.2 Hz, 2H), 3.41-3.34 (m, 3H), 3.11-2.98 (dd, J=16.7, 9.5 Hz, 3H), 2.96-2.73 (d, J=41.5 Hz, 5H), 2.42-2.37 (s, 3H), 2.37-2.29 (s, 3H), 2.29-2.24 (s, 3H), 2.22-2.16 (s, 2H), 1.82-1.51 (m, 9H), 0.90-0.82 (t, J=7.1 Hz, 3H).

Example 37: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperidin-1-yl)cyclobutoxy)benzamide (37)

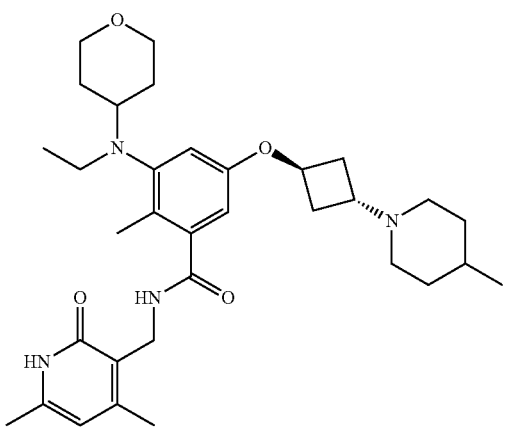

The title compound was prepared by referring to Example 1, Example 2, and Example 4.

m/z (ES+), [M+H]$^+$=565; HPLC t$_R$=2.499/2.424 min. 1H NMR (400 MHz, methanol-d$_4$) δ 6.77-6.70 (dd, J=6.9, 2.6 Hz, 1H), 6.61-6.52 (dd, J=23.3, 2.5 Hz, 1H), 6.15-6.11 (s, 1H), 4.83-4.76 (d, J=7.1 Hz, 1H), 4.50-4.44 (s, 2H), 3.98-3.89 (d, J=11.4 Hz, 2H), 3.40-3.35 (m, 2H), 3.25-3.14 (s, 2H), 3.12-2.98 (m, 3H), 2.60-2.49 (s, 2H), 2.46-2.15 (m, 12H), 1.87-1.79 (d, J=13.8 Hz, 2H), 1.76-1.55 (m, 5H), 1.40-1.26 (m, 2H), 1.04-0.99 (dd, J=6.6, 3.1 Hz, 3H), 0.91-0.83 (t, J=7.0 Hz, 3H).

Example 38: Preparation of the Compound N-((4,6-dimethyl-2-oxo-1,2-dihydropyridin-3-yl)methyl)-5-(((1S,3S)-3-((2S,6R)-2,6-dimethylmorpholinyl)cyclobutoxy)-3-(((2R,4s,6S)-2,6-dimethyltetrahydro-2H-pyran-4-yl)(ethyl)amino)-2-methylbenzamide (38)

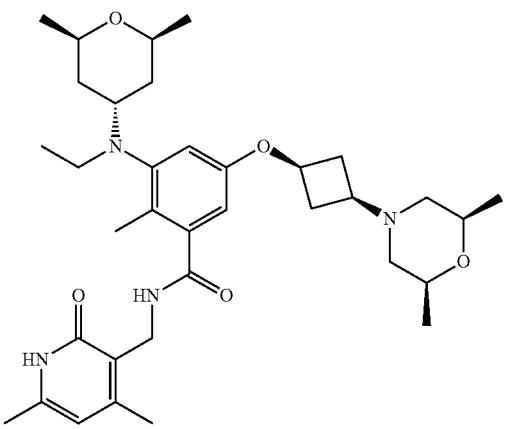

The title compound was prepared by referring to Example 1, Example 2, and Example 4.

m/z (ES+), [M+H]$^+$=609; HPLC t$_R$=1.454 min. 1H NMR (400 MHz, methanol-d$_4$) δ 6.76-6.71 (d, J=2.6 Hz, 1H), 6.64-6.57 (d, J=2.5 Hz, 1H), 6.16-6.10 (s, 1H), 4.53-4.42 (d, J=3.4 Hz, 2H), 3.95-3.61 (m, 3H), 3.10-2.91 (s, 1H), 2.82-2.75 (d, J=11.2 Hz, 1H), 2.74-2.67 (td, J=9.9, 6.8 Hz, 1H), 2.56-2.46 (p, J=8.0 Hz, 1H), 2.45-2.36 (s, 2H), 2.32-2.11 (d, J=10.7 Hz, 4H), 2.07-1.85 (q, J=9.0 Hz, 2H), 1.64-1.56 (t, J=10.8 Hz, 1H), 1.52-0.61 (m, 12H).

Example 39: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-((trans-2,6-dimethyltetrahydro-2H-pyran-4-yl)(ethyl)amino)-2-methylbenzamide (39)

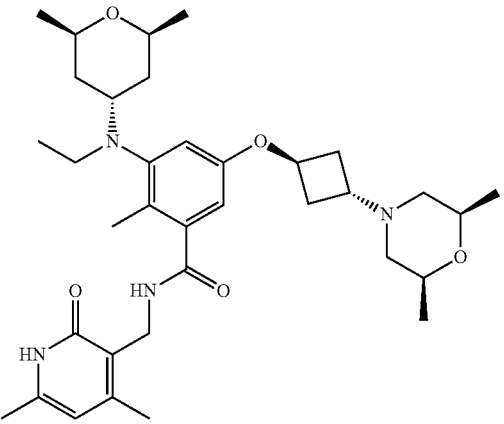

The title compound was prepared by referring to Example 1, Example 2, and Example 4.

m/z (ES+), [M+H]$^+$=609; HPLC t$_R$=1.479 min. 1H NMR (400 MHz, methanol-d$_4$) δ 6.72-6.67 (d, J=2.6 Hz, 1H), 6.56-6.52 (d, J=2.5 Hz, 1H), 6.15-6.11 (s, 1H), 4.81-4.72 (dt, J=7.0, 3.7 Hz, 1H), 4.51-4.42 (s, 2H), 3.96-3.65 (ddd, J=12.1, 5.9, 2.6 Hz, 3H), 3.10-2.95 (p, J=7.2 Hz, 2H), 2.89-2.78 (d, J=11.2 Hz, 2H), 2.48-2.36 (s, 4H), 2.30-2.14 (d, J=10.5 Hz, 7H), 1.62-1.44 (t, J=10.9 Hz, 2H), 1.39-0.76 (m, 14H).

Example 40: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(cis-3-morpholinylcyclobutoxy)benzamide (40)

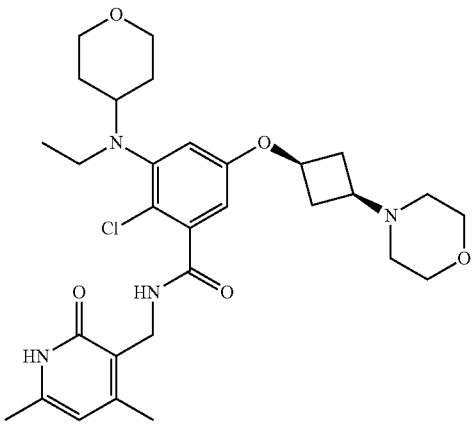 [SMILES: CCN(c1cc(O[C@H]2C[C@@H](N3CCOCC3)C2)cc(C(=O)NCc2c(C)cc(C)[nH]c2=O)c1Cl)C1CCOCC1]

m/z (ES+), [M+H]$^+$=573; HPLC $t_R$=0.842 min. 1H NMR (400 MHz, DMSO-$d_6$) δ 11.58-11.53 (s, 1H), 7.80-7.72 (t, J=6.0 Hz, 1H), 5.90-5.85 (s, 1H), 5.01-4.88 (s, 2H), 4.29-4.22 (d, J=5.9 Hz, 2H), 3.92-3.75 (s, 2H), 3.29-3.02 (m, 5H), 2.25-2.17 (d, J=14.6 Hz, 6H), 2.14-2.09 (s, 3H), 1.98-1.72 (s, 1H), 1.50-1.15 (s, 3H), 0.91-0.82 (t, J=7.2 Hz, 3H).

Example 41: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-morpholinylcyclobutoxy)benzamide (41)

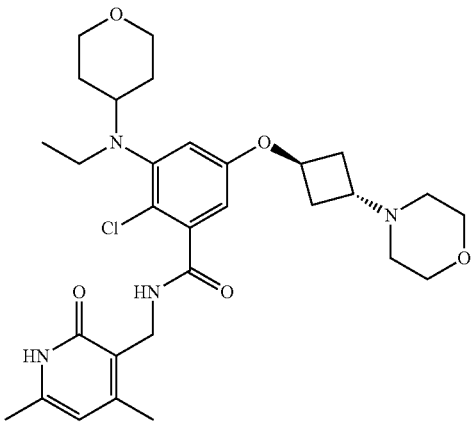 [SMILES: CCN(c1cc(O[C@H]2C[C@H](N3CCOCC3)C2)cc(C(=O)NCc2c(C)cc(C)[nH]c2=O)c1Cl)C1CCOCC1]

The title compound was prepared by referring to Example 1, Example 2, and Example 4.

m/z (ES+), [M+H]$^+$=573; HPLC $t_R$=0.842 min. 1H NMR (400 MHz, methanol-$d_4$) δ 6.78-6.72 (d, J=2.9 Hz, 1H), 6.60-6.55 (d, J=2.8 Hz, 1H), 6.17-6.11 (s, 1H), 4.83-4.75 (tt, J=6.8, 3.4 Hz, 1H), 4.52-4.46 (s, 2H), 3.98-3.90 (m, 2H), 3.79-3.69 (t, J=4.7 Hz, 4H), 3.42-3.35 (dd, J=11.2, 3.0 Hz, 2H), 3.32-3.22 (dq, J=9.7, 5.2, 4.8 Hz, 2H), 3.20-3.02 (m, 3H), 2.52-2.36 (d, J=26.6 Hz, 8H), 2.31-2.22 (m, 5H), 1.82-1.62 (m, 4H), 0.95-0.85 (t, J=7.0 Hz, 3H).

Example 42: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(cis-3-(piperazin-1-yl)cyclobutoxy)benzamide (42)

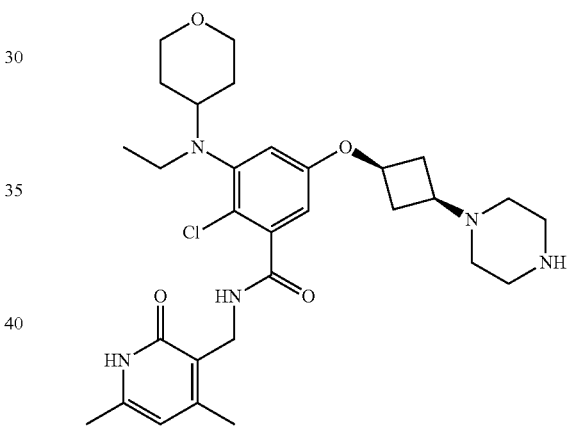

The title compound was prepared by referring to Example 1, Example 2, and Example 4.

m/z (ES+), [M+H]$^+$=572; HPLC $t_R$=1.154 min. 1H NMR (400 MHz, methanol-$d_4$) δ 6.99-6.94 (s, 1H), 6.83-6.79 (s, 1H), 6.20-6.16 (s, 1H), 4.68-4.58 (m, 1H), 4.52-4.48 (s, 2H), 4.01-3.94 (d, J=11.7 Hz, 2H), 3.55-3.36 (m, 8H), 3.25-3.08 (d, J=28.2 Hz, 5H), 2.99-2.88 (s, 2H), 2.44-2.37 (s, 3H), 2.32-2.20 (s, 4H), 1.87-1.67 (m, 3H), 1.04-0.88 (t, J=7.0 Hz, 3H).

Example 43: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperazin-1-yl)cyclobutoxy)benzamide (43)

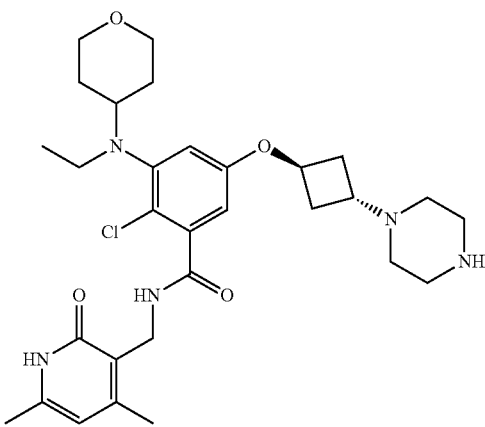 [SMILES: CCN(c1cc(O[C@H]2C[C@H](N3CCNCC3)C2)cc(C(=O)NCc2c(C)cc(C)[nH]c2=O)c1Cl)C1CCOCC1]

The title compound was prepared by referring to Example 1, Example 2, and Example 4.

m/z (ES+), [M+H]+=572; HPLC $t_R$=0.838 min. 1H NMR (400 MHz, methanol-$d_4$) δ 6.17-6.12 (s, 1H), 4.52-4.46 (s, 1H), 4.00-3.93 (d, J=11.8 Hz, 1H), 3.46-3.35 (d, J=11.8 Hz, 3H), 2.97-2.79 (s, 3H), 2.59-2.52 (s, 1H), 2.46-2.33 (s, 3H), 2.30-2.22 (s, 2H), 1.83-1.68 (d, J=22.1 Hz, 2H), 0.99-0.91 (t, J=6.9 Hz, 2H).

Example 44: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)-2-methylbenzamide (44)

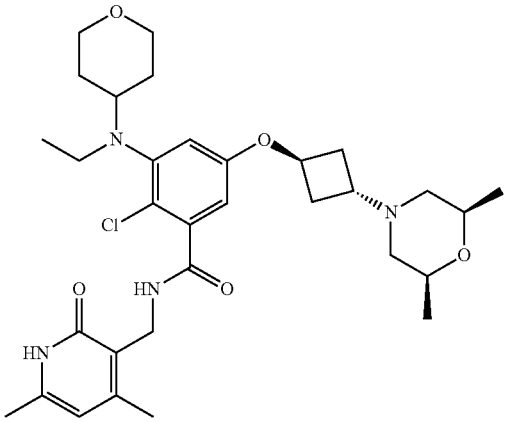

The title compound was prepared by referring to Example 1, Example 2, and Example 4.

m/z (ES+), [M+H]+=581; HPLC $t_R$=1.438 min. 1H NMR (400 MHz, methanol-$d_4$) δ 6.75-6.67 (s, 1H), 6.56-6.52 (d, J=2.5 Hz, 1H), 6.15-6.10 (s, 1H), 4.78-4.73 (s, 1H), 4.50-4.44 (s, 2H), 3.99-3.89 (d, J=11.6 Hz, 2H), 3.77-3.66 (m, 2H), 3.41-3.35 (d, J=11.8 Hz, 2H), 3.11-2.95 (dq, J=22.1, 6.9 Hz, 4H), 2.88-2.79 (d, J=11.2 Hz, 2H), 2.49-2.37 (s, 4H), 2.29-2.24 (s, 4H), 2.23-2.17 (s, 3H), 1.79-1.69 (d, J=12.6 Hz, 2H), 1.67-1.51 (m, 3H), 1.34-1.24 (d, J=20.0 Hz, 1H), 1.22-1.10 (d, J=6.2 Hz, 6H), 0.92-0.81 (t, J=7.0 Hz, 3H).

Example 45: Preparation of the Compound 3-((4,4-difluorocyclohexyl)(ethyl) amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide (45)

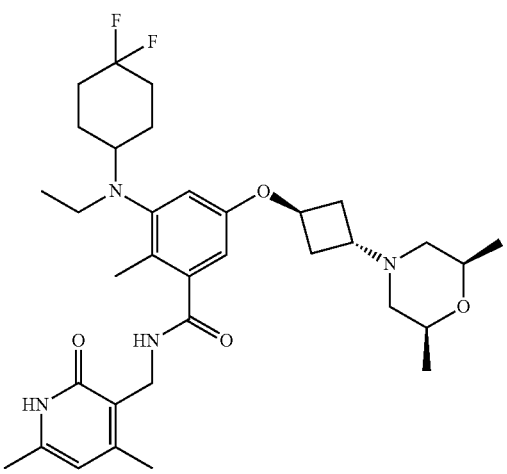

The title compound was prepared by referring to Example 1 with tetrahydropyran-4-one and cyclobutanol replaced by 4,4-difluorocyclohexanone and 1,3-cis-3-(2,6-cis-2,6-dimethylmorpholinyl)cyclobutyl-1-ol, respectively. 1,3-cis-3-(2,6-cis-2,6-dimethylmorpholinyl) cyclobutyl-1-ol was prepared by referring to Example 4.

m/z (ES+), [M+H]+=615; HPLC $t_R$=1.704 min. 1H NMR (300 MHz, methanol-$d_4$) δ 6.73-6.67 (d, J=2.4 Hz, 1H), 6.54-6.50 (d, J=2.5 Hz, 1H), 6.15-6.11 (s, 1H), 4.80-4.72 (s, 1H), 4.49-4.44 (s, 2H), 3.78-3.62 (d, J=13.4 Hz, 2H), 3.14-2.96 (d, J=7.2 Hz, 4H), 2.88-2.82 (d, J=11.3 Hz, 2H), 2.51-2.34 (s, 5H), 2.33-2.22 (s, 5H), 2.22-2.16 (s, 3H), 2.12-1.94 (s, 2H), 1.88-1.66 (d, J=24.7 Hz, 6H), 1.63-1.51 (t, J=10.9 Hz, 2H), 1.21-1.12 (d, J=6.3 Hz, 6H), 0.92-0.82 (t, J=7.0 Hz, 3H).

Example 46: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydrofuran-3-yl)amino)-2-methylbenzamide (46)

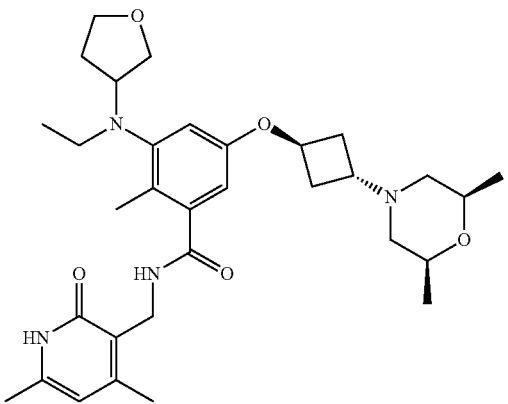

The title compound was prepared by referring to Example 1, Example 2, and Example 4.

m/z (ES+), [M+H]$^+$=567.5; HPLC $t_R$=0.883 min. 1H NMR (400 MHz, methanol-d$_4$) δ 6.78-6.73 (d, J=2.6 Hz, 1H), 6.57-6.53 (d, J=2.6 Hz, 1H), 6.14-6.12 (s, 1H), 4.83-4.73 (m, 1H), 4.48-4.44 (s, 1H), 3.94-3.83 (m, 2H), 3.81-3.75 (m, 1H), 3.74-3.66 (m, 2H), 3.57-3.50 (m, 1H), 3.07-2.96 (q, J=7.0 Hz, 2H), 2.87-2.82 (d, J=11.1 Hz, 2H), 2.48-2.35 (s, 4H), 2.32-2.17 (d, J=19.5 Hz, 7H), 2.06-1.97 (dt, J=12.5, 6.2 Hz, 1H), 1.89-1.80 (d, J=7.0 Hz, 1H), 1.60-1.52 (t, J=10.9 Hz, 2H), 1.22-1.12 (d, J=6.3 Hz, 5H), 0.91-0.83 (t, J=7.1 Hz, 2H).

Example 47: Preparation of the Compound 3-((8-oxabicyclo[3.2.1]octan-3-yl)(ethyl) amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide (47)

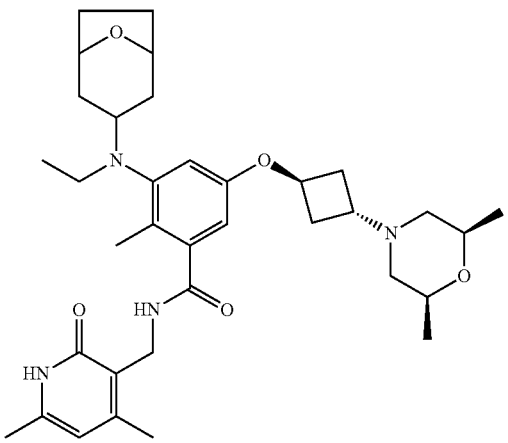

The title compound was prepared by referring to Example 1 with tetrahydropyran-4-one and cyclobutanol replaced by 8-oxabicyclo[3.2.1]octan-3-one and 1,3-cis-3-(2,6-cis-2,6-dimethylmorpholinyl)cyclobutyl-1-ol, respectively. 1,3-cis-3-(2,6-cis-2,6-dimethylmorpholinyl) cyclobutyl-1-ol was prepared by referring to Example 4.

m/z (ES+), [M+H]$^+$=607; HPLC $t_R$=1.471 min. 1H NMR (300 MHz, methanol-d$_4$) δ 6.58-6.55 (d, J=2.6 Hz, 1H), 6.53-6.49 (d, J=2.5 Hz, 1H), 6.14-6.12 (s, 1H), 4.81-4.71 (d d, J=6.7, 3.5 Hz, 1H), 4.51-4.44 (s, 2H), 4.30-4.22 (s, 2H), 3.76-3.62 (m, 3H), 3.20-3.09 (d, J=7.1 Hz, 2H), 3.05-2.96 (q, J=7.2 Hz, 1H), 2.88-2.81 (d, J=11.2 Hz, 2H), 2.48-2.36 (s, 4H), 2.31-2.17 (m, 7H), 2.11-1.95 (d t, J=20.2, 6.1 Hz, 3H), 1.89-1.75 (t, J=12.7 Hz, 3H), 1.62-1.52 (t, J=10.9 Hz, 2H), 1.19-1.14 (d, J=6.3 Hz, 5H), 0.86-0.77 (t, J=7.0 Hz, 3H).

Example 48: Preparation of the Compound 2-chloro-N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)benzamide (48)

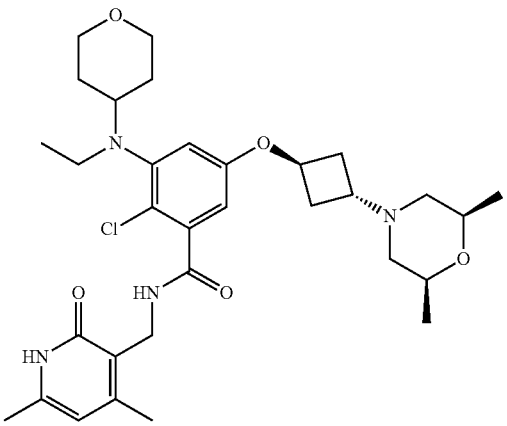

The title compound was prepared by referring to Example 1, Example 2, and Example 4.

m/z (ES+), [M+H]$^+$=601; HPLC $t_R$=1.411 min. 1H NMR (300 MHz, methanol-d$_4$) δ 6.75 (d, J=2.9 Hz, 1H), 6.58 (d, J=2.8 Hz, 1H), 6.13 (s, 1H), 4.78 (dt, J=6.9, 3.5 Hz, 1H), 4.49 (s, 2H), 3.95 (d, J=11.3 Hz, 2H), 3.75-3.63 (m, 2H), 3.39 (d, J=12.0 Hz, 2H), 3.31-3.09 (m, 3H), 3.02 (p, J=7.1 Hz, 1H), 2.85 (d, J=11.2 Hz, 2H), 2.45-2.40 (3, 5H), 2.30 (d, J=3.0 Hz, 1H), 2.26 (s, 4H), 1.78-1.65 (m, 4H), 1.57 (t, J=10.9 Hz, 2H), 1.17 (d, J=6.3 Hz, 6H), 0.91 (t, J=7.0 Hz, 3H).

Example 49: Preparation of the Compound 5-(trans-3-(8-oxa-3-azabicyclo[3.2.1]octan-3-yl) cyclobutoxy)-2-chloro-N-((4,6-dimethyl-2-oxo-1,2-dihydropyridin-3-yl)methyl)-3-(ethyl(tetrahydro-2H-pyran-4-yl)amino)benzamide (49)

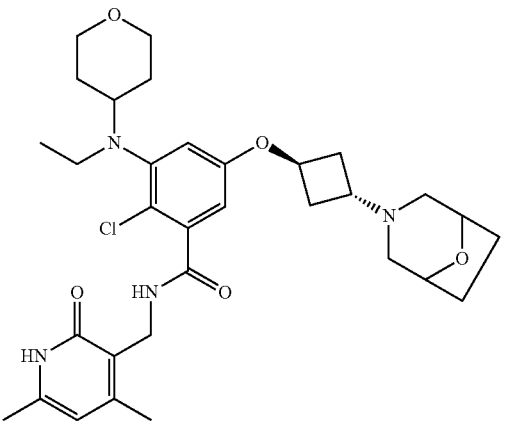 [SMILES: CCN(c1cc(O[C@H]2C[C@H](N3CC4CCC(C3)O4)C2)cc(C(=O)NCc2c(C)cc(C)[nH]c2=O)c1Cl)C1CCOCC1]

The title compound was prepared by referring to Example 1, Example 2, and Example 4.

m/z (ES+), [M/2+H]$^+$=300; HPLC $t_R$=0.988 min. 1H NMR (400 MHz, methanol-$d_4$) δ 0.91 (t, J=7.0 Hz, 3H), 1.62-1.81 (m, 4H), 1.86 (dd, J=8.0, 4.2 Hz, 2H), 1.95-2.03 (m, 2H), 2.09 (dd, J=11.4, 2.1 Hz, 2H), 2.17 (ddd, J=13.5, 7.6, 3.2 Hz, 2H), 2.26 (d, J=0.9 Hz, 3H), 2.39 (s, 5H), 2.69 (d, J=10.8 Hz, 2H), 3.02 (p, J=6.6 Hz, 1H), 3.14 (q, J=7.0 Hz, 2H), 3.25 (dq, J=9.5, 5.1, 4.6 Hz, 1H), 3.38 (dd, J=11.0, 3.0 Hz, 2H), 3.95 (d, J=11.6 Hz, 2H), 4.31 (dd, J=4.8, 2.4 Hz, 2H), 4.49 (s, 2H), 4.74 (dt, J=7.0, 3.5 Hz, 1H), 6.13 (s, 1H), 6.57 (d, J=2.8 Hz, 1H), 6.74 (d, J=2.9 Hz, 1H).

Example 50: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-(ethyl (1-(2,2,2-trifluoroethyl) piperidin-4-yl) amino)-2-methylbenzamide (50)

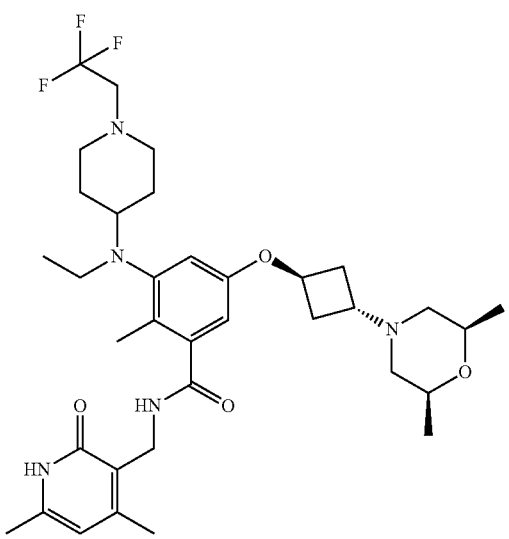

The title compound was prepared by referring to Example 1, Example 2, and Example 4.

m/z (ES+), [M+H]$^+$=332; HPLC $t_R$=0.959 min. 1H NMR (300 MHz, methanol-$d_4$) δ 6.72-6.66 (d, J=2.6 Hz, 1H), 6.53-6.51 (d, J=2.5 Hz, 1H), 6.16-6.12 (s, 1H), 4.80-4.73 (dd, J=6.5, 3.4 Hz, 1H), 4.50-4.44 (s, 2H), 3.76-3.64 (q, J=7.2, 6.0 Hz, 2H), 3.12-2.93 (td, J=16.8, 15.1, 8.9 Hz, 7H), 2.90-2.74 (t, J=10.4 Hz, 3H), 2.47-2.22 (d, J=39.9 Hz, 11H), 2.21-2.16 (s, 3H), 1.80-1.64 (d, J=21.7 Hz, 4H), 1.62-1.51 (t, J=10.9 Hz, 2H), 1.22-1.11 (d, J=6.2 Hz, 5H), 0.90-0.81 (t, J=6.9 Hz, 3H). 19 F NMR (282 MHz, methanol-$d_4$) δ −70.77--70.79.

Example 51: Preparation of the Compound N-((4,6-dimethyl-2-oxo-1,2-dihydropyridin-3-yl)methyl)-3-(ethyl(tetrahydro-2H-pyran-4-yl)amino)-N,2-dimethyl-5-(trans-3-morpholinylcyclobutoxy)benzamide (51)

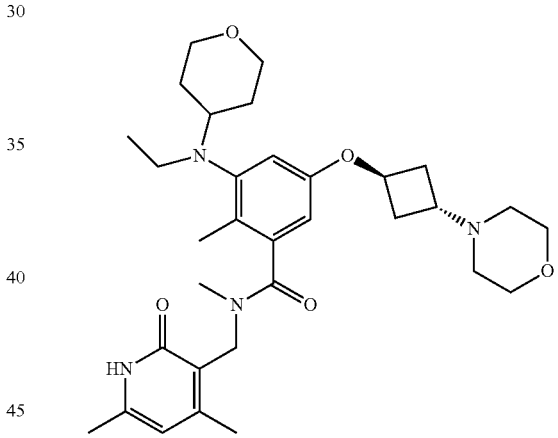

The title compound was prepared by referring to Example 1, Example 2, and Example 4.

m/z (ES+), [M+H]$^+$=567; HPLC $t_R$=0.860 min. 1H NMR (300 MHz, methanol-$d_4$) δ 6.74 (dd, J=10.0, 2.5 Hz, 1H), 6.41 (d, J=2.5 Hz, 1H), 6.15 (s, 1H), 4.80 (d, J=14.0 Hz, 2H), 4.71 (d, J=13.8 Hz, 1H), 3.93 (d, J=11.1 Hz, 2H), 3.74 (t, J=4.6 Hz, 4H), 3.39 (d, J=11.7 Hz, 2H), 3.14-3.00 (m, 2H), 3.00 (s, 1H), 2.75 (s, 2H), 2.40 (d, J=16.0 Hz, 8H), 2.26 (d, J=9.7 Hz, 5H), 2.14 (d, J=13.7 Hz, 3H), 1.98 (s, 1H), 1.74 (s, 3H), 1.61 (tt, J=11.8, 5.5 Hz, 2H), 0.89 (q, J=7.2 Hz, 3H).

Example 52: Preparation of the Compound N-((4,6-dimethyl-2-oxo-1,2-dihydropyridin-3-yl)methyl)-5-(trans-3-(cis-2,6-dimethylmorpholinyl)cyclobutoxy)-3-(ethyl(trans-4-((2-methoxyethyl)(methyl)amino)cyclohexyl)amino)-2-methylbenzamide (52)

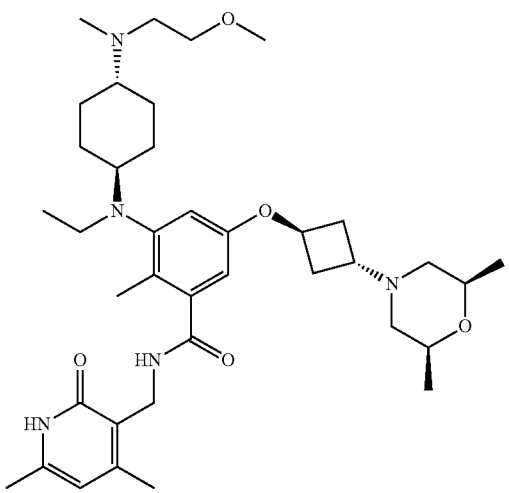

The title compound was prepared by referring to Example 1, Example 2, and Example 4.

m/z (ES+), [M+H]⁺=666; HPLC $t_R$=0.844 min. 1H NMR (300 MHz, methanol-$d_4$) δ 6.67 (d, J=2.6 Hz, 1H), 6.52 (d, J=2.5 Hz, 1H), 6.11 (s, 1H), 4.75 (dp, J=6.9, 3.2 Hz, 1H), 4.46 (s, 2H), 3.72-3.62 (m, 2H), 3.31-3.42 (m, 2H), 3.49 (t, J=5.9 Hz, 2H), 3.41 (s, 1H), 3.36 (s, 1H), 3.00 (dd, J=8.8, 6.2 Hz, 3H), 2.83 (dt, J=10.6, 1.8 Hz, 2H), 2.67 (t, J=5.9 Hz, 2H), 2.39 (s, 6H), 2.31-2.23 (m, 11H), 1.97 (d, J=11.3 Hz, 2H), 1.68-1.50 (m, 4H), 1.43 (d, J=10.6 Hz, 4H), 1.15 (d, J=6.3 Hz, 6H), 0.87 (t, J=6.9 Hz, 3H).

Example 53: Preparation of the Compound 2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)benzamide (53)

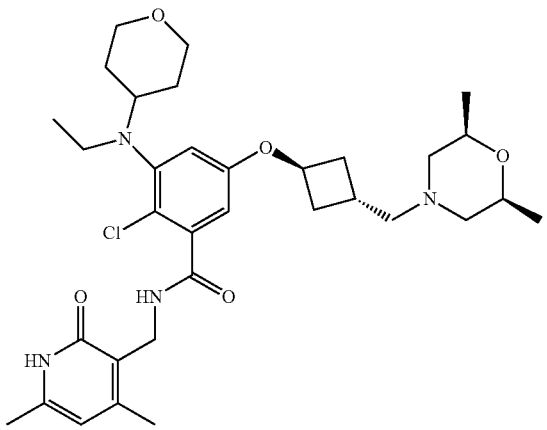

The title compound was prepared by referring to Example 1, Example 2, and Example 4.

m/z (ES+), [M+H]⁺=615; HPLC $t_R$=1.061 min. ¹H NMR (300 MHz, methanol-$d_4$) δ 6.73 (d, J=2.9 Hz, 1H), 6.57 (d, J=2.8 Hz, 1H), 6.12 (s, 1H), 4.79 (q, J=5.8 Hz, 1H), 4.48 (s, 2H), 3.95 (d, J=11.4 Hz, 2H), 3.77-3.63 (m, 2H), 3.44-3.34 (m, 2H), 3.25 (dd, J=9.9, 4.7 Hz, 1H), 3.14 (q, J=7.0 Hz, 2H), 2.78 (d, J=11.3 Hz, 2H), 2.66 (q, J=7.1 Hz, 1H), 2.53 (d, J=7.4 Hz, 2H), 2.39 (s, 3H), 2.33-2.23 (m, 7H), 1.83-1.59 (m, 6H), 1.14 (d, J=6.3 Hz, 6H), 0.91 (t, J=7.0 Hz, 3H).

Example 54: Preparation of the Compound 5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide (54)

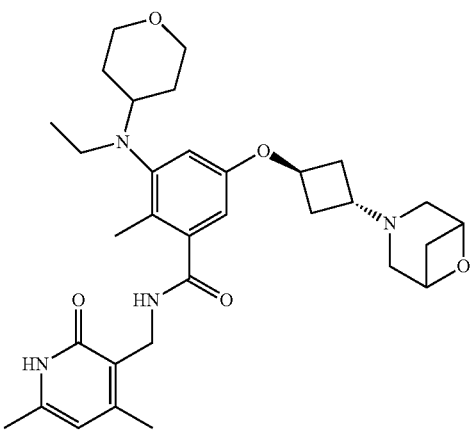 [SMILES: CCN(c1cc(O[C@H]2C[C@H](N3CC4CC(C3)O4)C2)cc(C(=O)NCc2c(C)cc(C)[nH]c2=O)c1C)C1CCOCC1]

The title compound was prepared by referring to Example 1, Example 2, and Example 4.

m/z (ES+), [M+H]⁺=565; HPLC $t_R$=1.511 min. ¹H NMR (400 MHz, methanol-$d_4$) δ 0.87 (t, J=7.0 Hz, 3H), 1.63 (qd, J=11.7, 4.3 Hz, 2H), 1.73 (d, J=12.6 Hz, 2H), 2.21 (s, 3H), 2.23-2.31 (m, 4H), 2.35 (d, J=8.2 Hz, 1H), 2.40 (s, 3H), 2.55 (dt, J=13.0, 6.4 Hz, 2H), 2.66 (d, J=11.6 Hz, 2H), DE2.97-3.13 (m, 3H), 3.19 (d, J=11.7 Hz, 2H), 3.38 (dd, J=11.6, 2.2 Hz, 2H), 3.43-3.54 (m, 1H), 3.93 (d, J=11.6 Hz, 2H), 4.47 (s, 2H), 4.57 (d, J=6.2 Hz, 2H), 4.80 (dq, J=7.0, 3.5 Hz, 1H), 6.13 (s, 1H), 6.55 (d, J=2.5 Hz, 1H), 6.73 (d, J=2.6 Hz, 1H).

Example 55: Preparation of the Compound 5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)benzamide (55)

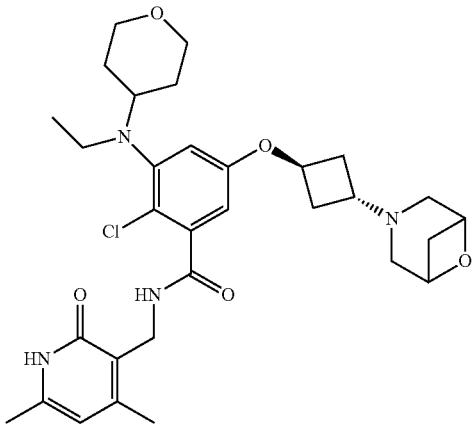

The title compound was prepared by referring to Example 1, Example 2, and Example 4.

m/z (ES+), [M+H]$^+$=585; HPLC $t_R$=1.495 min. $^1$H NMR (300 MHz, methanol-$d_4$) δ 6.74 (d, J=2.9 Hz, 1H), 6.59 (d, J=2.8 Hz, 1H), 6.11 (s, 1H), 4.83-4.76 (m, 1H), 4.58 (d, J=6.2 Hz, 2H), 4.49 (s, 2H), 3.96 (d, J=11.5 Hz, 2H), 3.48 (t, J=6.8 Hz, 1H), 3.44-3.34 (m, 2H), 3.30-3.23 (m, 1H), 3.23-3.10 (m, 4H), 3.05 (q, J=6.8 Hz, 1H), 2.67 (d, J=11.6 Hz, 2H), 2.56 (dt, J=12.8, 6.6 Hz, 2H), 2.40 (s, 3H), 2.38-2.23 (m, 5H), 1.80-1.66 (m, 3H), 0.91 (t, J=7.0 Hz, 3H).

Example 56: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperidin-1-yl)cyclobutoxy)benzamide (56)

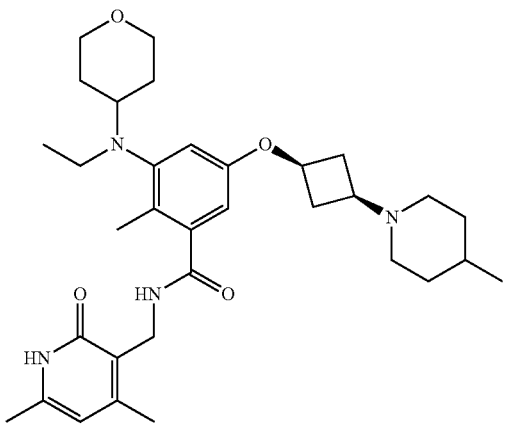

The title compound was prepared by referring to Example 1, Example 2, and Example 4.

m/z (ES+), [M+H]$^+$=565; HPLC $t_R$=1.565 min. $^1$H NMR (400 MHz, methanol-$d_4$) δ 0.86 (t, J=6.9 Hz, 2H), 0.96 (d, J=6.4 Hz, 2H), 1.28 (d, J=22.4 Hz, 2H), 1.42 (s, 1H), 1.67 (dt, J=23.8, 11.2 Hz, 5H), 1.87 (d, J=11.9 Hz, 1H), 1.93-2.03 (m, 2H), 2.39 (s, 2H), 2.48-2.56 (m, 1H), 2.70 (d, J=7.0 Hz, 1H), 2.91 (d, J=11.4 Hz, 1H), 3.05 (dd, J=15.8, 8.9 Hz, 2H), 3.36-3.40 (m, 2H), 3.93 (d, J=11.4 Hz, 2H), 4.46 (d, J=5.7 Hz, 2H), 6.13 (s, 1H), 6.58 (d, J=2.5 Hz, 1H), 6.73 (d, J=2.5 Hz, 1H).

Example 57: Preparation of the Compound N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydro-2H-pyran-4-yl)amino)benzamide (57)

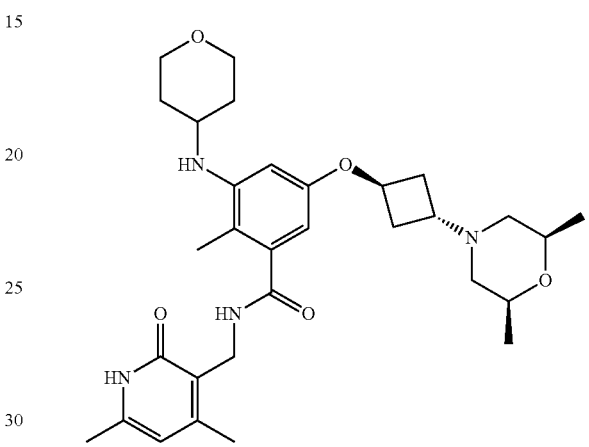

The title compound was prepared by referring to Example 1, Example 2, and Example 4.

m/z (ES+), [M+H]$^+$=553; HPLC $t_R$=1.213 min. $^1$H NMR (400 MHz, methanol-$d_4$) δ 6.24-6.21 (d, J=2.4 Hz, 1H), 6.14-6.11 (s, 1H), 6.06-6.03 (d, J=2.4 Hz, 1H), 4.78-4.71 (dt, J=6.8, 3.5 Hz, 1H), 4.48-4.44 (s, 2H), 4.04-3.94 (d, J=11.0 Hz, 2H), 3.74-3.65 (dt, J=14.8, 6.5 Hz, 2H), 3.60-3.49 (m, 3H), 3.03-2.96 (q, J=7.1 Hz, 1H), 2.87-2.81 (d, J=11.3 Hz, 2H), 2.43-2.35 (s, 5H), 2.29-2.20 (s, 5H), 2.05-1.97 (s, 5H), 1.63-1.51 (t, J=11.0 Hz, 4H), 1.20-1.14 (d, J=6.3 Hz, 6H).

Example 58: Preparation of the Compound N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydrofuran-3-yl)amino)benzamide (58)

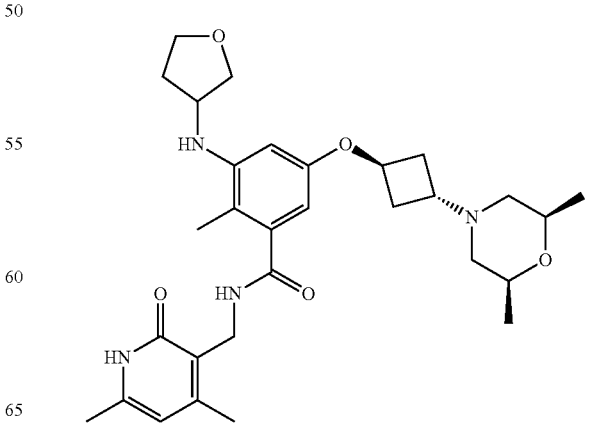

The title compound was prepared by referring to Example 1, Example 2, and Example 4.

m/z (ES+), [M+H]⁺=539; HPLC $t_R$=1.188 min. ¹H NMR (400 MHz, methanol-$d_4$) δ 6.16-6.11 (m, 2H), 6.09-6.07 (d, J=2.4 Hz, 1H), 4.79-4.71 (dt, J=7.0, 3.7 Hz, 1H), 4.48-4.45 (s, 2H), 4.14-4.07 (dt, J=6.5, 3.3 Hz, 1H), 4.02-3.93 (m, 2H), 3.89-3.81 (td, J=8.2, 5.6 Hz, 1H), 3.74-3.65 (m, 3H), 3.03-2.94 (q, J=7.1 Hz, 1H), 2.87-2.81 (d, J=11.2 Hz, 2H), 2.47-2.35 (s, 5H), 2.35-2.20 (m, 6H), 2.05-2.00 (s, 3H), 1.97-1.89 (m, 1H), 1.60-1.52 (t, J=10.9 Hz, 2H), 1.19-1.12 (d, J=6.3 Hz, 6H).

Example 59: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(4-methylpiperidin-1-yl)cyclobutoxy)benzamide (59)

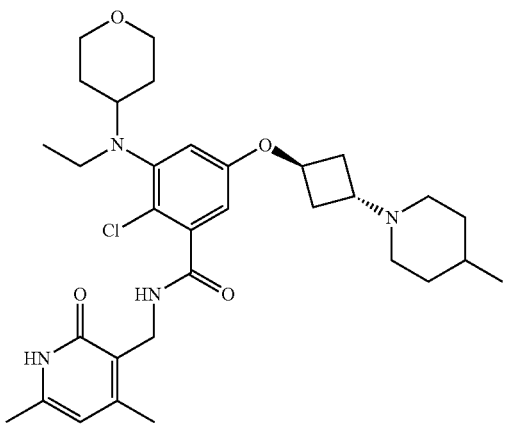

The title compound was prepared by referring to Example 1, Example 2, and Example 4.

m/z (ES+), [M+H]⁺=585 & [M/2+H]⁺=293; HPLC $t_R$=1.087 min. ¹H NMR (400 MHz, methanol-$d_4$) δ 6.75 (d, J=2.9 Hz, 1H), 6.57 (d, J=2.8 Hz, 1H), 6.13 (s, 1H), 4.77 (t, J=6.7 Hz, 1H), 4.49 (s, 2H), 3.95 (d, J=11.5 Hz, 2H), 3.41-3.35 (m, 2H), 3.26 (dq, J=9.6, 5.2, 4.7 Hz, 1H), 3.15 (q, J=7.0 Hz, 2H), 3.04 (t, J=7.5 Hz, 1H), 2.93 (d, J=11.3 Hz, 2H), 2.39 (s, 5H), 2.32-2.22 (m, 5H), 1.89-1.64 (m, 8H), 1.44 (d, J=11.3 Hz, 1H), 1.33-1.19 (m, 2H), 0.98 (d, J=6.5 Hz, 3H), 0.91 (t, J=7.0 Hz, 3H).

Example 60: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-ylmethyl)cyclobutoxy)benzamide (60)

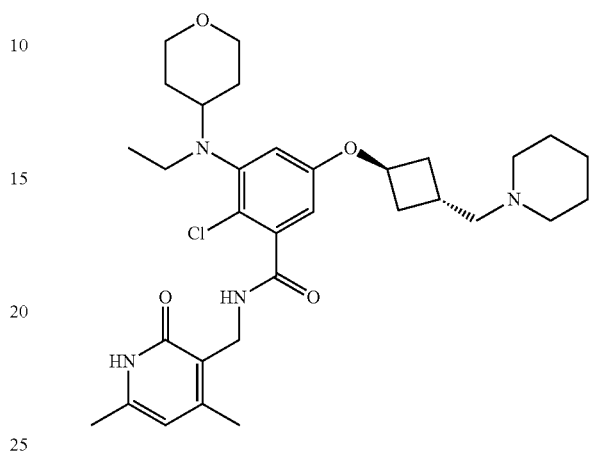

The title compound was prepared by referring to Example 1, Example 2, and Example 4.

m/z (ES+), [M+H]⁺=585; HPLC $t_R$=1.038 min. 1H NMR (300 MHz, methanol-d4) δ 6.74 (d, J=2.8 Hz, 1H), 6.57 (d, J=2.8 Hz, 1H), 6.13 (s, 1H), 4.82-4.72 (m, 1H), 4.49 (s, 2H), 3.95 (d, J=11.4 Hz, 2H), 3.38 (dd, J=10.8, 3.1 Hz, 2H), 3.31-3.08 (m, 3H), 2.70 (p, J=7.1 Hz, 1H), 2.56 (d, J=7.1 Hz, 2H), 2.47 (s, 4H), 2.39 (s, 3H), 2.27 (d, J=5.6 Hz, 7H), 1.68 (dq, J=34.5, 5.3, 4.7 Hz, 8H), 1.50 (d, J=7.0 Hz, 2H), 0.91 (t, J=7.0 Hz, 3H).

Example 61: Preparation of the Compound N-((4,6-dimethyl-2-oxo-1,2-dihydropyridin-3-yl)methyl)-3-(ethyl(tetrahydro-2H-pyran-4-yl)amino)-2-fluoro-5-(trans-3-(morpholinomethyl)cyclobutoxy)benzamide (61)

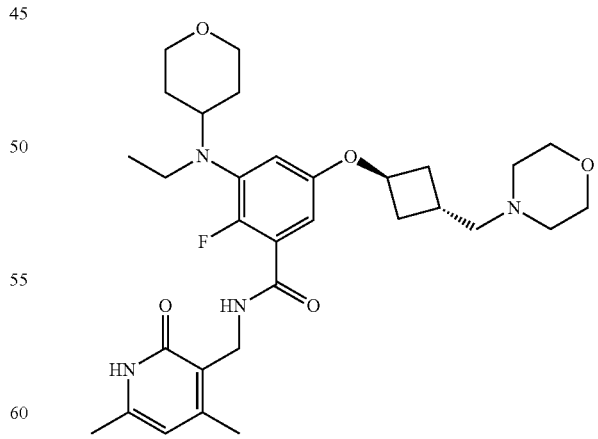

The title compound was prepared by referring to Example 1, Example 2, and Example 4.

m/z (ES+), [M+H]⁺=571 & [M/2+H]⁺=286; HPLC $t_R$=0.816 min. ¹H NMR (300 MHz, methanol-$d_4$) δ 6.90 (d, J=5.6 Hz, 2H), 6.15 (s, 1H), 4.85 (d, J=5.7 Hz, 1H), 4.51 (s, 2H), 4.03 (dd, J=27.9, 12.4 Hz, 4H), 3.78 (t, J=12.5 Hz, 2H), 3.51-3.35 (m, 9H), 3.18 (t, J=11.7 Hz, 2H), 2.99-2.88 (m, 1H), 2.50-2.42 (m, 4H), 2.39 (s, 3H), 2.27 (s, 3H), 1.85-1.66 (m, 4H), 1.02 (t, J=7.0 Hz, 3H).

Example 62: Preparation of the Compound N-((4,6-dimethyl-2-oxo-1,2-dihydropyridin-3-yl)methyl)-3-(ethyl(tetrahydro-2H-pyran-4-yl)amino)-2-fluoro-5-(trans-3-morpholinocyclobutoxy)benzamide (62)

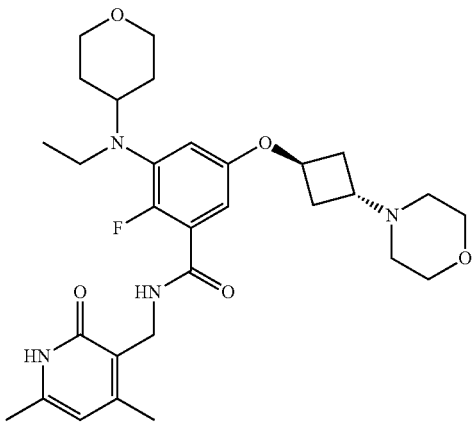 [SMILES: CCN(c1cc(O[C@H]2C[C@H](N3CCOCC3)C2)cc(C(=O)NCc2c(C)cc(C)[nH]c2=O)c1F)C1CCOCC1]

The title compound was prepared by referring to Example 1, Example 2, and Example 4.

m/z (ES+), [M+H]$^+$=557; HPLC $t_R$=1.426 min. $^1$H NMR (300 MHz, methanol-$d_4$) δ 1.05 (t, J=7.0 Hz, 3H), 1.75 (td, J=11.7, 4.2 Hz, 2H), 1.86 (d, J=12.1 Hz, 2H), 2.21-2.33 (m, 3H), 2.40 (s, 3H), 2.62 (t, J=10.6 Hz, 2H), 2.86 (dt, J=14.4, 7.1 Hz, 2H), 3.05 (s, 2H), 3.37-3.63 (m, 7H), 3.73 (dt, J=24.2, 11.7 Hz, 3H), 3.94-4.22 (m, 5H), 4.52 (s, 2H), 6.18 (s, 1H), 7.05 (ddd, J=17.7, 5.6, 3.1 Hz, 2H).

Example 63: Preparation of the Compound 3-((4,4-difluorocyclohexyl)(ethyl)amino)-N-((4,6-dimethyl-2-oxo-1,2-dihydropyridin-3-yl)methyl)-2-methyl-5-(trans-3-morpholinocyclobutoxy)benzamide (63)

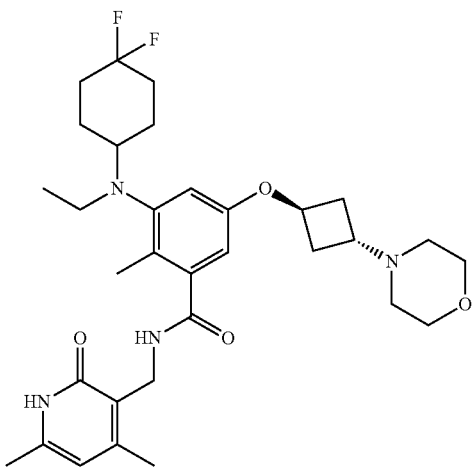 [SMILES: CCN(c1cc(O[C@H]2C[C@H](N3CCOCC3)C2)cc(C(=O)NCc2c(C)cc(C)[nH]c2=O)c1C)C1CCC(F)(F)CC1]

The title compound was prepared by referring to Example 1 with tetrahydropyran-4-one replaced by 4,4-difluorocyclohexanone and referring to Example 4.

m/z (ES+), [M+H]$^+$=587; HPLC $t_R$=1.412 min. $^1$H NMR (300 MHz, methanol-$d_4$) δ 6.71 (d, J=2.5 Hz, 1H), 6.53 (d, J=2.6 Hz, 1H), 6.13 (s, 1H), 4.75 (s, 1H), 4.47 (s, 2H), 3.74 (t, J=4.7 Hz, 4H), 3.05 (s, 4H), 2.41 (d, J=8.7 Hz, 9H), 2.23 (d, J=19.7 Hz, 8H), 2.01 (s, 2H), 1.83-1.69 (m, 6H), 0.88 (t, J=7.0 Hz, 3H).

Example 64: Preparation of the Compound N-((4,6-dimethyl-2-oxo-1,2-dihydropyridin-3-yl)methyl)-3-(ethyl(tetrahydrofuran-3-yl)amino)-2-methyl-5-(trans-3-morpholin-4-ylcyclobutoxy)benzamide (64)

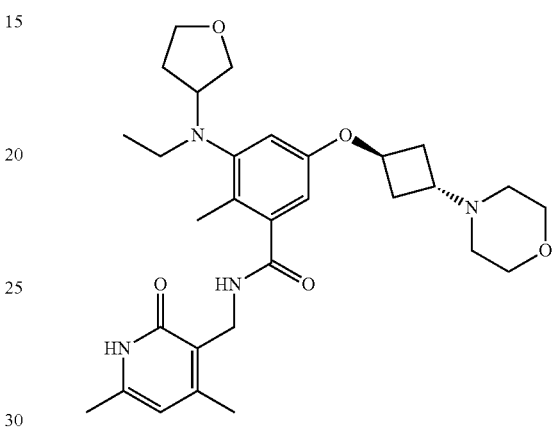

The title compound was prepared by referring to Example 1, Example 2, and Example 4.

m/z (ES+), [M+H]$^+$=539; HPLC $t_R$=1.449 min. $^1$H NMR (300 MHz, methanol-$d_4$) δ 6.75 (d, J=2.6 Hz, 1H), 6.56 (d, J=2.5 Hz, 1H), 6.13 (s, 1H), 4.77 (dd, J=6.8, 3.5 Hz, 1H), 4.47 (s, 2H), 3.98-3.69 (m, 8H), 3.57-3.48 (m, 1H), 3.02 (p, J=7.1 Hz, 3H), 2.39 (m, 4H), 2.24 (d, J=14.2 Hz, 8H), 2.08-1.96 (m, 2H), 0.88 (t, J=7.1 Hz, 3H).

Example 65: Preparation of the Compound 2-chloro-3-((4,4-difluorocyclohexyl) (ethyl)amino)-N-((4,6-dimethyl-2-oxo-1,2-dihydropyridin-3-yl)methyl)-5-(trans-3-(4-methylpiperidin-1-yl)cyclobutoxy)benzamide (65)

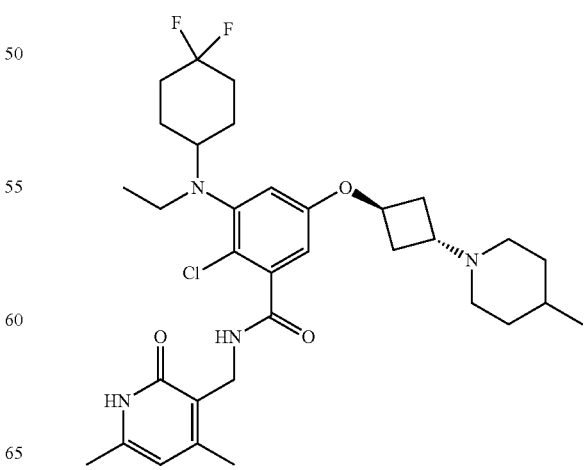

The title compound was prepared by referring to Example 1, Example 2, and Example 4.

m/z (ES+), [M+H]$^+$=619; HPLC $t_R$=2.287 min. $^1$H NMR (300 MHz, methanol-$d_4$) δ 6.75 (d, J=2.8 Hz, 1H), 6.58 (d, J=2.8 Hz, 1H), 6.13 (s, 1H), 4.77 (s, 1H), 4.49 (s, 1H), 3.21-2.99 (m, 2H), 2.94 (d, J=11.2 Hz, 1H), 2.39 (s, 3H), 2.26 (s, 4H), 2.06 (s, 2H), 1.80 (dq, J=24.9, 13.8, 13.3 Hz, 7H), 1.49-1.16 (m, 6H), 1.05-0.85 (m, 5H).

Example 66: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-yl)cyclobutoxy)benzamide (66)

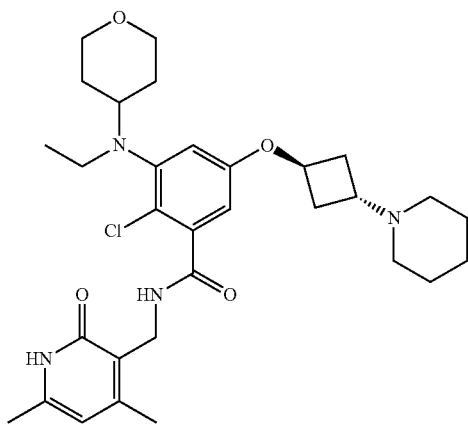 [SMILES: CCN(c1cc(O[C@H]2C[C@H](N3CCCCC3)C2)cc(C(=O)NCc2c(C)cc(C)[nH]c2=O)c1Cl)C1CCOCC1]

The title compound was prepared by referring to Example 1, Example 2, and Example 4.

m/z (ES+), [M+H]$^+$=571.31; HPLC $t_R$=6.501 min. $^1$H NMR (400 MHz, DMSO) δ 11.45 (s, 1H), 8.21 (t, J=4.9 Hz, 1H), 6.66 (d, J=2.8 Hz, 1H), 6.42 (d, J=2.8 Hz, 1H), 5.86 (s, 1H), 4.70 (dd, J=6.7, 3.3 Hz, 1H), 4.26 (d, J=5.0 Hz, 2H), 3.84 (d, J=11.2 Hz, 2H), 3.23 (t, J=10.6 Hz, 2H), 3.16 (t, J=6.5 Hz, 3H), 3.06 (q, J=6.9 Hz, 2H), 2.88-2.79 (m, 1H), 2.38-2.02 (m, 14H), 1.69-1.32 (m, 10H), 0.82 (t, J=6.9 Hz, 3H).

Example 67: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(trans-3-(4,4-difluoropiperidin-1-yl)cyclobutoxy)benzamide (67)

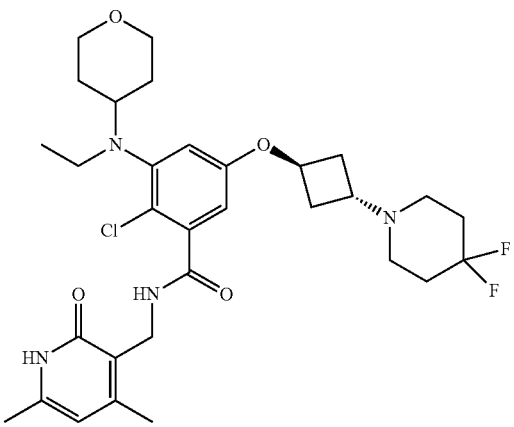 [SMILES: CCN(c1cc(O[C@H]2C[C@H](N3CCC(F)(F)CC3)C2)cc(C(=O)NCc2c(C)cc(C)[nH]c2=O)c1Cl)C1CCOCC1]

The title compound was prepared by referring to Example 1, Example 2, and Example 4.

m/z (ES+), [M+H]$^+$=607.17; HPLC $t_R$=7.741 min. $^1$H NMR (400 MHz, DMSO) δ 11.46 (s, 1H), 8.22 (d, J=5.0 Hz, 1H), 6.67 (d, J=2.8 Hz, 1H), 6.42 (d, J=2.8 Hz, 1H), 5.86 (s, 1H), 4.73 (d, J=3.6 Hz, 1H), 4.26 (d, J=4.9 Hz, 2H), 3.84 (d, J=11.2 Hz, 2H), 3.27-2.96 (m, 6H), 2.43-2.28 (m, 6H), 2.22-2.03 (m, 7H), 1.95 (m, 4H), 1.59 (m, 4H), 0.83 (dd, J=14.2, 7.2 Hz, 3H).

Example 68: Preparation of the Compound 3-((4,4-difluorocyclohexyl)(ethyl)amino)-N-((4,6-dimethyl-2-oxo-1,2-dihydropyridin-3-yl)methyl)-2-methyl-5-(trans-3-(piperidin-1-yl)cyclobutoxy)benzamide (68)

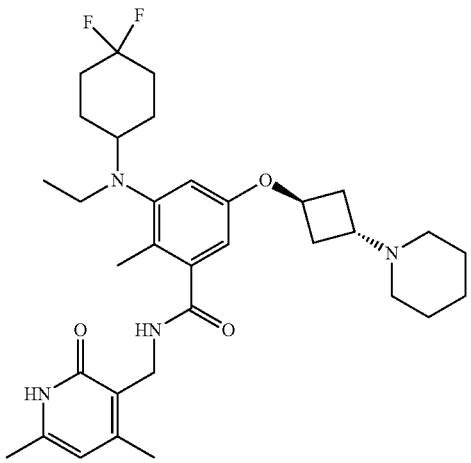 [SMILES: CCN(c1cc(O[C@H]2C[C@H](N3CCCCC3)C2)cc(C(=O)NCc2c(C)cc(C)[nH]c2=O)c1C)C1CCC(F)(F)CC1]

The title compound was prepared by referring to Example 1 with tetrahydropyran-4-one replaced by 4,4-difluorocyclohexanone and cyclobutanol replaced by 1,3-cis-3-(piperidin-1-yl) cyclobutyl-1-ol. 1,3-cis-3-(piperidin-1-yl)cyclobutyl-1-ol was prepared by referring to Example 4.

m/z (ES+), [M+H]⁺=585.30; HPLC $t_R$=4.639 min. ¹H NMR (400 MHz, CDCl₃) δ 7.17 (s, 1H), 6.60 (d, J=2.4 Hz, 1H), 6.46 (d, J=2.4 Hz, 1H), 5.91 (s, 1H), 4.69 (dd, J=8.3, 5.5 Hz, 1H), 4.50 (d, J=6.0 Hz, 2H), 3.10-2.86 (m, 5H), 2.54 (s, 3H), 2.48-2.15 (m, 20H), 2.04 (d, J=6.9 Hz, 3H), 1.85-1.56 (m, 13H), 0.86 (q, J=6.7 Hz, 3H).

Example 69: Preparation of the Compound 2-chloro-3-((4,4-difluorocyclohexyl)(ethyl) amino)-N-((4,6-dimethyl-2-oxo-1,2-dihydropyridin-3-yl)methyl)-5-(trans-3-(cis-2,6-dimethylmorpholino)cyclobutoxy)benzamide (69)

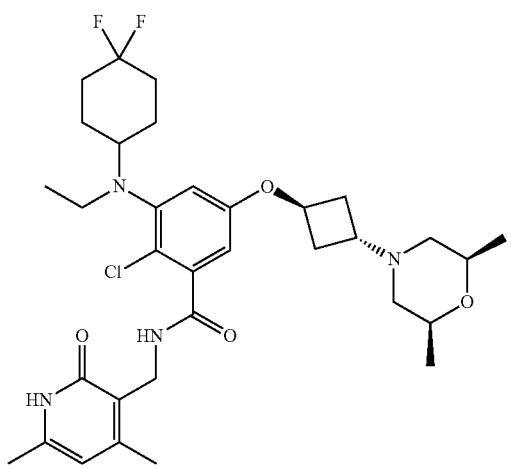

The title compound was prepared by referring to Example 1, Example 2, and Example 4.

m/z (ES+), [M+H]⁺=635; HPLC $t_R$=1.876 min. ¹H NMR (400 MHz, methanol-d₄) δ 6.78 (d, J=2.9 Hz, 1H), 6.64 (d, J=2.9 Hz, 1H), 6.13 (s, 1H), 4.50 (d, J=9.9 Hz, 2H), 3.75-3.60 (m, 1H), 3.12 (t, J=7.0 Hz, 2H), 2.79 (d, J=11.0 Hz, 1H), 2.71 (ddt, J=11.5, 8.8, 4.4 Hz, 1H), 2.52 (p, J=7.9 Hz, 1H), 2.39 (s, 2H), 2.26 (d, J=0.9 Hz, 2H), 2.12-1.92 (m, 3H), 1.91-1.69 (m, 4H), 1.60 (t, J=10.9 Hz, 2H), 1.15 (d, J=6.3 Hz, 4H), 0.91 (t, J=7.0 Hz, 2H).

Example 70: Preparation of the Compound 2-chloro-3-((4,4-difluorocyclohexyl) (ethyl)amino)-N-((4,6-dimethyl-2-oxo-1,2-dihydropyridin-3-yl)methyl)-5-(cis-3-(4-methylpiperidin-1-yl)cyclobutoxy)benzamide (70)

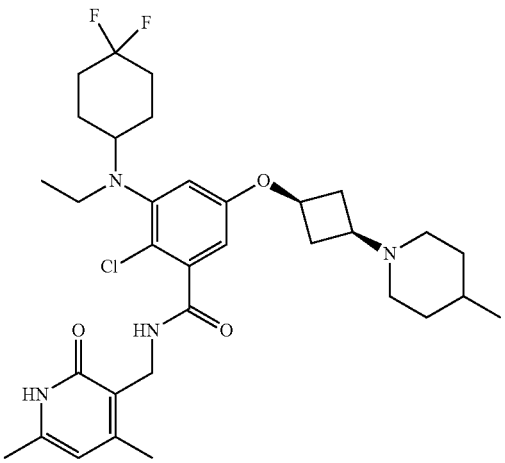

The title compound was prepared by referring to Example 1, Example 2, and Example 4.

m/z (ES+), [M+H]⁺=619; HPLC $t_R$=2.026 min. ¹H NMR (300 MHz, methanol-d₄) δ 6.75 (d, J=2.8 Hz, 1H), 6.56 (d, J=2.8 Hz, 1H), 6.12 (s, 1H), 4.76 (s, 2H), 3.22-3.01 (m, 2H), 2.96-2.84 (m, 2H), 2.80-2.65 (m, 2H), 2.36 (s, 3H), 2.23 (s, 3H), 2.12-1.98 (m, 4H), 1.86-1.55 (m, 8H), 1.50-1.23 (m, 8H), 1.05-0.86 (m, 6H).

Example 71: Preparation of the Compound N-((4,6-dimethyl-2-oxo-1,2-dihydropyridin-3-yl)methyl)-3-(ethyl(tetrahydro-2H-pyran-4-yl)amino)-5-(2-(hydroxymethyl)cyclopropyl)-2-methylbenzamide (71)

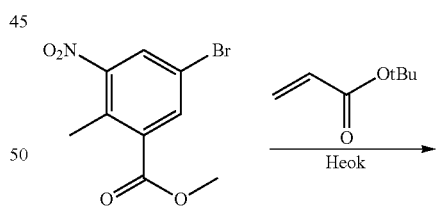

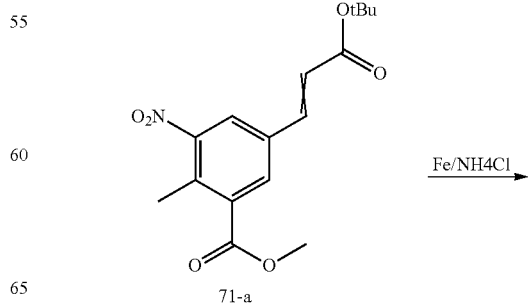

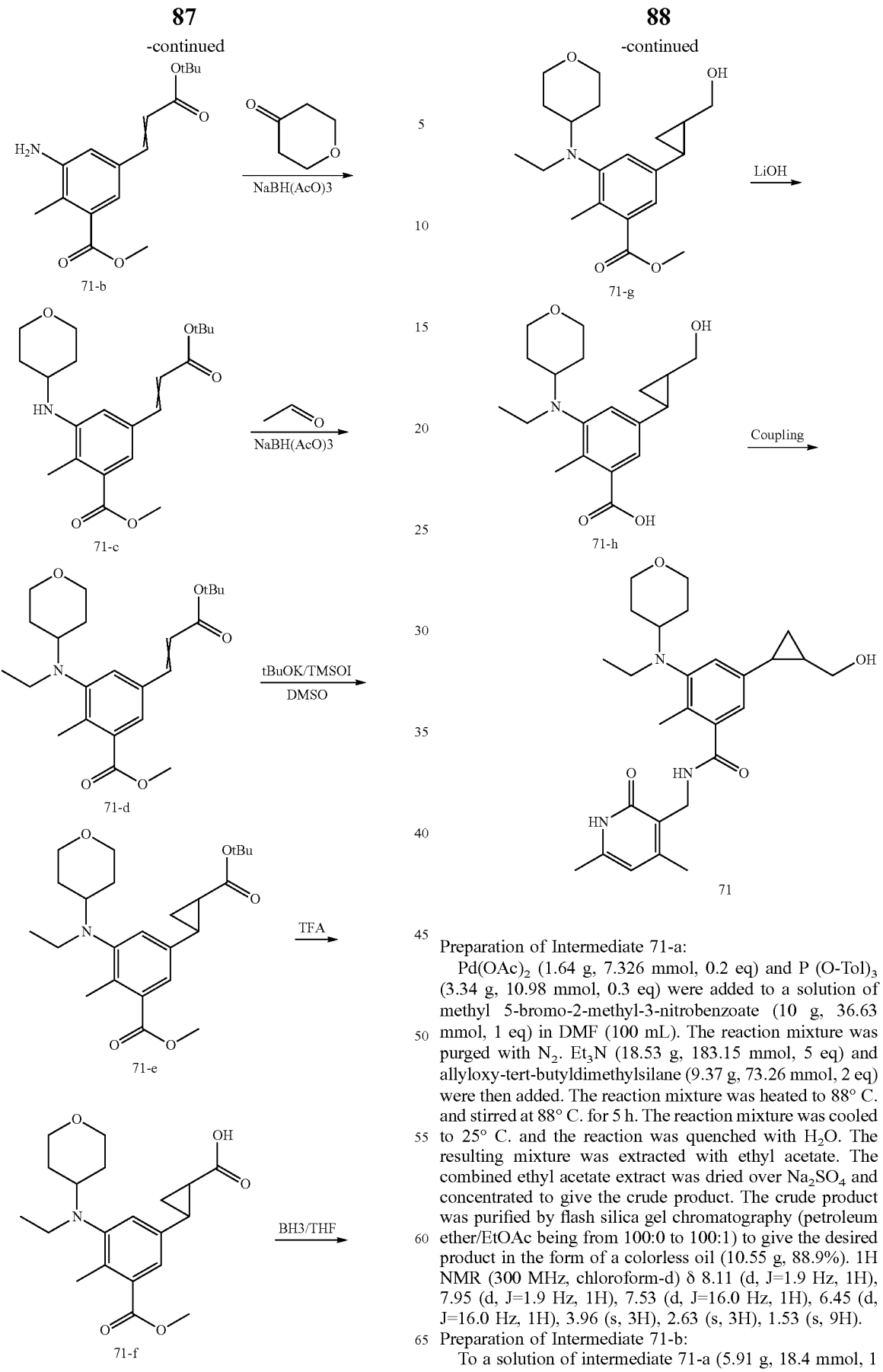

Preparation of Intermediate 71-a:

Pd(OAc)$_2$ (1.64 g, 7.326 mmol, 0.2 eq) and P (O-Tol)$_3$ (3.34 g, 10.98 mmol, 0.3 eq) were added to a solution of methyl 5-bromo-2-methyl-3-nitrobenzoate (10 g, 36.63 mmol, 1 eq) in DMF (100 mL). The reaction mixture was purged with N$_2$. Et$_3$N (18.53 g, 183.15 mmol, 5 eq) and allyloxy-tert-butyldimethylsilane (9.37 g, 73.26 mmol, 2 eq) were then added. The reaction mixture was heated to 88° C. and stirred at 88° C. for 5 h. The reaction mixture was cooled to 25° C. and the reaction was quenched with H$_2$O. The resulting mixture was extracted with ethyl acetate. The combined ethyl acetate extract was dried over Na$_2$SO$_4$ and concentrated to give the crude product. The crude product was purified by flash silica gel chromatography (petroleum ether/EtOAc being from 100:0 to 100:1) to give the desired product in the form of a colorless oil (10.55 g, 88.9%). 1H NMR (300 MHz, chloroform-d) δ 8.11 (d, J=1.9 Hz, 1H), 7.95 (d, J=1.9 Hz, 1H), 7.53 (d, J=16.0 Hz, 1H), 6.45 (d, J=16.0 Hz, 1H), 3.96 (s, 3H), 2.63 (s, 3H), 1.53 (s, 9H).

Preparation of Intermediate 71-b:

To a solution of intermediate 71-a (5.91 g, 18.4 mmol, 1 eq) in ethanol (60 mL) was added an aqueous ammonium chloride (3.9 g, 73.6 mmol, 4 eq) solution (15 mL) with stirring. Iron powder (10.3 g, 184.1 mmol, 10 eq) was added with stirring. The resulting reaction mixture was stirred at 80° C. for 1 h. After the reaction was completed, water was added to the reaction mixture, and the reaction mixture was filtered through celite, and the filtrate was extracted with ethyl acetate. The combined organic phases were washed with water, dried and concentrated under reduced pressure to give the desired compound. This compound was used in the next step without further purification. m/z (ES+), [M+H]$^+$=292; HPLC $t_R$=1.321 min. 1H NMR (300 MHz, chloroform-d) δ 7.55-7.39 (m, 2H), 6.97 (s, 1H), 6.35 (d, J=16.0 Hz, 1H), 3.92 (s, 3H), 2.38 (s, 3H), 1.55 (s, 9H).

Preparation of Intermediate 71-d:

To a solution of intermediate 71-b (7.08 g, 24.3 mmol, 1 eq) and tetrahydro-4H-pyran-4-one (9.73 g, 97.3 mmol, 4 eq) in methanol (80 mL) was added acetic acid (8.76 g, 145.9 mmol, 6 eq) with stirring. The reaction mixture was stirred at room temperature for 1 h. Sodium cyanoborohydride (4.60 g, 72.9 mmol, 3 eq) was then added and the reaction mixture was stirred at room temperature for an additional 2 h. After the reaction was completed, acetaldehyde (10.9 mL, 194.6 mmol, 8 eq) and sodium triacetoxyborohydride (20.6 g, 97.3 mmol, 4 eq) were added and the Mitsunobo reaction was continued. After the reaction was completed, the reaction mixture was extracted with ethyl acetate and washed with a saturated aqueous sodium bicarbonate solution. The organic phase was concentrated and purified by silica gel column chromatography to give intermediate 71-d (5.07 g, 51.7%). m/z (ES+), [M+H]$^+$=404; HPLC $t_R$=1.392 min. 1H NMR (400 MHz, DMSO-d$_6$) δ 7.77-7.71 (m, 2H), 7.55 (d, J=16.0 Hz, 1H), 6.58 (d, J=16.0 Hz, 1H), 3.88-3.76 (m, 5H), 3.24 (dd, J=11.6, 2.1 Hz, 2H), 3.12-3.00 (m, 3H), 2.42 (s, 3H), 1.70-1.55 (m, 2H), 1.49 (s, 11H), 0.78 (t, J=6.9 Hz, 3H).

Preparation of Intermediate 71-e:

In a three-necked flask with a balloon, t-BuOK (4.23 g, 37.71 mmol, 3 eq) was added to trimethylsulfonium iodide (8.3 g, 37.71 mmol, 3 eq) in anhydrous DMSO (30 mL) under N$_2$ atmosphere. The mixture was stirred at room temperature for 30 min. A solution of intermediate 77-d (5.07 g, 12.57 mmol, 1 eq) in DMSO (5 mL) was then added dropwise. The reaction mixture was stirred at room temperature for 3 h, and then hydrolyzed with a saturated aqueous ammonium chloride solution. The aqueous phase was extracted with ether. The organic phase was concentrated and purified by silica gel column chromatography to give intermediate 71-e (3.16 g, 60.3%). m/z (ES+), [M+H]$^+$=418; HPLC $t_R$=0.994 min. 1H NMR (400 MHz, chloroform-d) δ 7.25 (d, J=1.9 Hz, 1H), 7.05 (d, J=1.9 Hz, 1H), 3.97 (d, J=11.5 Hz, 2H), 3.90 (s, 3H), 3.34 (td, J=11.4, 2.8 Hz, 2H), 3.07 (d, J=7.1 Hz, 2H), 2.92 (d, J=25.8 Hz, 1H), 2.51-2.37 (m, 4H), 1.83 (ddd, J=8.4, 5.3, 4.2 Hz, 1H), 1.76-1.61 (m, 4H), 1.54 (dd, J=9.3, 4.7 Hz, 10H), 1.27-1.15 (m, 1H), 0.87 (t, J=7.0 Hz, 3H).

Preparation of Intermediate 71-f:

Intermediate 77-e (3.16 g, 7.58 mmol) was dissolved in TFA/DCM (5 mL/30 mL). The resulting solution was stirred at room temperature for 2 h and concentrated under reduced pressure to give the desired compound 71-f (3.5 g, crude), which was used in the next step without further purification. m/z (ES+), [M+H]$^+$=362; HPLC tR=0.807 min.

Preparation of Intermediate 71-g:

Intermediate 77-f (3.5 g, crude) was dissolved in THF (30 mL) and BH$_3$ THF (20 mL, 20 mmol) was added dropwise. The reaction mixture was stirred at room temperature for 1 h. After the reaction was completed, the mixture was carefully treated with 1N HCl until pH=2. The mixture was stirred at room temperature for 1 h. The solvent was then concentrated under reduced pressure. The aqueous phase was extracted with ethyl acetate (50 mL×3). The organic phase was concentrated to give the desired compound 71-g (7 g, crude). The crude product was used directly in the next step without purification. m/z (ES+), [M+H]$^+$=348; HPLC $t_R$=0.675 min. Based on SFC (CHIRALPAK AS-3 3.0×100 mm 3 um; column: 4-A-10%-50%-6.5 min-2 mL. 1 cm; MeOH: 20 mM NH$_3$), the ratio of the two isomers was (46.2:51.0).

Preparation of Intermediate 71-h:

LiOH (56 mg, 2.3 mmol, 10 eq) was added to intermediate 71-g (80 mg, crude) in MeOH/H$_2$O (10 mL/5 mL). The resulting suspension was stirred at 60° C. for 1 h. The reaction mixture was acidified with 1M HCl. The reaction mixture was diluted with ethyl acetate (50 mL). The organic phase was dried over Na$_2$SO$_4$, filtered and evaporated to give the crude product. The crude product was purified by flash C18 column to give intermediate 71-h in the form of a colorless oil (44 mg, 57.3%). M/z (ES+), [M+H]$^+$=334; HPLC $t_R$=0.634 min.

Preparation of Compound 71:

A solution of 3-(aminomethyl)-4,6-dimethylpyridin-2 (1H)-one (49.68 mg, 0.264 mmol, 2 eq), PyBop (82.51 mg, 0.158 mmol, 1.2 eq), DIEA (51.23 mg, 0.396 mmol, 3 eq) and intermediate 77-h (44 mg, 0.132 mmol, 1 eq) in DMSO (2 mL) was stirred at 30° C. for 1 h. The crude product was purified by Prep-HPLC (XBridge Prep C18 OBD column, 5μ silica, 19 mm in diameter, 150 mm in length) using a mixture of water (containing 0.01% FA) and acetonitrile with decreasing polarity as eluent. The fractions containing the desired compound were evaporated to dryness to give N-((4,6-dimethyl-2-oxo-1,2-dihydropyridin-3-yl)methyl)-3-(ethyl (tetrahydro-2H-pyran-4-yl)amino)-5-(2-(hydroxymethyl)cyclopropyl)-2-methylbenzamide (9.9 mg, 16.2%). m/z (ES+), [M+H]$^+$=468; HPLC $t_R$=0.739 min. 1H NMR (300 MHz, methanol-d$_4$) δ 7.02 (s, 1H), 6.79 (d, J=1.8 Hz, 1H), 6.13 (s, 1H), 4.47 (s, 2H), 3.93 (d, J=11.8 Hz, 2H), 3.62-3.44 (m, 2H), 3.40 (s, 2H), 3.09 (q, J=7.1 Hz, 3H), 2.40 (s, 3H), 2.25 (d, J=5.4 Hz, 6H), 1.71 (t, J=29.3 Hz, 5H), 1.34 (d, J=5.8 Hz, 1H), 0.87 (dt, J=14.0, 6.9 Hz, 5H). Based on SFC (CHIRALPAK AS-3 3.0×100 mm 3 um; column: 4-A-10%-50%-6.5 min-2 mL. 1 cm; MeOH: 20 mM NH$_3$), the ratio of the two isomers was (46.2:51.0).

Example 72: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(2-(morpholinylmethyl)cyclopropyl)benzamide (72)

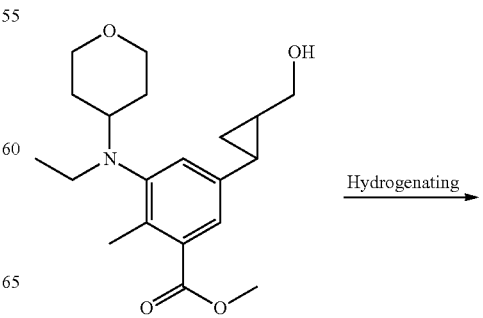

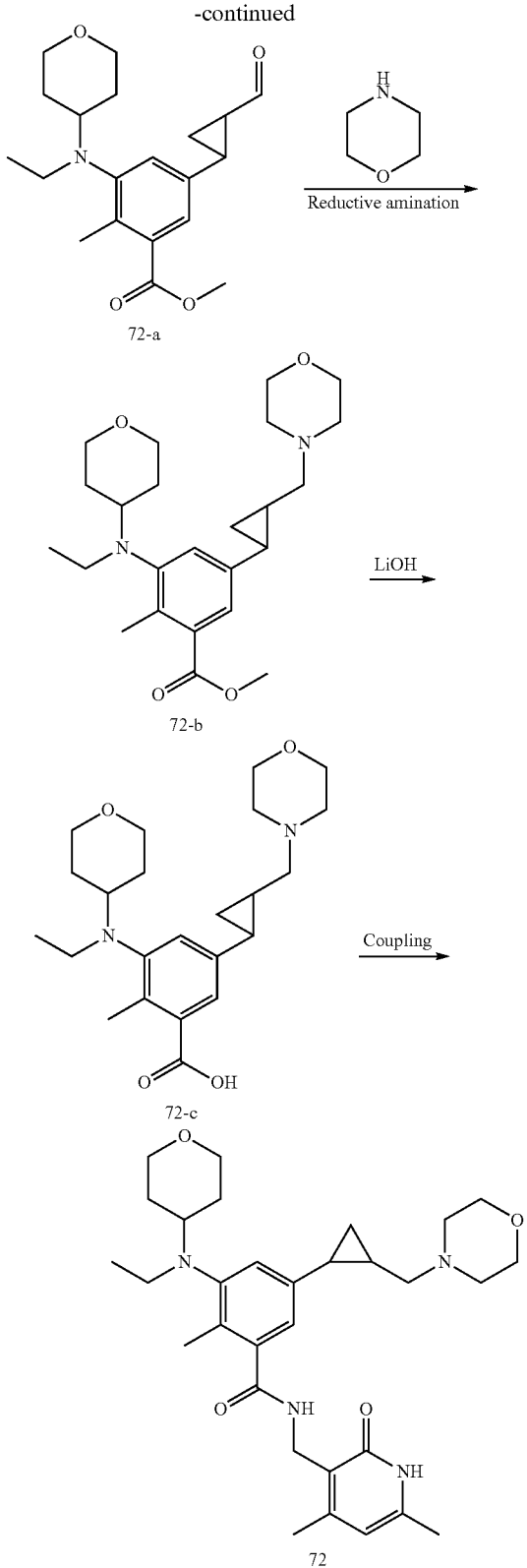

Preparation of Intermediate 72-a:

Dess-Martin periodide (3.18 g, 7.49 mmol, 2 eq) was added to a solution of compound methyl 3-(ethyl(tetrahydro-2H-pyran-4-yl)amino)-5-(2-(hydroxymethyl)cyclopropyl)-2-methylbenzoate (1.3 g, crude) in dichloromethane (60 mL). The resulting suspension was stirred at 0° C. for 1 h. After the reaction was completed, the mixture was filtered through silica gel and washed with DCM. The filtrate was dried over $Na_2SO_4$ and concentrated to give the desired intermediate 72-a (1.2 g). The crude product was used in the next step directly without further purification. m/z (ES+), $[M+H]^+=346$; HPLC $t_R=0.716$ min.

Preparation of Intermediate 72-b:

Morpholine (453 mg, 5.20 mmol, 1.5 eq) was added to a solution of intermediate 78-a (1.2 g, crude) in methanol (32 mL) with stirring. After stirring for 0.5 h, $NaBH(OAc)_3$ (1.84 g, 8.67 mmol, 2.5 eq) was added. The reaction mixture was stirred at room temperature for 2 h. After the reaction was completed, the solvent was removed under reduced pressure. The mixture was basified with aq. $NaHCO_3$ to pH=8 and extracted with ethyl acetate. The combined organic phases were washed with water, dried over $Na_2SO_4$ and concentrated to give the crude product. The crude product was purified by Prep-HPLC (XBridge Prep C18 OBD column, 5μ silica, 19 mm in diameter, 150 mm in length) using a mixture of water (containing 0.05% TFA) and MeCN with decreasing polarity as eluent. The fractions containing the desired compound were evaporated to dryness to give intermediate 72-b in the form of an oil (290 mg, 20% in three steps). m/z (ES+), $[M+H]^+=417$; HPLC $t_R=0.503$ min.

Preparation of Intermediate 72-c:

LiOH (167 mg, 6.97 mmol, 10 eq) was added to a solution of intermediate 72-b (290 mg, crude) in $MeOH/H_2O$ (10 mL/5 mL). The resulting suspension was stirred at 60° C. for 1 h. The reaction mixture was then acidified with 1M HCl. The reaction mixture was diluted with ethyl acetate (50 mL). The organic phase was dried over $Na_2SO_4$, filtered and evaporated to give the crude product. The crude product was purified by flash column C18 to give intermediate 72-c in the form of a colorless oil (84 mg, 30%). M/z (ES+), $[M+H]^+=403$; HPLC $t_R=0.488$ min.

Preparation of Compound 72:

A solution of 3-(aminomethyl)-4,6-dimethylpyridin-2(1H)-one (78.57 mg, 0.42 mmol, 2 eq), PyBop (130.49 mg, 0.25 mmol, 1.2 eq), DIEA (81.02 mg, 0.63 mmol, 3 eq) and intermediate 72-c (84 mg, 0.21 mmol, 1 eq) in DMSO (2 mL) was stirred at 30° C. for 1 h. The crude product was purified by Prep-HPLC (column: Xselect CSH OBD column 30×150 mm 5 um n; mobile phase A: water (0.05% TFA), mobile phase B: ACN; flow rate: 60 mL/min; gradient: 8% B to 18% B over 7 min; 254; 220 nm; Rt: 6.53 min). The fractions containing the desired compound were evaporated to dryness to give N-((4,6-dimethyl-2-oxo-1,2-dihydropyridin-3-yl)methyl)-3-(ethyl(tetrahydro-2H-pyran-4-yl)amino)-2-methyl-5-(2-(morpholinylmethyl)cyclopropyl) benzamide (62.3 mg, 44%). M/z (ES+), $[M+H]^+=537$; HPLC $t_R=0.652$ min. 1H NMR (300 MHz, methanol-$d_4$) δ 7.40 (s, 1H), 7.15 (s, 1H), 6.16-6.09 (m, 1H), 4.46 (s, 2H), 4.12-3.93 (m, 4H), 3.78 (t, J=12.6 Hz, 3H), 3.65-3.49 (m, 4H), 3.42-3.32 (m, 3H), 3.20 (dd, J=13.3, 7.5 Hz, 3H), 2.36 (d, J=11.2 Hz, 6H), 2.24 (d, J=0.9 Hz, 3H), 2.12 (dt, J=9.6, 5.0 Hz, 1H), 1.85 (d, J=51.8 Hz, 4H), 1.55 (s, 1H), 1.31 (dd, J=9.4, 4.8 Hz, 1H), 1.19 (dt, J=10.7, 5.4 Hz, 1H), 0.96 (t, J=7.0 Hz, 3H).

Example 73: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(2-(piperazin-1-ylmethyl)cyclopropyl)benzamide (73)

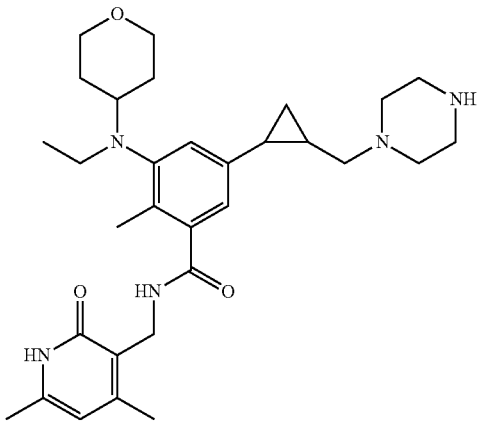 [SMILES: CCN(c1cc(C2CC2CN2CCNCC2)cc(C(=O)NCc2c(C)cc(C)[nH]c2=O)c1C)C1CCOCC1]

The title compound was prepared by referring to Example 71 and Example 72.

m/z (ES+), [M+H]$^+$=536; HPLC $t_R$=1.141 min. 1H NMR (300 MHz, methanol-$d_4$) δ 7.00 (d, J=1.8 Hz, 1H), 6.77 (d, J=1.7 Hz, 1H), 6.13 (s, 1H), 4.47 (s, 2H), 3.93 (d, J=11.3 Hz, 2H), 3.38 (d, J=10.3 Hz, 2H), 3.16-2.95 (m, 3H), 2.89 (t, J=5.0 Hz, 4H), 2.64 (d, J=5.7 Hz, 1H), 2.59 (d, J=6.0 Hz, 3H), 2.40 (s, 3H), 2.34-2.21 (m, 7H), 1.80-1.66 (m, 3H), 1.66-1.55 (m, 2H), 1.15 (s, 1H), 1.07-0.94 (m, 1H), 0.86 (q, J=7.1 Hz, 4H).

Example 74: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(2-((4-methylpiperazin-1-yl)methyl)cyclopropyl)benzamide (74)

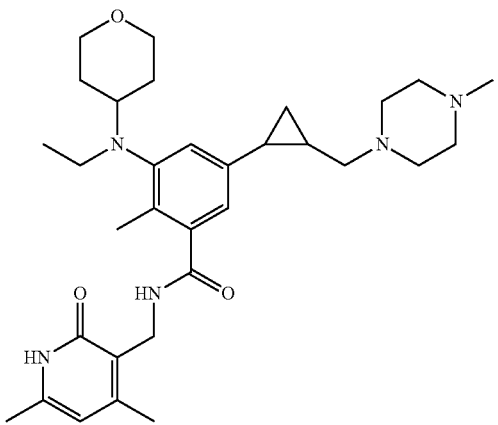

The title compound was prepared by referring to Example 71 and Example 72.

m/z (ES+), [M+H]$^+$=550; HPLC $t_R$=0.981 min. 1H NMR (300 MHz, methanol-$d_4$) δ 6.99 (s, 1H), 6.77 (s, 1H), 6.13 (s, 1H), 4.47 (s, 2H), 3.93 (d, J=11.2 Hz, 2H), 3.40 (s, 3H), 3.09 (q, J=7.3 Hz, 3H), 2.81-2.45 (m, 7H), 2.39 (s, 4H), 2.30 (s, 4H), 2.25 (d, J=5.4 Hz, 6H), 1.77-1.55 (m, 5H), 1.14 (s, 1H), 1.07-0.95 (m, 1H), 0.85 (t, J=6.9 Hz, 4H).

Example 75: Preparation of the Compound N-((4,6-dimethyl-2-oxo-1,2-dihydropyridin-3-yl)methyl)-5-(2-((cis-2,6-dimethylmorpholinyl)methyl)cyclopropyl)-3-(ethyl(tetrahydro-2H-pyran-4-yl)amino)-2-methylbenzamide (75)

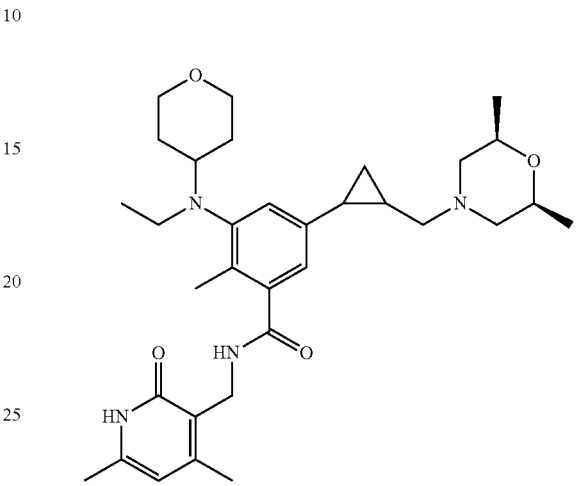

The title compound was prepared by referring to Example 71 and Example 72.

m/z (ES+), [M+H]$^+$=565.6; HPLC $t_R$=1.742 min. 1H NMR (400 MHz, methanol-$d_4$) δ 7.50-7.41 (s, 1H), 7.21-7.10 (s, 1H), 6.19-6.12 (s, 1H), 4.50-4.45 (s, 2H), 4.07-3.96 (d, J=11.5 Hz, 2H), 3.96-3.86 (d, J=10.3 Hz, 2H), 3.79-3.60 (s, 2H), 3.59-3.49 (m, 2H), 3.45-3.33 (d, J=11.6 Hz, 5H), 3.22-3.13 (dd, J=13.2, 7.7 Hz, 1H), 2.81-2.68 (td, J=11.6, 5.8 Hz, 2H), 2.43-2.38 (s, 3H), 2.38-2.34 (s, 3H), 2.29-2.25 (m, 3H), 2.17-2.10 (m, 1H), 1.94-1.69 (s, 3H), 1.65-1.55 (s, 1H), 1.37-1.29 (q, J=6.5, 5.5 Hz, 1H), 1.29-1.18 (m, 6H), 1.05-0.94 (t, J=6.9 Hz, 3H).

Example 76: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(2-((4-neopentylpiperazin-1-yl)methyl)cyclopropyl)benzamide (76)

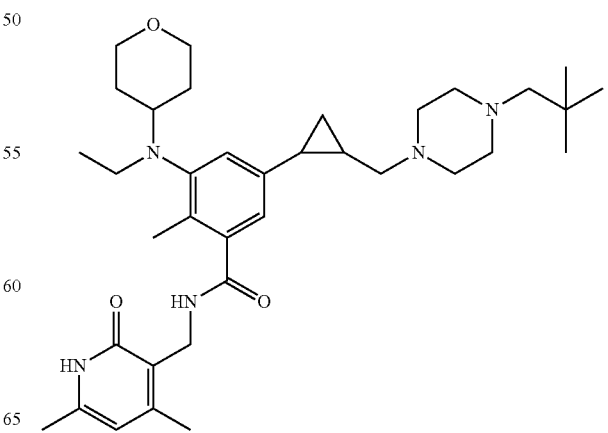

The title compound was prepared by referring to Example 71 and Example 72.

m/z (ES+), [M+H]$^+$=606; HPLC $t_R$=0.750 min. 1H NMR (300 MHz, methanol-d$_4$) δ 7.35 (s, 1H), 7.10 (s, 1H), 6.12 (s, 1H), 4.46 (s, 2H), 3.97 (d, J=11.5 Hz, 2H), 3.36 (s, 4H), 3.30-3.20 (m, 3H), 3.13 (dd, J=13.3, 7.5 Hz, 1H), 2.98 (s, 4H), 2.53-2.29 (m, 8H), 2.24 (d, J=0.8 Hz, 3H), 2.08 (dt, J=9.5, 5.0 Hz, 1H), 1.84 (d, J=57.9 Hz, 4H), 1.51 (s, 1H), 1.27 (q, J=5.5 Hz, 1H), 1.16 (dt, J=9.1, 5.4 Hz, 1H), 0.95 (s, 10H), 0.92 (s, 2H).

Example 77: Preparation of the Compound N-((4,6-dimethyl-2-oxo-1,2-dihydropyridin-3-yl)methyl)-3-(ethyl(tetrahydro-2H-pyran-4-yl)amino)-2-methyl-5-(2-(piperidin-1-ylmethyl)cyclopropyl)benzamide (77)

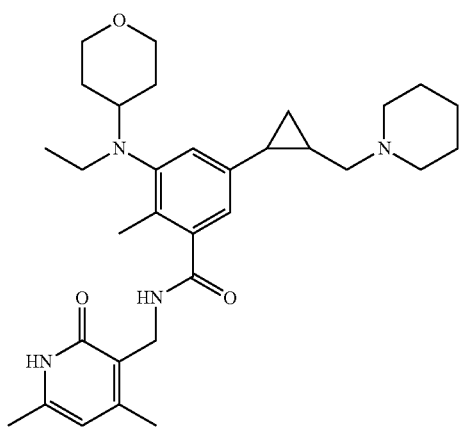 [SMILES: CCN(c1cc(C2CC2CN2CCCCC2)cc(C(=O)NCc2c(C)cc(C)[nH]c2=O)c1C)C1CCOCC1]

The title compound was prepared by referring to Example 71 and Example 72.

m/z (ES+), [M+H]$^+$=535; HPLC $t_R$=0.712 min. 1H NMR (300 MHz, methanol-d$_4$) δ 7.43 (s, 1H), 7.15 (s, 1H), 6.15 (s, 1H), 4.49 (s, 2H), 4.00 (d, J=11.2 Hz, 2H), 3.62 (d, J=12.1 Hz, 4H), 3.40 (d, J=12.1 Hz, 2H), 3.27 (d, J=6.7 Hz, 1H), 3.21-3.10 (m, 1H), 2.99 (s, 2H), 2.38 (d, J=12.8 Hz, 6H), 2.27 (d, J=0.8 Hz, 3H), 2.12 (s, 1H), 2.03-1.68 (m, 9H), 1.55 (s, 2H), 1.32 (d, J=6.5 Hz, 1H), 1.20 (d, J=8.8 Hz, 1H), 0.98 (t, J=7.0 Hz, 3H).

Example 78: Preparation of the Compound 5-(2-((4,4-difluoropiperidin-1-yl)methyl) cyclopropyl)-N-((4,6-dimethyl-2-oxo-1,2-dihydropyridin-3-yl) methyl)-3-(ethyl(tetrahydro-2H-pyran-4-yl)amino)-2-methylbenzamide (78)

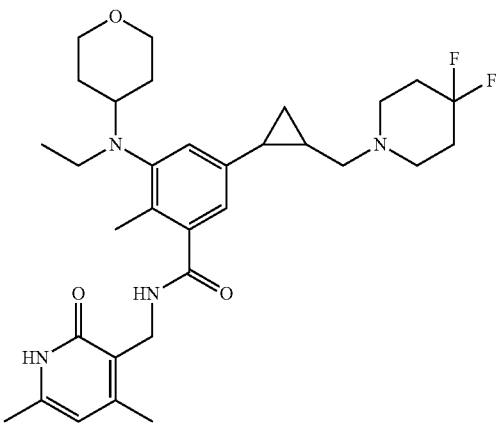 [SMILES: CCN(c1cc(C2CC2CN2CCC(F)(F)CC2)cc(C(=O)NCc2c(C)cc(C)[nH]c2=O)c1C)C1CCOCC1]

The title compound was prepared by referring to Example 71 and Example 72.

m/z (ES+), [M+H]$^+$=571; HPLC $t_R$=0.721 min. 1H NMR (300 MHz, methanol-d$_4$) δ 7.34 (s, 1H), 7.09 (s, 1H), 6.15 (s, 1H), 4.49 (s, 2H), 3.99 (d, J=11.7 Hz, 2H), 3.64-3.35 (m, 9H), 3.32-3.20 (m, 1H), 2.52-2.22 (m, 15H), 2.16 (s, 1H), 1.75 (s, 3H), 1.56 (s, 1H), 1.32 (s, 1H), 1.21 (s, 1H), 0.96 (t, J=6.9 Hz, 3H).

Example 79: Preparation of the Compound N-((4,6-dimethyl-2-oxo-1,2-dihydropyridin-3-yl)methyl)-3-(ethyl(tetrahydro-2H-pyran-4-yl)amino)-5-(2-((4-fluoropiperidin-1-yl)methyl)cyclopropyl)-2-methylbenzamide (79)

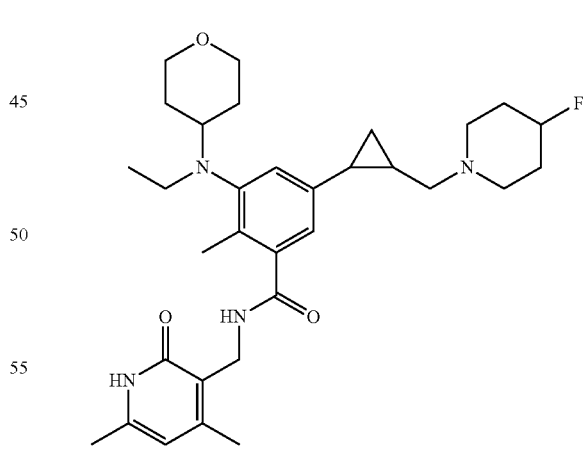

The title compound was prepared by referring to Example 71 and Example 72.

m/z (ES+), [M+H]$^+$=553; HPLC $t_R$=1.029 min. 1H NMR (300 MHz, methanol-d$_4$) δ 7.43 (s, 1H), 7.20 (s, 1H), 6.14 (s, 1H), 4.49 (s, 2H), 4.00 (s, 2H), 4.2-3.8 (m, 2H), 3.8-3.49 (m, 5H), 3.45-3.37 (m, 3H), 3.3-3.1 (m, 3H), 2.5-2.37 (m, 6H), 2.35-1.89 (m, 9H), 1.89-1.45 (m, 4H), 1.4-1.25 (m, 1H), 1.23-1.1 (m, 1H), 1.1-0.8 (m, 2H).

Example 80: Preparation of the Compound methyl 4-((2-(3-(((4,6-dimethyl-2-oxo-1,2-dihydropyridin-3-yl)methyl) carbamoyl)-5-(ethyl(tetrahydro-2H-pyran-4-yl)amino)-4-methylphenyl)cyclopropyl) methyl)piperazine-1-carboxylate (80)

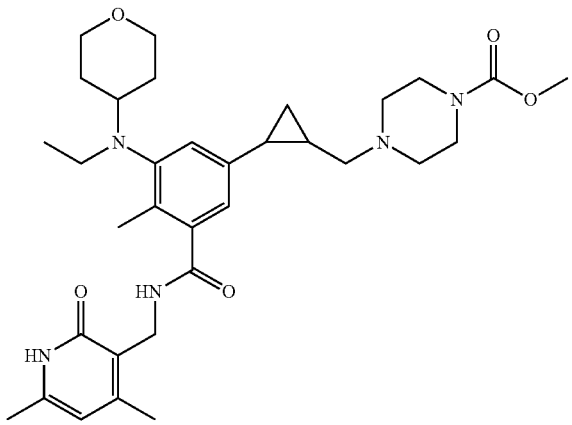

The title compound was prepared by referring to Example 71 and Example 72.

m/z (ES+), [M+H]$^+$=594; HPLC $t_R$=1.354 min. 1H NMR (400 MHz, methanol-d$_4$) δ 7.48-7.34 (s, 1H), 7.21-7.10 (s, 1H), 6.18-6.13 (s, 1H), 4.54-4.45 (s, 2H), 4.34-4.19 (s, 1H), 4.06-3.95 (d, J=11.1 Hz, 2H), 3.79-3.75 (s, 3H), 3.73-3.49 (s, 4H), 3.49-3.34 (s, 5H), 3.29-3.05 (dd, J=13.3, 7.6 Hz, 3H), 2.43-2.39 (s, 3H), 2.38-2.32 (d, J=3.9 Hz, 2H), 2.29-2.23 (s, 3H), 2.18-2.09 (s, 1H), 1.92-1.69 (s, 2H), 1.63-1.51 (s, 1H), 1.37-1.29 (s, 1H), 1.25-1.18 (s, 1H), 1.04-0.91 (s, 3H).

Example 81: Preparation of the Compound N-((4,6-dimethyl-2-oxo-1,2-dihydropyridin-3-yl)methyl)-3-(ethyl(trans-4-((2-methoxyethyl)(methyl)amino) cyclohexyl)amino)-2-methyl-5-(2-((4-methylpiperazin-1-yl)methyl)cyclopropyl)benzamide (81)

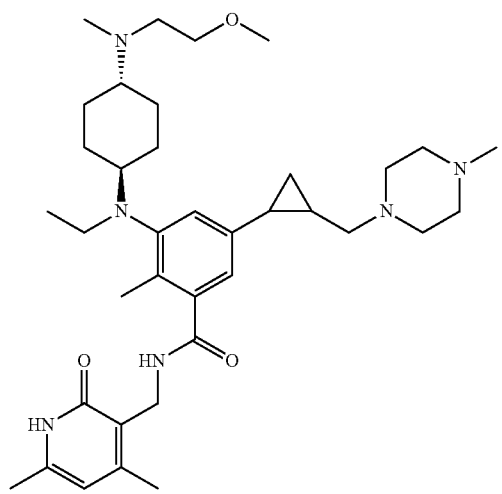

The title compound was prepared by referring to Example 71 and Example 72.

m/z (ES+), [M+H]$^+$=635.5; HPLC $t_R$=0.708 min. 1H NMR (400 MHz, methanol-d$_4$) δ 7.13-7.01 (s, 1H), 6.95-6.86 (s, 1H), 6.20-6.14 (s, 1H), 4.51-4.44 (s, 2H), 3.75-3.71 (t, J=5.0 Hz, 2H), 3.66-3.55 (d, J=26.7 Hz, 8H), 3.52-3.40 (s, 5H), 3.30-3.16 (m, 3H), 3.01-2.93 (s, 3H), 2.89-2.84 (s, 3H), 2.44-2.39 (s, 3H), 2.38-2.32 (s, 3H), 2.29-2.24 (s, 3H), 2.11-1.99 (m, 2H), 1.97-1.49 (d, J=142.3 Hz, 6H), 1.48-1.31 (d, J=45.1 Hz, 2H), 1.26-1.17 (d, J=6.3 Hz, 1H), 1.15-1.08 (dt, J=10.1, 5.4 Hz, 1H), 0.95-0.85 (t, J=6.9 Hz, 3H).

Example 82: Preparation of the Compound N-((4,6-dimethyl-2-oxo-1,2-dihydropyridin-3-yl)methyl)-3-(ethyl(trans-4-((2-methoxyethyl)(methyl)amino) cyclohexyl)amino)-2-methyl-5-(2-(morpholinylmethyl)cyclopropyl)benzamide (82)

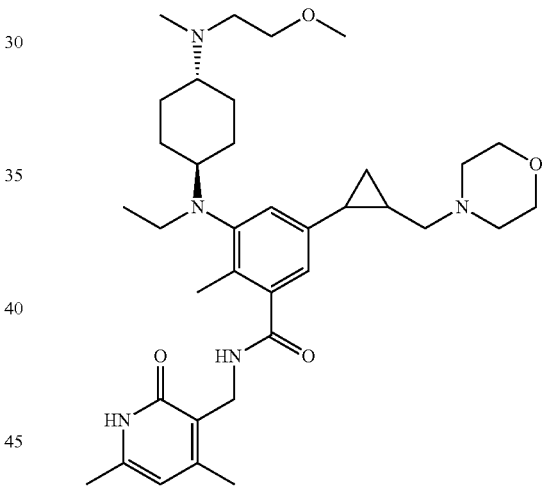

The title compound was prepared by referring to Example 71 and Example 72.

m/z (ES+), [M+H]$^+$=622; HPLC $t_R$=1.308 min. 1H NMR (300 MHz, methanol-d$_4$) δ 6.97 (d, J=1.9 Hz, 1H), 6.76 (d, J=1.7 Hz, 1H), 6.13 (s, 1H), 4.47 (s, 2H), 3.69 (t, J=4.7 Hz, 4H), 3.51 (t, J=5.7 Hz, 3H), 3.35 (s, 3H), 3.02 (d, J=7.2 Hz, 2H), 2.74 (s, 2H), 2.65 (dd, J=12.7, 5.4 Hz, 1H), 2.57 (s, 5H), 2.42-2.19 (m, 13H), 1.96 (s, 2H), 1.74 (dt, J=9.2, 4.9 Hz, 1H), 1.65 (s, 2H), 1.45 (d, J=11.8 Hz, 4H), 1.14 (d, J=5.0 Hz, 1H), 1.06-0.94 (m, 1H), 0.87 (t, J=6.9 Hz, 4H).

Example 83: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(2-(piperazin-1-ylmethyl)cyclopropyl)benzamide (83)

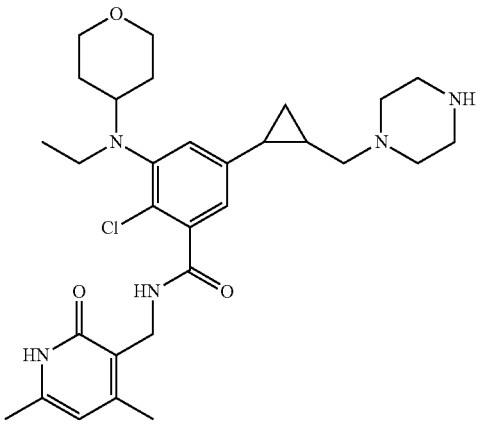 [SMILES: CCN(c1cc(C2CC2CN2CCNCC2)cc(C(=O)NCc2c(C)cc(C)[nH]c2=O)c1Cl)C1CCOCC1]

The title compound was prepared by referring to Example 71 and Example 72.

m/z (ES+), [M+H]$^+$=556; HPLC $t_R$=1.176 min. $^1$H NMR (300 MHz, methanol-$d_4$) δ 8.38 (s, 2H), 7.05 (dd, J=9.4, 2.1 Hz, 1H), 6.84 (d, J=2.1 Hz, 1H), 6.14 (s, 1H), 4.48 (s, 2H), 3.95 (d, J=11.2 Hz, 2H), 3.43-3.33 (m, 2H), 3.19 (dt, J=22.2, 6.1 Hz, 7H), 2.81 (d, J=5.7 Hz, 3H), 2.67 (dt, J=12.7, 6.6 Hz, 1H), 2.48 (dd, J=12.9, 7.0 Hz, 1H), 2.40 (s, 3H), 2.27 (s, 3H), 1.86-1.76 (m, 1H), 1.74 (d, J=4.1 Hz, 2H), 1.75-1.64 (m, 2H), 1.23 (s, 1H), 1.12-1.00 (m, 1H), 1.00-0.84 (m, 3H).

Example 84: Preparation of the Compound 2-chloro-N-((4,6-dimethyl-2-oxo-1,2-dihydropyridin-3-yl)methyl)-3-(ethyl(tetrahydro-2H-pyran-4-yl)amino)-5-(2-(morpholinylmethyl)cyclopropyl)benzamide (84)

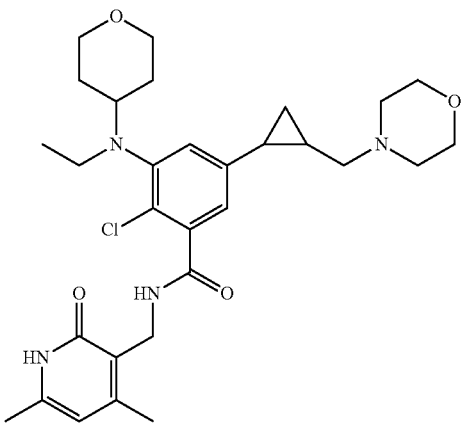 [SMILES: CCN(c1cc(C2CC2CN2CCOCC2)cc(C(=O)NCc2c(C)cc(C)[nH]c2=O)c1Cl)C1CCOCC1]

The title compound was prepared by referring to Example 71 and Example 72.

m/z (ES+), [M+H]$^+$=557; HPLC $t_R$=0.949 min. $^1$H NMR (300 MHz, methanol-$d_4$) δ 7.08 (d, J=2.2 Hz, 1H), 6.85 (d, J=2.1 Hz, 1H), 6.13 (s, 1H), 4.48 (s, 2H), 3.95 (d, J=11.6 Hz, 2H), 3.80 (t, J=4.7 Hz, 4H), 3.35-3.40 (d, J=3.2 Hz, 2H), 3.29-3.11 (m, 2H), 2.91 (s, 5H), 2.85 (d, J=6.4 Hz, 1H), 2.74 (d, J=13.5 Hz, 1H), 2.40 (s, 3H), 2.26 (d, J=0.8 Hz, 3H), 1.90 (dt, J=9.1, 4.9 Hz, 1H), 1.78-1.64 (m, 4H), 1.31 (s, 1H), 1.19-1.08 (m, 1H), 1.02 (dt, J=10.6, 5.3 Hz, 1H), 0.89 (t, J=7.0 Hz, 3H).

Example 85: Preparation of the Compound 2-chloro-N-((4,6-dimethyl-2-oxo-1,2-dihydropyridin-3-yl)methyl)-5-(2-(((2S,6R)-2,6-dimethylmorpholinyl)methyl)cyclopropyl)-3-(ethyl(tetrahydro-2H-pyran-4-yl)amino)benzamide (85)

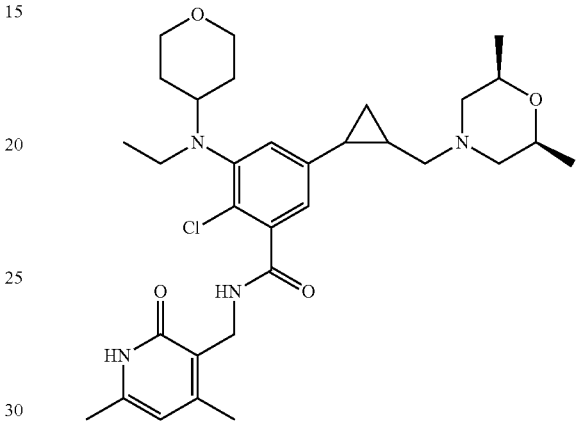

The title compound was prepared by referring to Example 71 and Example 72.

m/z (ES+), [M+H]$^+$=585; HPLC $t_R$=0.803 min. $^1$H NMR (300 MHz, methanol-$d_4$) δ 7.07 (d, J=2.2 Hz, 1H), 6.80 (d, J=2.1 Hz, 1H), 6.13 (s, 1H), 4.49 (s, 2H), 3.95 (d, J=11.5 Hz, 2H), 3.44-3.33 (m, 1H), 3.32-3.10 (m, 3H), 2.89 (d, J=11.4 Hz, 2H), 2.63 (dd, J=12.8, 5.4 Hz, 1H), 2.39 (s, 3H), 2.34-2.21 (m, 4H), 1.77 (dt, J=18.1, 10.4 Hz, 7H), 1.01 (dt, J=69.5, 6.8 Hz, 13H).

Example 86: Preparation of the Compound 3-((8-oxabicyclo[3.2.1]octan-3-yl)(ethyl)amino)-N-((4,6-dimethyl-2-oxo-1,2-dihydropyridin-3-yl)methyl-2-methyl-5-(trans-3-morpholinocyclobutoxy)benzamide (86)

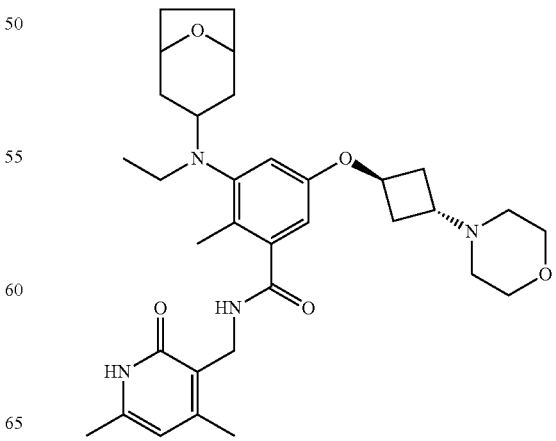

The title compound was prepared by referring to Example 4 with tetrahydropyran-4-one replaced by 8-oxabicyclo[3.2.1]octan-3-one and to the following procedure. To a solution of 3-aminomethyl-4-methyl-6-methylpyridin-2(1H)-one hydrochloride (188 mg, 1 mmol, 1.05 eq), EDC·HCl (225 mg, 1.2 mmol, 1.25 eq), HOBt·H$_2$O (179 mg, 1.2 mmol, 1.25 eq), and 3-((8-oxabicyclo[3.2.1]octan-3-yl)(ethyl)amino)-5-(trans-3-morpholinocyclobutoxy)-2-methylbenzoic acid (400 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 3-((8-oxabicyclo[3.2.1]octan-3-yl)(ethyl)amino)-N-((4,6-dimethyl-2-oxo-1,2-dihydropyridin-3-yl)methyl-2-methyl-5-(trans-3-morpholinocyclobutoxy)benzamide (86).

m/z (ES+), [M+H]$^+$=579.25; $^1$H NMR (400 MHz, CD$_3$OD) δ 7.10 (s, 1H), 6.93 (s, 1H), 6.19 (s, 1H), 5.95 (s, 1H), 4.49-4.41 (m, 4H), 4.10 (m, 3H), 3.96-3.82 (m, 3H), 3.73-3.56 (m, 4H), 3.05 (m, 2H), 2.88 (m, 3H), 2.56 (m, 2H), 2.40 (s, 3H), 2.28-2.18 (m, 7H), 2.06 (s, 2H), 1.80 (m, 2H), 1.58 (m, 2H), 0.95 (t, J=10.7 Hz, 3H).

Example 87: Preparation of the Compound 3-((4,4-difluorocyclohexyl)(ethyl)amino)-5-(trans-3-(cis-2,6-dimethylmorpholino)cyclobutoxy)-N-((4-methoxy-6-methyl-2-oxo-1,2-dihydropyridin-3-yl)methyl)-2-methylbenzamide (87)

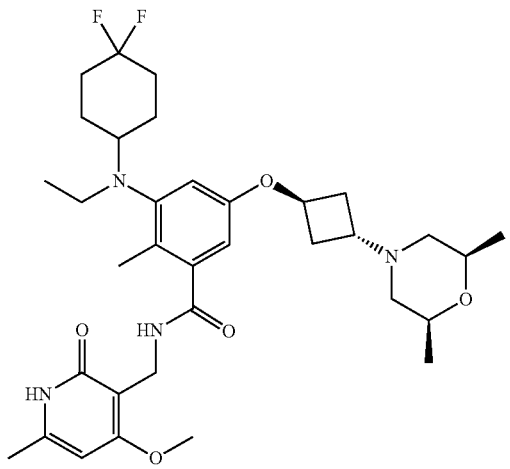

The title compound was prepared by referring to Example 45 and the following procedure. To a solution of 3-aminomethyl-4-methoxy-6-methylpyridin-2 (1H)-one (168 mg, 1 mmol, 1.05 eq), EDC·HCl (225 mg, 1.2 mmol, 1.25 eq), HOBt·H$_2$O (179 mg, 1.2 mmol, 1.25 eq), and 3-((4,4-difluorocyclohexyl)(ethyl)amino)-5-(trans-3-(cis-2,6-dimethylmorpholino)cyclobutoxy)-2-methylbenzoic acid (450 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 3-((4,4-difluorocyclohexyl)(ethyl)amino-5-(trans-3-(cis-2,6-dimethylmorpholino)cyclobu-toxy)-N-((4-methoxy-6-methyl-2-oxo-1,2-dihydropyridin-3-yl)methyl)-2-methylbenzamide (87).

m/z (ES+), [M+H]$^+$=631.34; HPLC tR=7.226 min. $^1$H NMR (400 MHz, DMSO-d$_6$) δ 11.41 (s, 1H), 7.84 (t, J=4.7 Hz, 1H), 6.61 (d, J=2.3 Hz, 1H), 6.40 (d, J=2.5 Hz, 1H), 6.10 (s, 1H), 4.78-4.66 (m, 1H), 4.21 (d, J=4.5 Hz, 2H), 3.81 (s, 3H), 3.58-3.51 (m, 2H), 3.02-2.95 (m, 3H), 2.88-2.81 (m, 1H), 2.78 (d, 2H), 2.38-2.32 (m, 2H), 2.18 (s, 3H), 2.12-2.07 (m, 5H), 2.01-1.93 (m, 2H), 1.85-1.72 (m, 4H), 1.64-1.55 (m, 2H), 1.40 (t, J=10.7 Hz, 2H), 1.06 (d, J=6.2 Hz, 6H), 0.80 (t, J=7.0 Hz, 3H).

Example 88: Preparation of the Compound 3-((8-oxabicyclo[3.2.1]octan-3-yl)(ethyl) amino)-5-(trans-3-(cis-2,6-dimethylmorpholinyl)cyclobutoxy)-N-((4-methoxy-6-methyl-2-oxo-1,2-dihydropyridin-3-yl)methyl)-2-methylbenzamide (88)

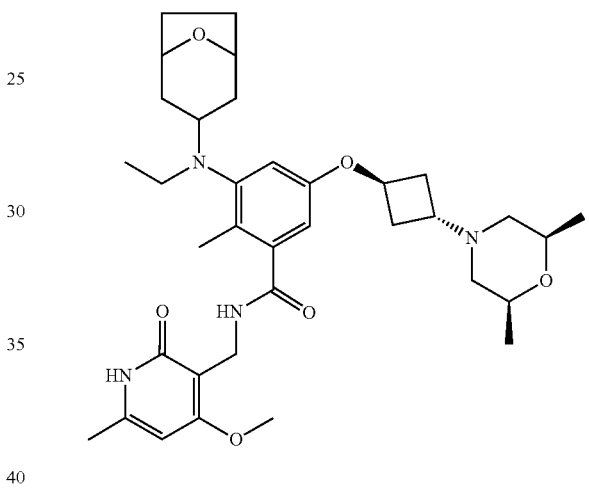

The title compound was prepared by referring to Example 47 and the following procedure. To a solution of 3-aminomethyl-4-methoxy-6-methylpyridin-2 (1H)-one (168 mg, 1 mmol, 1.05 eq), EDC·HCl (225 mg, 1.2 mmol, 1.25 eq), HOBt·H$_2$O (179 mg, 1.2 mmol, 1.25 eq), and 3-((8-oxabicyclo[3.2.1]octan-3-yl)(ethyl)amino)-5-(trans-3-(cis-2,6-dimethylmorpholino)cyclobutoxy)-2-methylbenzoic acid (443 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 3-((8-oxabicyclo[3.2.1]octan-3-yl)(ethyl) amino)-5-(trans-3-(cis-2,6-dimethylmorpholinyl)cyclobutoxy)-N-((4-methoxy-6-methyl-2-oxo-1,2-dihydropyridin-3-yl)methyl)-2-methylbenzamide (88).

m/z (ES+), [M+H]$^+$=623.34; HPLC tR=7.186 min. $^1$H NMR (400 MHz, CD$_3$OD) δ 8.28 (s, 1H), 6.55 (d, J=2.3 Hz, 1H), 6.49 (d, J=2.4 Hz, 1H), 6.25 (s, 1H), 4.77 (m, 1H), 4.43 (s, 2H), 4.23 (s, 2H), 3.93 (s, 3H), 3.80-3.68 (m, 2H), 3.61 (s, 1H), 3.41-3.33 (m, 1H), 3.13 (d, J=6.7 Hz, 2H), 3.06 (d, J=11.4 Hz, 2H), 2.54 (dt, J=13.7, 6.7 Hz, 2H), 2.40-2.27 (m, 5H), 2.21 (s, 3H), 2.13-1.68 (m, 10H), 1.18 (d, J=6.3 Hz, 6H), 0.79 (t, J=7.0 Hz, 3H).

Example 89: Preparation of the Compound 2-chloro-3-(ethyl(tetrahydro-2H-pyran-4-yl)amino)-N-((4-methoxy-6-methyl-2-oxo-1,2-dihydropyridin-3-yl)methyl)-5-(trans-3-(4-methylpiperazin-1-yl)cyclobutoxy)benzamide (89)

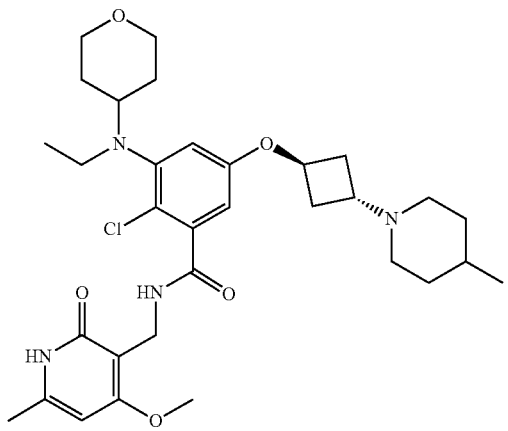

The title compound was prepared by referring to Example 1, Example 4 and the following procedure. To a solution of 3-aminomethyl-4-methoxy-6-methylpyridin-2 (1H)-one (168 mg, 1 mmol, 1.05 eq), EDC·HCl (225 mg, 1.2 mmol, 1.25 eq), HOBt·H₂O (179 mg, 1.2 mmol, 1.25 eq), and 2-chloro-3-(ethyl(tetrahydro-2H-pyran-4-yl)amino)-5-(trans-3-(4-methylpiperidin-1-yl)cyclobutoxy)benzoic acid (422 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 2-chloro-3-(ethyl(tetrahydro-2H-pyran-4-yl)amino)-N-((4-methoxy-6-methyl-2-oxo-1,2-dihydropyridin-3-yl)methyl)-5-(trans-3-(4-methylpiperazin-1-yl)cyclobutoxy)benzamide.

m/z (ES+), [M+H]⁺=601.19; HPLC tR=6.986 min. ¹H NMR (400 MHz, CD₃OD) δ6.72 (d, J=2.8 Hz, 1H), 6.56 (d, J=2.8 Hz, 1H), 4.76-4.71 (m, 1H), 4.40 (s, 2H), 3.97-3.90 (m, 5H), 3.38-3.21 (m, 4H), 3.15-3.10 (m, 2H), 3.05-2.99 (m, 1H), 2.92-2.89 (d, J=11.2 Hz, 2H), 2.42-2.35 (m, 2H), 2.31 (s, 3H), 2.28-2.22 (m, 2H), 1.85-1.79 (t, J=12.4 Hz, 2H), 1.75-1.68 (m, 6H), 1.41-1.18 (m, 3H), 0.96-0.95 (d, J=6.4 Hz, 3H), 0.91-0.88 (t, J=6.4 Hz, 3H)

Example 90: Preparation of the Compound 2-chloro-3-(ethyl(tetrahydro-2H-pyran-4-yl)amino)-N-((4-methyl-2-oxo-6-(trifluoromethyl)-1,2-dihydropyridin-3-yl)methyl)-5-(trans-3-(4-methylpiperazin-1-yl)cyclobutoxy)benzamide (90)

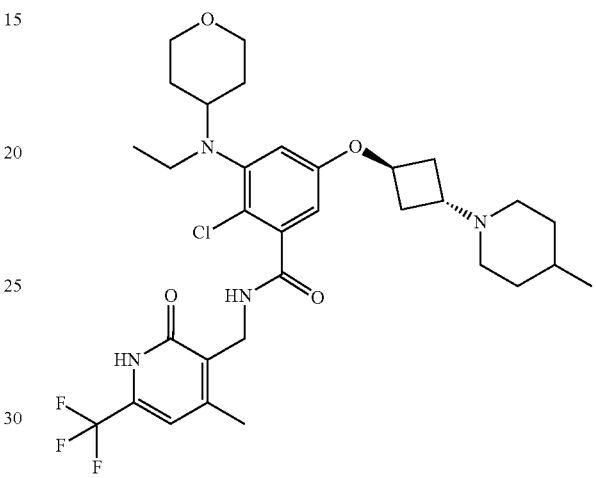

The title compound was prepared by referring to Example 1, Example 4 and the following procedure. To a solution of 3-aminomethyl-4-methyl-6-(trifluoromethyl)pyridin-2 (1H)-one (206 mg, 1 mmol, 1.05 eq), EDC·HCl (225 mg, 1.2 mmol, 1.25 eq), HOBt·H₂O (179 mg, 1.2 mmol, 1.25 eq), and 2-chloro-3-(ethyl(tetrahydro-2H-pyran-4-yl)amino)-5-(trans-3-(4-methylpiperidin-1-yl)cyclobutoxy)benzoic acid (422 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 2-chloro-3-(ethyl(tetrahydro-2H-pyran-4-yl)amino)-N-((4-methyl-2-oxo-6-(trifluoromethyl)-1,2-dihydropyridin-3-yl)methyl)-5-(trans-3-(4-methylpiperazin-1-yl)cyclobutoxy)benzamide.

m/z (ES+), [M+H]⁺=639.18; HPLC tR=5.950 min. ¹H NMR (400 MHz, CD₃OD) δ8.41 (m, 1H), 6.86 (s, 1H), 6.67 (d, J=2.8 Hz, 1H), 6.46 (d, J=2.4 Hz, 1H), 5.25 (m, 1H), 4.48 (s, 2H), 3.86-3.81 (m, 2H), 3.29-3.15 (m, 3H), 3.09-3.02 (m, 4H), 2.50-2.45 (m, 4H), 2.34-2.28 (m, 4H), 1.75-1.72 (m, 2H), 1.67-1.59 (m, 2H), 1.52-1.46 (m, 2H), 1.29-1.21 (m, 5H), 0.92 (d, J=8 Hz, 3H), 0.81 (t, J=7.2 Hz, 3H)

Example 91: Preparation of the Compound 3-((4,4-difluorocyclohexyl)(ethyl)amino)-N-((4-methoxy-6-methyl-2-oxo-1,2-dihydropyridin-3-yl)methyl)-2-methyl-5-(trans-3-(piperidin-1-yl)cyclobutoxy)benzamide (91)

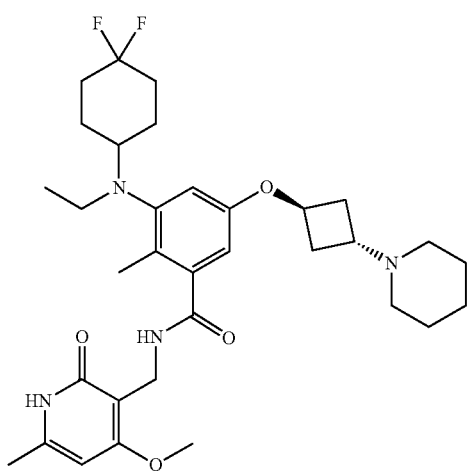 [SMILES: CCN(c1cc(O[C@H]2C[C@H](N3CCCCC3)C2)cc(C(=O)NCc2c(OC)cc(C)[nH]c2=O)c1C)C1CCC(F)(F)CC1]

The title compound was prepared by referring to Example 68 and the following procedure. To a solution of 3-aminomethyl-4-methoxy-6-methylpyridin-2 (1H)-one (168 mg, 1 mmol, 1.05 eq), EDC·HCl (225 mg, 1.2 mmol, 1.25 eq), HOBt·H₂O (179 mg, 1.2 mmol, 1.25 eq), and 3-((4,4-difluorocyclohexyl)(ethyl)amino)-2-methyl-5-(trans-3-(piperidin-1-yl)cyclobutoxy)benzoic acid (422 mg, 0.9 mmol, 1 eq) in DMF (5 mL) was added DIPEA (364 mg, 2.7 mmol, 3 eq) at room temperature. After the reaction was completed, the mixture was added with water (50 mL) and extracted with dichloromethane (100 mL×2). The organic phase was evaporated to dryness and the crude product was purified by a method similar to that of Example 1 and Example 2 to give 3-((4,4-difluorocyclohexyl)(ethyl)amino)-N-((4-methoxy-6-methyl-2-oxo-1,2-dihydropyridin-3-yl)methyl)-2-methyl-5-(trans-3-(piperidin-1-yl)cyclobutoxy)benzamide.

m/z (ES+), [M+H]⁺=601.42; HPLC tR=8.253 min. ¹H NMR (400 MHz, DMSO-d6) δ 11.43 (s, 1H), 7.83 (t, J=4.3 Hz, 1H), 6.59 (d, J=1.9 Hz, 1H), 6.38 (d, J=2.0 Hz, 1H), 6.09 (s, 1H), 4.72-4.57 (m, 1H), 4.19 (d, J=4.3 Hz, 2H), 3.80 (s, 3H), 3.05-2.88 (m, 3H), 2.87-2.74 (m, 1H), 2.35-2.23 (m, 3H), 2.18-2.22 (m, 3H), 2.17 (s, 3H), 2.11 (s, 3H), 2.04-2.10 (m, 2H), 1.95 (d, J=9.5 Hz, 2H), 1.82-1.67 (m, 4H), 1.55-1.64 (m, 2H), 1.44-1.52 (m, 4H), 1.38 (d, J=3.0 Hz, 2H), 0.79 (t, J=6.8 Hz, 3H).

Example 92: Preparation of the Compound N-((4,6-dimethyl-2-oxo-1,2-dihydropyridin-3-yl)methyl-3-(ethyl(tetrahydro-2H-pyran-4-yl)amino)-2-methyl-5-(trans-3-(piperidin-1-yl)cyclobutoxy)benzamide (92)

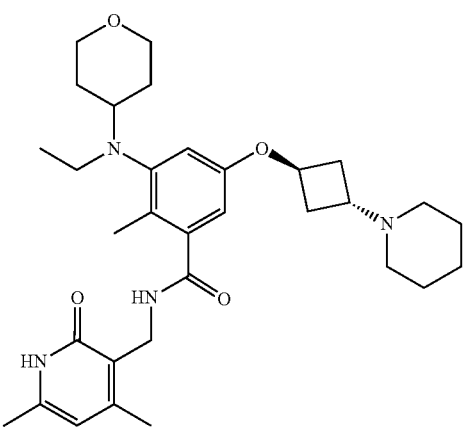 [SMILES: CCN(c1cc(O[C@H]2C[C@H](N3CCCCC3)C2)cc(C(=O)NCc2c(C)cc(C)[nH]c2=O)c1C)C1CCOCC1]

The title compound was prepared by referring to Example 1 with cyclobutanol replaced by 1,3-cis-3-(piperidin-1-yl)cyclobutyl-1-ol and to the following procedure.

To a solution of 3-aminomethyl-4-methyl-6-methylpyridin-2 (1H)-one hydrochloride (1 g, 5.3 mmol, 1.05 eq), EDC·HCl (1.2 g, 6.6 mmol, 1.25 eq), HOBt·H₂O (0.97 g, 6.6 mmol, 1.25 eq), and 3-(ethyl(tetrahydro-2H-pyran-4-yl)amino)-2-methyl-5-(trans-3 (piperidin-1-yl) cyclobutoxy) benzoic acid (2.1 g, 5.0 mmol, 1 eq) in DMF (10 mL) was added DIPEA (1.9 g, 15.1 mmol, 3 eq) at room temperature. After the reaction was completed, the mixture was added with water (80 mL) and filtered to give the filter cake, which was dried to give N-((4,6-dimethyl-2-oxo-1,2-dihydropyridin-3-yl)methyl)-3-(ethyl(tetrahydro-2H-pyran-4-yl)amino)-2-methyl-5-(trans-3 (piperidin-1-yl)cyclobutoxy)benzamide (1.7 g, white solid).

m/z (ES+), [M+H]⁺=551.40; HPLC tR=6.901 min. ¹H NMR (400 MHz, DMSO-d6) δ 11.45 (s, 1H), 8.02 (t, J=4.8 Hz, 1H), 6.59 (d, J=1.9 Hz, 1H), 6.38 (d, J=2.0 Hz, 1H), 5.85 (s, 1H), 4.70-4.63 (m, 1H), 4.25 (d, J=4.0 Hz, 2H), 3.83 (d, J=12 Hz, 2H), 3.24 (d, J=8 Hz, 2H), 3.00-2.85 (m, 3H), 2.32-2.23 (m, 10H), 2.10 (d, J=8 Hz, 8H), 1.6-1.59 (m, 2H), 1.50 (m, 6H), 1.38 (s, 2H), 0.78 (t, J=8.0 Hz, 3H)

Example 93: Preparation of the Compound 3-(ethyl (tetrahydro-2H-pyran-4-yl) amino)-N-((4-methoxy-6-methyl-2-oxo-1,2-dihydropyridin-3-yl)methyl)-2-methyl-5-(trans-3-(piperidin-1-yl)cyclobutoxy) benzamide (93)

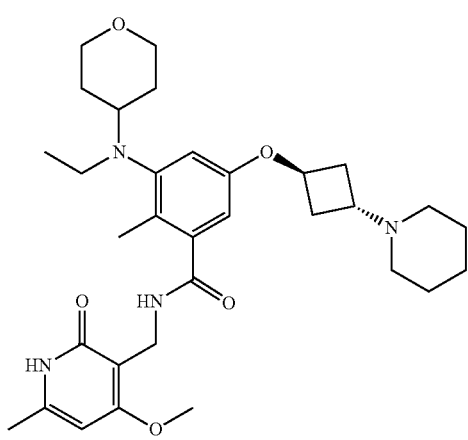 [SMILES: CCN(c1cc(O[C@H]2C[C@H](N3CCCCC3)C2)cc(C(=O)NCc2c(OC)cc(C)[nH]c2=O)c1C)C1CCOCC1]

The title compound was prepared by referring to Example 92 and the following procedure. At room temperature, to a solution of 3-aminomethyl-4-methoxy-6-methylpyridin-2 (1H)-one (0.9 g, 5.3 mmol, 1.05 eq), EDC·HCl (1.2 g, 6.6 mmol, 1.25 eq), HOBt·H$_2$ (0.97 g, 6.6 mmol, 1.25 eq), and 3-(ethyl(tetrahydro-2H-pyran-4-yl)amino)-2-methyl-5-(trans-3 (piperidin-1-yl) cyclobutoxy)benzoic acid (2.1 g, 5.0 mmol, 1 eq) in DMF (10 mL) was added DIPEA (1.9 g, 15.1 mmol, 3 eq). After the reaction was completed, the mixture was added with water (80 mL) and filtered to give the filter cake, which was dried to give 3-(ethyl(tetrahydro-2H-pyran-4-yl) amino)-N-((4-methoxy-6-methyl-2-oxo-1, 2-dihydropyridin-3-yl)methyl)-2-methyl-5-(trans-3-(piperidin-1-yl)cyclobutoxy)benzamide (2.3 g, white solid).

m/z (ES+), [M+H]$^+$=567.50; HPLC tR=6.400 min. $^1$H NMR (400 MHz, DMSO-d6) δ 11.46 (s, 1H), 7.86 (t, J=4.1 Hz, 1H), 6.62 (d, J=1.9 Hz, 1H), 6.42 (d, J=2.0 Hz, 1H), 6.12 (s, 1H), 4.71-4.68 (m, 1H), 4.24 (d, J=4.0 Hz, 2H), 3.96-3.83 (m, 5H), 3.25 (t, J=12.0 Hz, 2H), 3.04-2.85 (m, 3H), 2.34-2.21 (m, 9H), 2.14-2.10 (m, 6H), 1.65 (d, J=12.0 Hz, 2H), 1.52-1.50 (m, 6H), 1.42-1.41 (m, 2H), 0.78 (t, J=8.0 Hz, 3H)

Example 94: Preparation of the Compound 3-((4,4-difluorocyclohexyl)(ethyl)amino)-N-((4-hydroxy-6-methyl-2-oxo-1,2-dihydropyridin-3-yl)methyl)-2-methyl-5-(trans-3-(piperidin-1-yl)cyclobutoxy) benzamide (94)

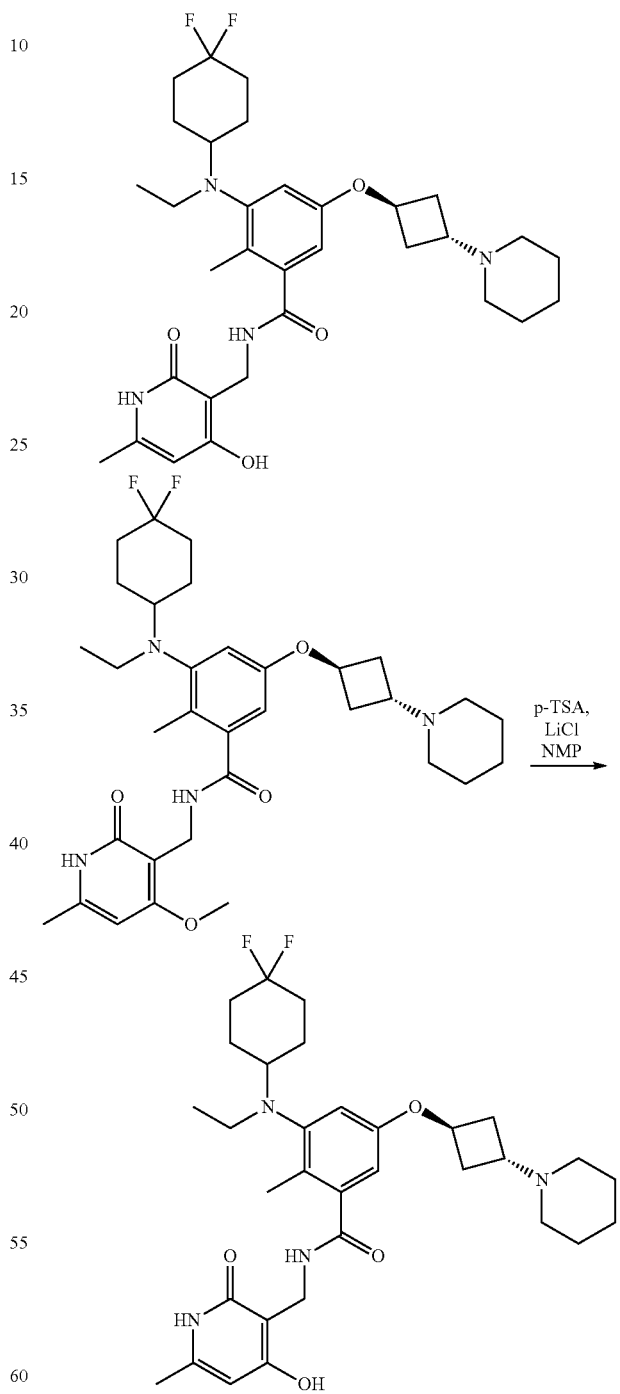

3-((4,4-difluorocyclohexyl)(ethyl)amino)-N-((4-methoxy-6-methyl-2-oxo-1,2-dihydropyridin-3-yl)methyl)-2-methyl-5-(trans-3-(piperidin-1-yl)cyclobutoxy)benzamide (200 mg, 0.33 mmol, 1 eq) was dissolved in N-methyl-2-pyrrolidone (10 mL), and lithium chloride (143 mg, 3.3 mmol, 10 eq) and p-toluenesulfonic acid (634 mg, 3.3 mmol, 10 eq) were added at room temperature. After stirring at 120° C. for 6 h, water (100 mL) was added to the system after the reaction was completed, and the mixture was extracted with dichloromethane (50 mL×3). The organic phase was concentrated under reduced pressure to give a crude product, which was purified by high-pressure reverse phase column chromatography and lyophilized to give 3-((4,4-difluorocyclohexyl)(ethyl)amino)-N-((4-hydroxy-6-methyl-2-oxo-1,2-dihydropyridin-3-yl)methyl)-2-methyl-5-(trans-3-(piperidin-1-yl)cyclobutoxy)benzamide (40 mg, 20%, white solid).

m/z (ES+), [M+H]$^+$=587.34; HPLC tR=3.789 min. $^1$H NMR (400 MHz, DMSO-d6) δ 11.11 (s, 1H), 10.85 (s, 1H), 8.68 (t, J=5.3 Hz, 1H), 6.66 (d, J=2.2 Hz, 1H), 6.47 (d, J=2.2 Hz, 1H), 5.72 (s, 1H), 4.72 (s, 1H), 4.22 (d, J=5.3 Hz, 2H), 3.00 (d, J=7.1 Hz, 3H), 2.92-2.81 (m, 1H), 2.39-2.15 (m, 6H), 2.14 (s, 3H), 2.1 (s, 3H), 2.05-1.95 (m, 2H), 1.89-1.69 (m, 4H), 1.65-1.58 (m, 2H), 1.55-1.46 (m, 4H), 1.45-1.37 (m, 2H), 1.26 (s, 2H), 0.82 (t, J=6.9 Hz, 3H)

Example 95: Preparation of the Compound 3-((4,4-difluorocyclohexyl)(ethyl)amino)-N-((4-hydroxymethyl-6-methyl-2-oxo-1,2-dihydropyridin-3-yl)methyl)-2-methyl-5-(trans-3-(piperidin-1-yl)cyclobutoxy)benzamide (95)

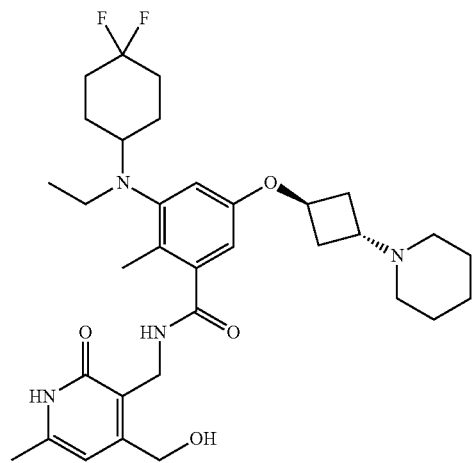

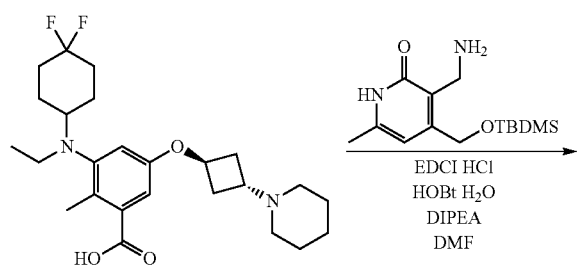

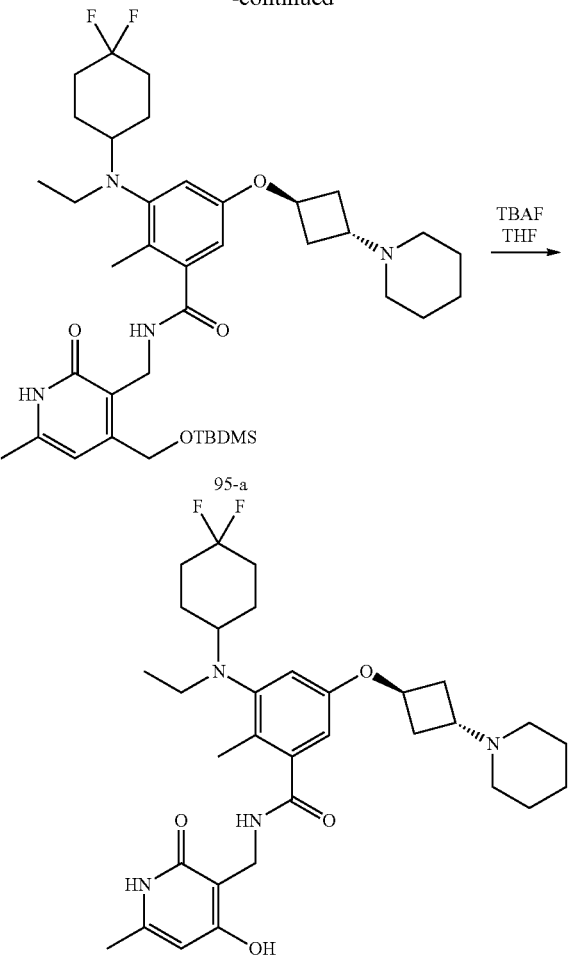

Preparation of Intermediate 95-a 3-((4,4-difluorocyclohexyl)(ethyl)amino)-2-methyl-5-(trans-3-(piperidin-1-yl)cyclobutoxy)benzoic acid (100 mg, 0.22 mmol, 1 eq), 3-aminomethyl-4-((tert-butyldimethylsilyl)oxy) methyl)-6-methylpyridin-2 (1H)-one (100 mg, 0.35 mmol, 1.4 eq) (prepared by methods in literature: J. med. chem. 2016, 59, 1556-1564), EDCI·HCl (59 mg, 0.31 mmol, 1.4 eq), and HOBt·H$_2$O (48 mg, 0.31 mmol, 1.4 eq) were dissolved in N,N-dimethylformamide solution (3 mL), and N,N-diisopropylethylamine (100 mg, 0.77 mmol, 3.5 eq) was added at room temperature. The mixture was stirred overnight at room temperature, and after the reaction was completed, water (30 mL) was added to the system and the mixture was extracted with dichloromethane (20 mL×2). The organic phase was concentrated under reduced pressure to give the crude product N-((4-((tert-butyldimethylsilyl)oxy) methyl-6-methyl-2-oxo-1,2-dihydropyridin-3-yl)methyl)-3-((4,4-difluorocyclohexyl)(ethyl)amino)-2-methyl-5-(trans-3-(piperidin-1-yl)cyclobutoxy)benzamide (100 mg, 63%, brown gum). LCMS: [M+H]$^+$=715.47

Preparation of Compound 95

N-((4-((tert-butyldimethylsilyl)oxy) methyl-6-methyl-2-oxo-1,2-dihydropyridin-3-yl)methyl)-3-((4,4-difluorocyclohexyl)(ethyl)amino)-2-methyl-5-(trans-3-(piperidin-1-yl) cyclobutoxy)benzamide (100 mg, 0.14 mmol, 1 eq) was dissolved in dichloromethane (3 mL), and a 1 mol/L of solution of tetrabutylammonium fluoride in tetrahydrofuran (0.5 mL) was added. The mixture was stirred at room temperature for 1.5 h, and the solvent was removed by concentration. The resulting product was purified by high-pressure reverse phase column chromatography and lyophilized to give 3-((4,4-difluorocyclohexyl)(ethyl)amino)-N-((4-hydroxymethyl-6-methyl-2-oxo-1,2-dihydropyridin-3-yl)methyl)-2-methyl-5-(trans-3-(piperidin-1-yl)cyclobutoxy)benzamide (13.4 mg, 16%, white solid).

m/z (ES+), [M+H]$^+$=601.42; HPLC tR=7.670 min. $^1$H NMR (400 MHz, CD$_3$OD) δ 6.72 (d, J=2.2 Hz, 1H), 6.54 (d, J=2.3 Hz, 1H), 6.46 (s, 1H), 4.80 (s, 2H), 4.78-4.75 (m, 1H), 4.46 (s, 2H), 3.12-3.00 (m, 4H), 2.47-2.36 (m, 5H), 2.34 (s, 3H), 2.33-2.25 (m, 2H), 2.20 (s, 3H), 2.10-1.98 (m, 2H), 1.89-1.80 (m, 2H), 1.80-1.71 (m, 3H), 1.71-1.63 (m, 4H), 1.58-1.51 (m, 2H), 1.33 (s, 2H), 0.90 (t, J=7.0 Hz, 3H)

Experiments on Biological Activities

Example 96: Test on EZH2 Inhibitory Activity

Test Conditions
- EZH2 enzyme complex: 25 ng/uL
- Histone H3 peptide substrate: 4 uM
- SAM: 2 uM
- Reaction time: 300 min Procedures
1. Each compound disclosed herein was diluted with 1×HMT buffer and transferred to a 384-well assay plate at 3 uL per well;
2. The EZH2 enzyme solution was prepared with 1×HMT buffer and transferred to the 384-well assay plate at 2 uL per well;
3. The above assay plate was incubated for 30 min;
4. A mixture solution of SAM and histone H3 peptide substrate at 2-fold concentration was prepared with 4×HMT buffer;
5. 5 uL of the mixture solution of SAM and substrate was added to each well of the assay plate to react at room temperature, and the assay plate was sealed with plastic;
6. After incubation for 5 h, 10 uL of TR-FRET detection buffer containing Tb-labeled antibody and dye-labeled receptor was added to each well of the assay plate;
7. After incubation for 1 h at room temperature, the assay plate was detected;
8. Data were processed using Prizm software.

The results of the experiment are shown in Table 1. A represents IC$_{50}$<0.01 uM, B represents 0.01 uM<IC$_{50}$<0.1 uM, C represents 0.1 uM<IC$_{50}$<1 uM, and D represents IC$_{50}$>1 uM.

TABLE 1

| Compound | IC$_{50}$ of EZH2 inhibition (uM) |
| --- | --- |
| Example 1 | B |
| Example 2 | B |
| Example 3 | B |
| Example 4 | B |
| Example 5 | C |
| Example 6 | B |
| Example 7 | B |
| Example 8 | B |
| Example 9 | C |
| Example 10 | C |
| Example 11 | B |
| Example 12 | B |
| Example 13 | B |
| Example 14 | B |
| Example 15 | B |

TABLE 1-continued

| Compound | IC$_{50}$ of EZH2 inhibition (uM) |
| --- | --- |
| Example 16 | B |
| Example 17 | A |
| Example 18 | B |
| Example 19 | B |
| Example 20 | B |
| Example 21 | B |
| Example 22 | B |
| Example 23 | B |
| Example 24 | A |
| Example 25 | B |
| Example 26 | B |
| Example 27 | A |
| Example 28 | B |
| Example 29 | B |
| Example 30 | B |
| Example 31 | B |
| Example 32 | B |
| Example 33 | C |
| Example 34 | B |
| Example 35 | B |
| Example 36 | B |
| Example 37 | A |
| Example 38 | C |
| Example 39 | C |
| Example 40 | B |
| Example 41 | B |
| Example 42 | B |
| Example 43 | B |
| Example 44 | B |
| Example 45 | B |
| Example 46 | A |
| Example 47 | B |
| Example 48 | B |
| Example 49 | B |
| Example 50 | B |
| Example 51 | C |
| Example 52 | B |
| Example 53 | B |
| Example 54 | B |
| Example 55 | B |
| Example 56 | B |
| Example 57 | D |
| Example 58 | D |
| Example 59 | A |
| Example 61 | D |
| Example 63 | B |
| Example 64 | B |
| Example 71 | B |
| Example 72 | B |
| Example 73 | B |
| Example 74 | B |
| Example 75 | B |
| Example 76 | B |
| Example 77 | B |
| Example 78 | B |
| Example 79 | B |
| Example 80 | B |
| Example 81 | B |
| Example 82 | B |
| Example 83 | B |
| Example 84 | C |
| Example 85 | C |
| Example 89 | B |
| Example 90 | D |

Example 97: Methylated Lysine of Histone-H3 Detection by ELISA

The operations for adherent cells and suspension cells cultured in 96-well plates were slightly different after they had been treated with compound (4-fold dilution 20 uM-0.009 nM, 3 duplicate wells) for 7 days, and the operations are summarized as follows: For adherent cells, after discarding the medium, 75 uL of 1-fold hypotonic lysis buffer (10 mM Tris-HCl, pH 7.5, containing halt protease inhibitor and PMSF with a final concentration of 1 mM) was added; the plate was frozen at −80° C. for at least 1 h or overnight; once the plate was taken away from the −80° C. environment, 120 uL (to a final volume of about 195 uL) of 1-fold hypotonic lysis buffer (containing protease inhibitor) was added, and the plate was thawed at room temperature and shaken for 2 min for mixing; and 8 uL (to a final volume of about 203 uL) of 2.5 M NaCl was added to each well to a final NaCl concentration of 100 mM and then the plate was shaken for an additional 2 min for mixing.

For suspension cells (final volume of medium was 100 uL/well), 25 uL of 5-fold hypotonic lysis buffer (50 mM Tris-HCl, pH 7.5, containing halt protease inhibitor and PMSF with a final concentration of 1 mM) was added, and the plate was frozen at −80° C. for at least 1 h or overnight. Once the plate was taken away from the −80° C. environment, 20 uL of 0.625 M NaCl was added to each well to a final NaCl concentration of about 100 mM, and the mixture was mixed well.

75 uL or 100 uL of sample (with duplicate wells provided) was added to two 96-well ELISA plates (ThermoFisher Scientific; Immulon 4HBX 3885) and the plates were coated with total protein lysate and incubated overnight at 4° C. 50 uL of lysate was retained for protein quantitation if necessary. The sealing of the plates must be ensured. The plates were washed twice with 300 uL of 1×PBST (PBS containing 0.05% Tween 20) per well. Each well was blocked with 300 uL of dilution (PBS+2% BSA+0.05% Tween 20), incubated for 2 h at room temperature, and washed twice with 1×PBST. Primary antibodies were diluted with a dilution solution containing 1% BSA+0.05% Tween 20. 75-100 uL of anti-H3K27Me3 antibody (CST; 9733; 50% glycerol stock, 1:1,000) or anti-total histone-3 antibody (Abcam; ab1791; 50% glycerol stock, 1:10,000) was added to each well. The plates were incubated for 90 min at room temperature or incubated overnight at 4° C. The plates were washed three times with 1×PBST. 75-100 uL of anti-Rb-IgG-HRP secondary antibody (Cell Signaling Technology; 7074) was added per well, 1:2000 diluted secondary antibody for anti-H3K 27Me3 plate and 1:6000 diluted secondary antibody for anti-histone total histone-3 plate. The plates were incubated at room temperature for 90 min. The plate assayed with anti-histone-3 antibody was used to normalize the data for the corresponding plate assayed with anti-H3K 27me3. The plates must be washed at least three times with 1×PBST after primary or secondary antibody incubation. The plates were assayed by adding 75-100 uL of 3,3',5,5'-tetramethylbenzidine substrate (CST or ThermoFisher Scientific; TMBS) per well and incubated away from light for 30 min at 37° C. The reaction was terminated by adding 100 uL of 0.5 M $H_2SO_4$ per well. The absorbance was read at 450 nm. Curve fitting was performed using Graph Pad program.

The results of the experiment are shown in Table 2. A represents $IC_{50}$<0.05 uM, B represents 0.05 uM<$IC_{50}$<0.5 uM, C represents 0.5 uM<$IC_{50}$<1 uM, D represents $IC_{50}$>1 uM, and ND represents not detected.

TABLE 2

| | $IC_{50}$ of cell methylation (uM) | |
|---|---|---|
| Compound | WSU-DLCL2 | Pfeiffer |
| Example 1 | B | A |
| Example 2 | C | B |
| Example 3 | B | A |
| Example 4 | B | A |
| Example 6 | B | A |
| Example 7 | B | A |
| Example 8 | D | B |
| Example 9 | C | C |
| Example 10 | D | C |
| Example 11 | B | B |
| Example 12 | D | B |
| Example 13 | B | A |
| Example 16 | B | A |
| Example 17 | B | A |
| Example 18 | B | A |
| Example 19 | B | A |
| Example 20 | B | A |
| Example 21 | B | A |
| Example 22 | B | A |
| Example 23 | D | A |
| Example 24 | B | A |
| Example 25 | A | A |
| Example 26 | B | A |
| Example 27 | A | A |
| Example 28 | A | A |
| Example 29 | B | A |
| Example 30 | B | A |
| Example 31 | A | A |
| Example 33 | ND | B |
| Example 34 | C | A |
| Example 35 | D | B |
| Example 36 | B | A |
| Example 37 | B | A |
| Example 38 | D | C |
| Example 39 | D | C |
| Example 45 | B | B |
| Example 46 | B | C |
| Example 47 | B | B |
| Example 48 | B | D |
| Example 49 | B | D |
| Example 51 | D | D |
| Example 52 | C | ND |
| Example 53 | B | C |
| Example 55 | B | ND |
| Example 56 | B | B |
| Example 57 | D | D |
| Example 58 | D | D |
| Example 59 | A | B |
| Example 14 | B | A |
| Example 15 | B | A |
| Example 71 | B | A |
| Example 72 | B | A |
| Example 73 | B | B |
| Example 74 | B | A |
| Example 75 | D | A |
| Example 76 | B | A |
| Example 77 | B | A |
| Example 78 | B | A |
| Example 79 | B | A |
| Example 80 | A | ND |
| Example 82 | B | ND |
| Example 83 | D | ND |
| Example 85 | C | ND |

Example 98: Test on EZH2 (Y641F) and EZH2 (Y641N) Inhibitory Activities

Procedures

Compounds at different concentrations were dissolved in 100% DMSO and transferred to test plates, and the final concentration of DMSO was 1%. Enzyme solution and substrate SAM solution were prepared with 1-fold reaction buffer (optimized Tris buffer). 5 uL of enzyme solution was added to the test plate and wells only added with 5 uL of reaction buffer were used as negative control wells. After incubation at room temperature for 15 min, the plate was added with 5 uL of substrate solution per well to initiate the reaction, and then incubated at room temperature for 60 min. 5 uL of receptor solution was added and the plate was incubated away from light at room temperature for 60 min. 10 uL of donor solution was added and the plate was incubated away from light at room temperature for 30 min. The endpoint values were read on the Envision and the $IC_{50}$ was calculated.

Data Calculation

Data were fitted by GraphPad Prism 5 software and inhibition rate was calculated according to equation (1)

Inh %=(Max−Signal)/(Max−Min)×100     (1)

$IC_{50}$ was calculated using equation (2)

Y=Bottom+(Top−Bottom)/(1+10^((Log $IC_{50}$−X)×Hill Slope))

Y: inhibition rate; X: concentration of the compound
The results are shown in the table below:

TABLE 3

| $IC_{50}$ of compound (uM) | EZH2 (Y641N) | EZH2 (Y641F) |
| --- | --- | --- |
| EPZ194 | 0.0034 | 0.002 |
| EPZ195 | 0.0037 | 0.0049 |
| EPZ349 | <0.0005 | <0.0005 |
| Example 45 | 0.0052 | 0.003 |
| Example 68 | 0.001 | 0.0011 |
| Example 87 | 0.0026 | 0.0055 |
| Example 88 | 0.002 | 0.0033 |
| Example 91 | 0.0006 | 0.0007 |
| Example 92 | <0.00051 | <0.00051 |
| Example 93 | <0.00051 | <0.00051 |
| Example 94 | 0.1 | 0.123 |
| Example 95 | 0.0031 | 0.014 |

Note:
control compounds EPZ194, EPZ195, and EPZ349 were compounds numbered 194, 195, and 349 in WO2012142513A1 respectively.

Example 99: Test on EZH2 (wt) Inhibitory Activity

Protocols Compounds at different concentrations were dissolved in 100% DMSO and transferred to test plates, and the final concentration of DMSO was 1%. The enzyme solution and the mixture solution of peptide and [3H]-SAM were prepared with 1-fold reaction buffer. 10 uL of enzyme solution was added to the test plate and wells only added with 10 uL of reaction buffer were used as negative control wells. After incubation at room temperature for 15 min, the plate was added with 10 uL of the mixture solution of peptide and [3H]-SAM per well to initiate the reaction which lasts for 60 min at room temperature. The pre-cooled SAM was added to 1-fold reaction buffer to prepare a stop buffer. The reaction was stopped by adding 10 uL of stop buffer per well. 25 uL of solution was transferred from the reaction plate to Flashplate and incubated at room temperature for at least 1 h. The Flashplate was washed 3 times with $dH_2O$+0.1% Tween-20. The plate was read by Microbeta.

Data Calculation

Data were fitted by GraphPad Prism 5 software and inhibition rate was calculated according to equation (1)

Inh %=(Max−Signal)/(Max−Min)×100     (1)

$IC_{50}$ was calculated using equation (2)

Y=Bottom+(Top−Bottom)/(1+10^((Log $IC_{50}$−X)×Hill Slope))

Y: inhibition rate; X: concentration of the compound
The $IC_{50}$ of each compound is shown in the table below:

TABLE 4

| $IC_{50}$ of compound (uM) | EZH2 (wt) |
| --- | --- |
| EPZ194 | 0.0013 |
| EPZ195 | 0.0019 |
| EPZ349 | <0.0005 |
| Example 45 | 0.0023 |
| Example 68 | 0.0006 |
| Example 87 | 0.0012 |
| Example 88 | 0.0011 |
| Example 91 | 0.0007 |
| Example 92 | 0.00052 |
| Example 93 | <0.00051 |
| Example 94 | 0.145 |
| Example 95 | 0.021 |

Note:
control compounds EPZ194, EPZ195, and EPZ349 were compounds numbered 194, 195, and 349 in WO2012142513A1 respectively.

The results show that the compounds disclosed herein have activities similar to those of the control compounds.

Example 100: Experiment on Cell Proliferation

Experiment on WSU-DLCL2 Cell Proliferation

WSU-DLCL2 cells were plated in a 96-well plate and 100 uL of cells (a density of $1×10^5$ cells/mL) and 50 uL of compound stock at 3-fold concentration was added to each well, and the final volume was 150 uL/well. After 6 days of culturing, on day 7, the cells in the well plate were mixed well by pipetting, and 50 uL of the cell suspension was pipetted to be tested for cell viability using Calcein-AM. 50 uL of the cell suspension was added to a 96-well plate coated by poly-D-Lysine, and then 50 uL of HBSS containing 2 uM Calcein-AM was added to make the final concentration of Calcein-AM 1 uM. After incubation for 10 min at room temperature, the cells were rapidly centrifuged to be deposited on the bottom of the plate. The cells were cultured in the incubator for another 40 min and then the plate was read on Acumen.

The remaining cells were diluted and then plated in a 96-well plate, and 100 uL of cells and 50 uL of a compound at 3-fold concentration were added to each well for further culturing until day 14, and the cell viability was detected as described above. The $IC_{50}$ was calculated.

Experiment on Pfeiffer Cell Proliferation
Pfeiffer Cell Plating 90 uL of cells were added to each well of a 96-well plate at 12000 cells/well, and cell-free culture medium was added to blank control wells. The plate was incubated overnight in an incubator at 37° C., 5% $CO_2$ and 100% relative humidity. The compounds were diluted from highest to lowest concentration gradient with DMSO to make stock solutions at 400-fold and 10-fold concentration. 10 μL of 10× compound working solution was added to the cell culture plate, and the total concentration of the compound was detected from 10 μM, 9 concentration points in total, and 3-fold serial dilution was performed. 10 μL of DMSO-cell culture medium mixture solution was added to the vehicle control wells and blank control wells. The final concentration of DMSO was 0.25%. The plate was put back in the incubator for another 7 days of culturing.

Cell Plating and Compound Retreatment

The cell culture plate cultured for 7 days was taken out of the incubator, and the suspended cells in the 96-well plate were mixed well by pipetting multiple times. 74 uL of fresh cell culture medium was added to a new 96-well plate, and 16 uL of cell suspension was pipetted from the 96-well plate with cells mixed well by pipetting into the new 96-well plate to bring the total volume to 90 uL. Cells in the new 96-well plate were treated with the compound. The new 96-well plate was put back in the incubator for another 7 days of culturing, and then cell viability was detected directly.

Cell Viability Detection

84 μL of cell suspension was taken from the cell culture plate for cell viability detection.

Cell Viability Detection with CellTiter-Glo Luminescence Method

CellTiter-Glo buffer and substrate were thawed and balanced to room temperature. The CellTiter-Glo buffer was added to a bottle of CellTiter-Glo substrate to dissolve the substrate, thereby preparing CellTiter-Glo working solution. The bottle was subjected to slow vortex shaking to completely dissolve the substrate. The cell culture plate was taken out and balanced to room temperature for 30 min. 50 μL of CellTiter-Glo working solution was added to each well. The cell plate was wrapped with aluminum foil to keep out of light. The plate was shaken on an orbital shaker for 2 min to induce cell lysis. The plate was placed at room temperature for 10 min to stabilize the luminescence signals. The luminescence signals were detected on 2104 En Vision plate reader.

Data Analysis

The inhibition rates (IRs) of the detected compounds were calculated according to the following formula: IR (%)=(1−(RLU compound−RLU blank control)/(RLU vehicle control−RLU blank))×100%. Inhibition rates of compounds at different concentrations were calculated in Excel, followed by plotting the inhibition curves and calculating relevant parameters including minimum (%), maximum (%), and absolute $IC_{50}$ using GraphPad Prism software.

The results of WSU-DLCL2 and Pfeiffer cell proliferation are shown in the table below:

TABLE 5

| | $IC_{50}$(uM) | EPZ194 | EPZ195 | EPZ349 | Example 45 | Example 68 | Example 87 | Example 91 |
|---|---|---|---|---|---|---|---|---|
| WSU-DLCL2 | Day 7 | 0.106 | 1.432 | 0.563 | 0.091 | 0.049 | 0.040 | 0.024 |
| | Day 14 | 0.023 | 0.281 | 0.110 | 0.018 | 0.012 | 0.009 | 0.006 |
| Pfeiffer | Day 7 | 0.062 | 0.385 | 0.104 | 0.069 | 0.013 | 0.020 | 0.006 |
| | Day 14 | 0.0110 | 0.127 | 0.033 | 0.0097 | 0.0046 | 0.0043 | 0.002 |

Note:
compounds EPZ194, EPZ195, and EPZ349 were compounds numbered 194, 195, and 349 in WO2012142513A1 respectively.

The results show that example compounds 45, 68, 87 and 91 have about the same or even stronger activity in inhibiting the proliferation of WSU-DLCL2 and Pfeiffer cells compared to the control compounds EPZ194, EPZ915 and EPZ349.

Example 101: In Vivo Pharmacokinetic Properties

Male ICR mice were divided into different groups with 3 mice in each group, and single intravenous injection and single intragastric administration were conducted respectively. The compounds were formulated with 10% DMSO/90% (20% Captisol) to reach an appropriate concentration and then administered intravenously at 5 mg/kg. The compounds were formulated with 0.5% CMC-Na/0.1% Tween 80 (pH=3-4) to reach an appropriate concentration and then administered intragastrically at 250 mg/kg. Blood was taken at 5 min, 15 min, 30 min, 1 h, 2 h, 4 h, 6 h, 8 h and 24 h after administration, and then subjected to EDTA-K2 anticoagulation. The concentration of the compound in the plasma was quantitatively detected by an LC-MS/MS method. Pharmacokinetic parameters of each compound were calculated by Phoenix WinNonlin 7.0 and the results are shown in the table below.

TABLE 6

| Compound | EPZ194 | EPZ195 | EPZ349 | Example 45 | Example 68 | Example 87 | Example 91 | Example 4 |
|---|---|---|---|---|---|---|---|---|
| CL(mL/min/lg) | 59.5 ± 19.1 | 36.5 ± 6.21 | 149 ± 57.0 | 37.0 ± 8.82 | 27.1 ± 5.94 | 31.0 ± 2.82 | 66.9 ± 3.70 | 60.6 ± 19.36 |
| $T_{1/2}$ (h) | 2.13 ± 1.02 | 5.12 ± 0.89 | 2.19 ± 1.32 | 7.44 ± 2.75 | 10.43 ± 8.53 | 5.77 ± 1.51 | 7.72 ± 3.14 | 3.13 ± 3.10 |
| Tmax (h) | 0.83 ± 0.29 | 1.42 ± 1.01 | 0.83 ± 0.29 | 1.00 ± 0.00 | 1.33 ± 0.58 | 0.83 ± 0.29 | 1.67 ± 0.58 | 0.33 ± 0.14 |
| Cmax(ng/mL) | 4059 ± 1830 | 945 ± 283 | 1485 ± 860 | 10500 ± 436 | 9251 ± 181 | 10583 ± 4149 | 9347 ± 1902 | 16519 ± 4626 |
| AUC0-∞ (ng · hr/mL) | 7476 ± 1311 | 3071 ± 486 | 3918 ± 1710 | 50942 ± 11536 | 89464 ± 30471 | 47831 ± 15505 | 51594 ± 19632 | 18778 ± 487 |
| F (%) | 9.91% | 2.64% | 12.8% | 43.5% | 56.5% | 35.4% | 82.3% | 25.1% |

TABLE 6-continued

| Compound | Example 86 | Example 47 | Example 59 | Example 88 | Example 66 | Example 92 | Example 93 |
|---|---|---|---|---|---|---|---|
| CL(mL/min/lg) | 65.5 ± 1.60 | 103 ± 11.9 | 59.1 ± 6.95 | 60.4 ± 0.15 | 53.5 ± 13.44 | 80.84 ± 5.78 | 45.17 ± 4.21 |
| $T_{1/2}$ (h) | 4.19 ± 3.07 | 3.10 ± 1.04 | 6.20 ± 3.83 | 2.26 ± 0.87 | 5.05 ± 0.75 | 2.03 ± 1.14 | 1.30 ± 0.64 |
| Tmax (h) | 0.25 ± 0.00 | 0.67 ± 0.29 | 0.80 ± 0.27 | 0.50 ± 0.00 | 0.42 ± 0.14 | 0.58 ± 0.38 | 0.33 ± 0.14 |
| Cmax(ng/mL) | 21000 ± 8043 | 19600 ± 8052 | 16596 ± 1881.6 | 10153 ± 1450 | 16733 ± 4969 | 9443 ± 1002 | 10727 ± 4116 |
| AUC0-∞ (ng · hr/mL) | 18780 ± 4557 | 48005 ± 19798 | 43042 ± 5182.5 | 23039 ± 4543 | 31164 ± 12897 | 25151 ± 4535 | 21459 ± 2108 |
| F (%) | 29.5% | 118.1% | 60.5% | 33.4% | 38.3% | 48.6% | 23.1% |

Note:
compounds EPZ194, EPZ195, and EPZ349 were compounds numbered 194, 195, and 349 in WO2012142513A1 respectively.

The results show that example compounds 45, 68, 87, 91, 4, 86, 47, 59, 88 and 66 exhibit a significant improvement in pharmacokinetic properties and a significant increase in Cmax and exposure compared to control compounds EPZ194, EPZ195 and EPZ349.

Example 102: In Vivo Efficacy of Compounds in Subcutaneous Xenograft Tumor Model of Human B Lymphocyte Pfeiffer Experiment Method Cell Culturing Human B lymphocyte strain Pfeiffer was cultured in vitro, in a monolayer way, in a RPMI-1640 medium containing 10% fetal bovine serum, 100 U/mL penicillin and 100 μg/mL streptomycin in an incubator at 37° C./5% $CO_2$. Conventional medium refreshment and subculturing were carried out twice a week, and cells in logarithmic growth phase were collected and used for tumor inoculation after being counted.

Experimental Animals

Female SCID Beige mice, aged 6-8 weeks and weighed 18-22 g were used in the experiment. The experiment started after 7-day adaptive feed.

Tumor Cell Inoculation

Each mouse was inoculated subcutaneously with $10 \times 10^6$ Pfeiffer cells in a volume of 0.2 mL in the right side of the neck. The cells were suspended with PBS and matrigel (volume ratio 1:1). After the average tumor volume reached 130 $mm^3$, the mice were divided into groups with 8 mice per group for administration. The administration volume was 10 uL/g and the dose was 100 mg/kg if there's no special labeling ((p.o. administration, QD, continuous administration for 21 days).

Tumor Measurement and Experimental Indices

Animal body weights were measured twice weekly and animal mortality and side effects within each group were recorded based on the number of animals in the group.

The experimental indices were to investigate whether tumor growth was inhibited or delayed or the tumor was cured. Tumor diameters were measured twice weekly using a vernier caliper. The tumor volume was calculated according to the following formula: V=0.5 a×$b^2$, where a and b represent the long diameter and short diameter of the tumor, respectively. The tumor growth inhibitions (TGIs) of the compounds were evaluated by T/C (%). The percentage value of T/C (%) is an index for reflecting the tumor growth inhibition, where T and C represent the average tumor volume of the administration group and the control group, respectively, at a certain day.

The tumor growth inhibition rate was calculated according to the following formula: TGI (%)=(1−(Ti−T0)/(Vi−V0))×100, where Ti is the average tumor volume of a certain administration group on a certain day, T0 is the average tumor volume of the administration group at the start of administration, Vi is the average tumor volume of the vehicle control group on a certain day (same day as Ti) and V0 is the average tumor volume of the vehicle control group at the start of administration.

Statistical Analysis

Relative tumor volumes at each time point for each group were statistically analyzed and differences among groups were assessed based on the data. The statistical method used for testing was one-way ANOVA.

Results of the Experiment

Mortality, morbidity and weight change

Figure 1B:
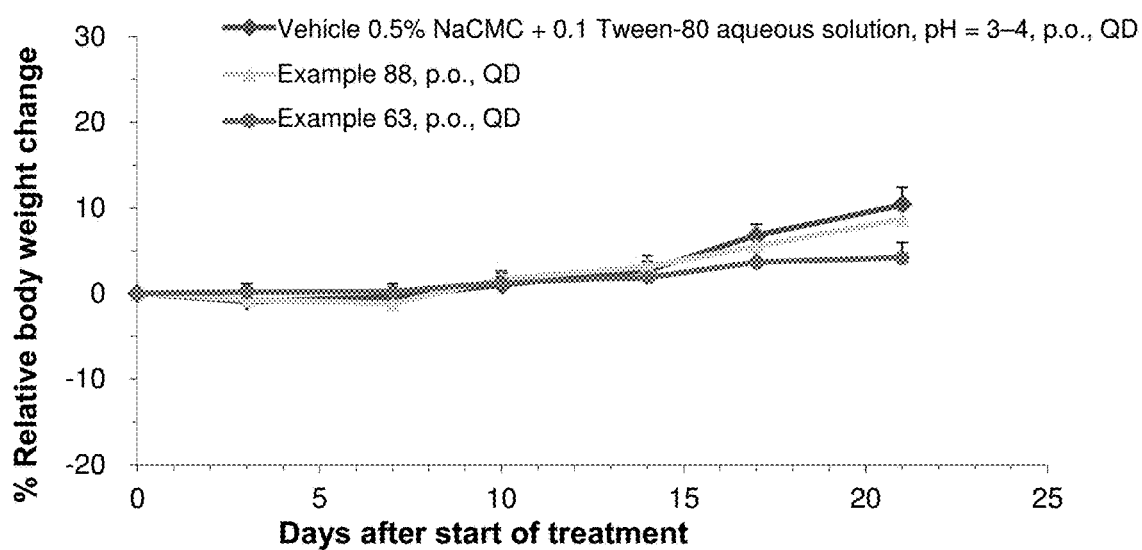
Figure 2A:
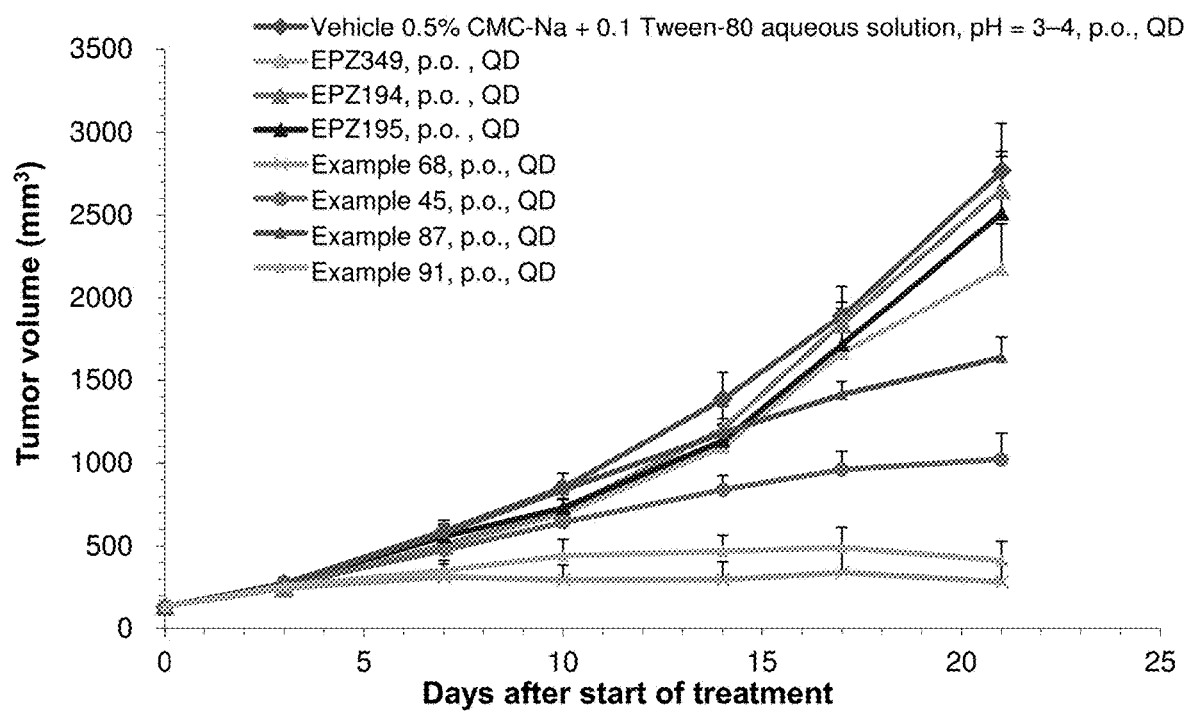
FIGS. 2A and 2B show the tumor growth curves of mice bearing subcutaneous xenograft tumors of human B lymphocyte Pfeiffer after administering a compound of the present invention.
Figure 2B:
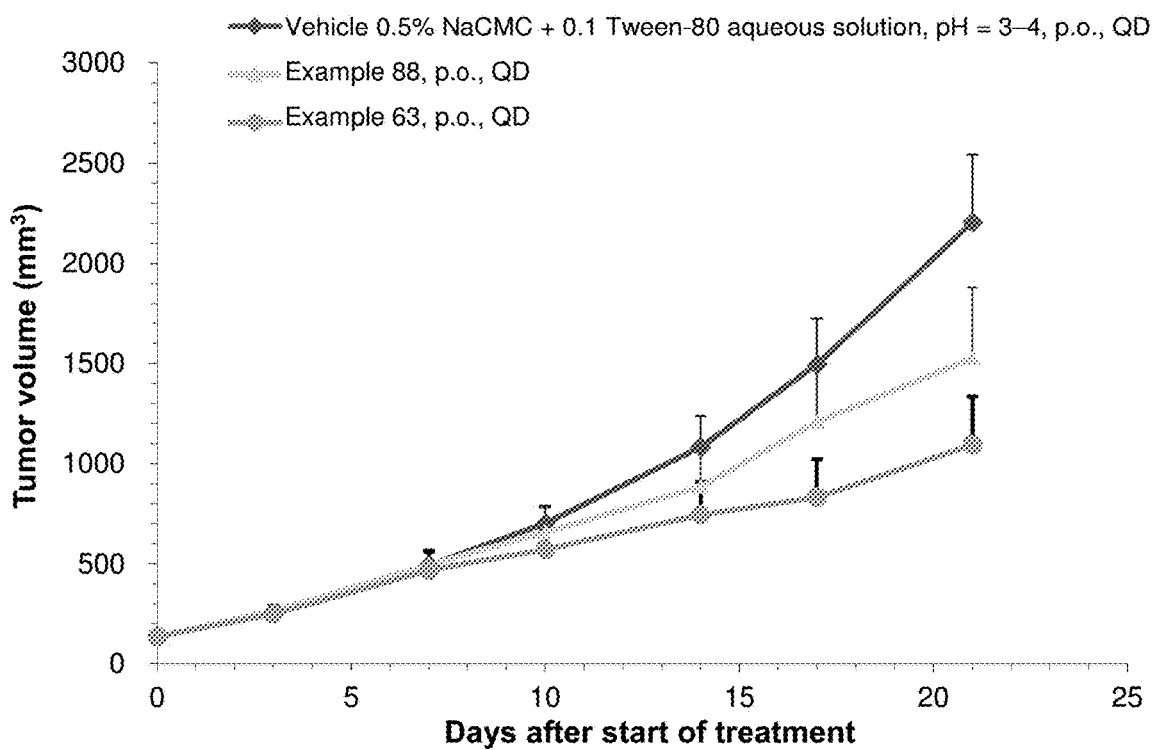

The body weight of the experimental animal was used as a reference index for indirectly measuring the toxicity of the medicament. The relative body weight change is shown in FIGS. 1A and 1B, and the tumor growth curves are shown in FIGS. 2A and 2B.

Calculation of Anti-Tumor Efficacy Evaluation Index TGI

TABLE 7

Evaluation of the anti-tumor efficacy of the test substances on the subcutaneous xenograft tumor model of Pfeiffer cell (calculated based on the tumor volume 21 days after administration)

| Group | TGI[b] (%) | p value[c] |
|---|---|---|
| Vehicle control | — | — |
| EPZ349 | 22.39 | — |
| EPZ194 | 4.27 | — |
| EPZ195 | 9.66 | — |
| Example 68[a] | 94.28 | *** |
| Example 45 | 66.20 | *** |
| Example 87 | 42.84 | *** |
| Example 91[a] | 89.39 | *** |
| Example 88 | 32.83 | — |
| Example 63 | 53.67 | *** |

Note:
[a]administration dose was 50 mg/kg.
[b]tumor growth inhibition was expressed by T/C and TGI (TGI (%) = (1 − (Ti − T0)/(Vi − V0))×100).
[c]p value was calculated based on relative tumor volume and tested by the one-way ANOVA method.

Note:
compounds EPZ194, EPZ195, and EPZ349 were compounds numbered 194, 195, and 349 in WO2012142513A1 respectively.

Results and Discussion

Within 21 days after the start of administration, the animals were in good health with an average decrease in body weight of <5%, and there was no drug discontinuation, indicating good overall tolerability. The tumor volumes of the tumor-bearing mice in the vehicle control group were >2000 mm$^3$. The groups of test drugs Example 68, Example 45 and Example 91 all had a TGI of >60%, showing significant tumor inhibition effect compared with the vehicle control group. Example 87, Example 88 and Example 63 groups, which each had a TGI of >30%, also showed certain tumor inhibition tendency. However, each of the control compounds EPZ349, EPZ194 and EPZ195 groups had a TGI<25%, showing no significant tumor inhibition effect. The results above show that the in vivo tumor-inhibiting effect of Example 68, Example 45, Example 91, and Example 87 is more significant than that of the control compounds.

All cited references are incorporated by reference. Although specific examples of the present invention have been described above, it should be understood by those skilled in the art that various changes, substitutions and alterations can be made to the examples without departing from the spirit and scope of the present invention as defined by the appended claims.

The invention claimed is:

1. A compound of formula (I):

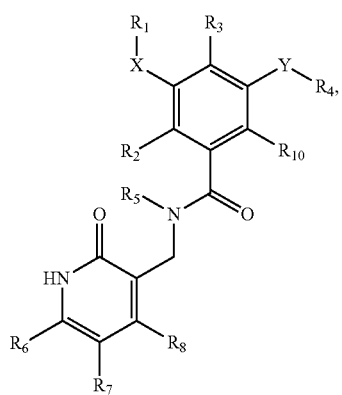

or a stereoisomer, a tautomer and a pharmaceutically acceptable salt thereof, wherein:

X is selected from —O— and NR$_9$, wherein R$_9$ is ethyl;

Y is —O—;

R$_1$ is selected from C$_5$-C$_6$ cycloalkyl and 5-8 membered heterocyclyl, wherein the C$_5$-C$_6$ cycloalkyl or the 5-8 membered heterocyclyl is optionally substituted with one or more groups selected from C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ alkyl-S—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, C$_1$-C$_6$ alkyl-OS(O)$_2$—, halogen, —CN, —OH, and NR$_1$'R$_1$", wherein R$_1$' and R$_1$" are each independently selected from H, C$_1$-C$_6$ alkyl, C$_2$-C$_6$ alkenyl, and C$_2$-C$_6$ alkynyl, wherein the C$_1$-C$_6$ alkyl, the C$_2$-C$_6$ alkenyl, and the C$_2$-C$_6$ alkynyl are optionally substituted with one or more groups selected from C$_1$-C$_6$ alkoxy, halogen, —OH, —CN, —SH, and NH$_2$;

R$_2$ is selected from H, C$_1$-C$_6$ alkyl, and halogen;

R$_3$, and R$_{10}$ are H;

R$_4$ is

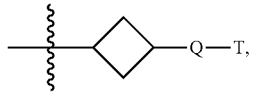

wherein Q is selected from covalent bond and —CH$_2$—, and T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—;

R$_5$ is selected from H and C$_1$-C$_6$ alkyl;

R$_6$ is C$_1$-C$_6$ alkyl;

R$_7$ is H; and

R$_8$ is selected from C$_1$-C$_6$ alkyl, C$_1$-C$_6$ alkoxy, and —OH, wherein the C$_1$-C$_6$ alkyl is optionally substituted with —OH.

2. The compound of claim 1, wherein:

R$_4$ is

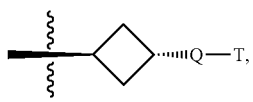

wherein Q is selected from covalent bond and —CH$_2$—, and T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—.

3. The compound of claim 1, wherein:

R$_4$ is

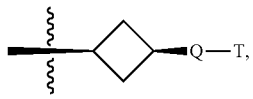

wherein Q is selected from covalent bond and —CH$_2$—, and T is selected from 5-8 membered nitrogen-containing heterocyclyl, wherein the 5-8 membered nitrogen-containing heterocyclyl is optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—.

4. The compound of claim 1, wherein:

the Q is selected from covalent bond and —CH$_2$—, and T is

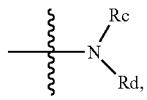

wherein Rc and Rd, together with the nitrogen atom thereto, form a 5-8 membered nitrogen-containing heterocyclyl, wherein the 5-8 membered nitrogen-containing heterocyclyl is optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—.

5. The compound of claim 1, wherein:

T is selected from morpholinyl, piperidinyl, piperazinyl, 8-oxa-3-azabicyclo[3.2.1]octyl, and 6-oxa-3-azabicyclo[3.1.1]heptanyl, wherein the morpholinyl, the piperidinyl, the piperazinyl, the 8-oxa-3-azabicyclo[3.2.1]octanyl, and the 6-oxa-3-azabicyclo[3.1.1]heptanyl are optionally substituted with one or more groups selected from —OH, —SH, —NH$_2$, halogen, —CN, C$_1$-C$_6$ alkyl, C$_2$-C$_6$ alkenyl, C$_2$-C$_6$ alkynyl, C$_1$-C$_6$ alkoxy, C$_1$-C$_6$ alkyl-S—, C$_1$-C$_6$ alkyl-NH—, (C$_1$-C$_6$ alkyl)$_2$N—, C$_1$-C$_6$ alkyl-C(=O)—, C$_1$-C$_6$ alkyl-S(O)—, C$_1$-C$_6$ alkyl-S(O)$_2$—, C$_1$-C$_6$ alkyl-OC(=O)—, and C$_1$-C$_6$ alkyl-OS(O)$_2$—.

6. The compound of claim 1, wherein:

R$_1$ is selected from

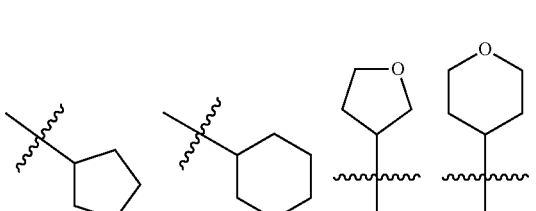

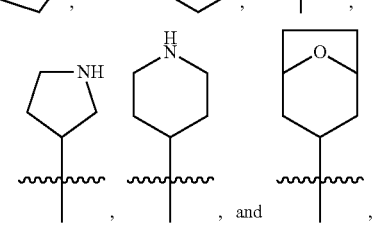

wherein the

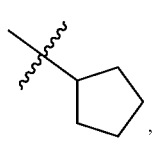

the

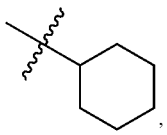 [SMILES: *C1CCCCC1]

the

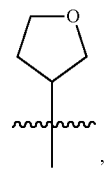

the

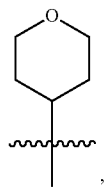

the

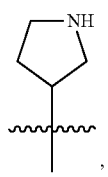

the

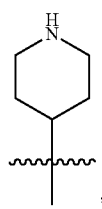

and the

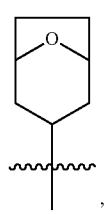

are optionally substituted with one or more groups selected from $C_1$-$C_6$ alkyl, $C_1$-$C_6$ haloalkyl, halogen, —CN, and $NR_1'R_1''$, wherein $R_1'$ and $R_1''$ are each independently selected from H and $C_1$-$C_6$ alkyl, wherein the $C_1$-$C_6$ alkyl is optionally substituted with $C_1$-$C_6$ alkoxy; and Q is selected from covalent bond and —$CH_2$—, and T is selected from

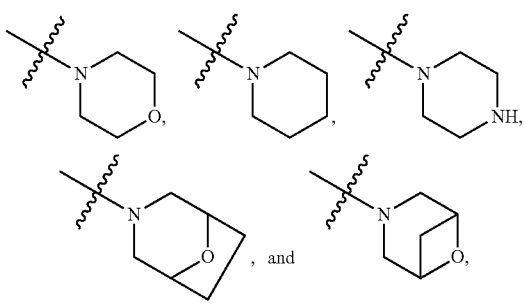

wherein the

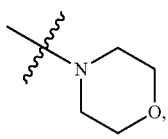 [SMILES: *N1CCOCC1]

the

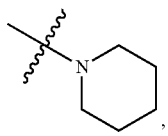

the

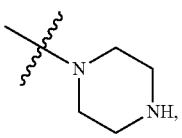 [SMILES: *N1CCNCC1]

the

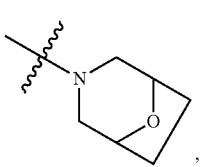 [SMILES: *N1CC2CCC(C1)O2]

and the

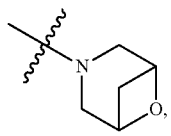

are optionally substituted with one or more groups selected from —OH, —SH, —$NH_2$, halogen, —CN, $C_1$-$C_6$ alkyl, $C_2$-$C_6$ alkenyl, $C_2$-$C_6$ alkynyl, $C_1$-$C_6$ alkoxy, $C_1$-$C_6$ alkyl-S—, $C_1$-$C_6$ alkyl-NH—, ($C_1$-$C_6$ alkyl)$_2$N—, $C_1$-$C_6$ alkyl-C(=O)—, $C_1$-$C_6$ alkyl-S(O)—, $C_1$-$C_6$ alkyl-S(O)$_2$—, $C_1$-$C_6$ alkyl-OC(=O)—, and $C_1$-$C_6$ alkyl-OS(O)$_2$—.

7. The compound of claim 1, wherein:

$R_1$ is selected from

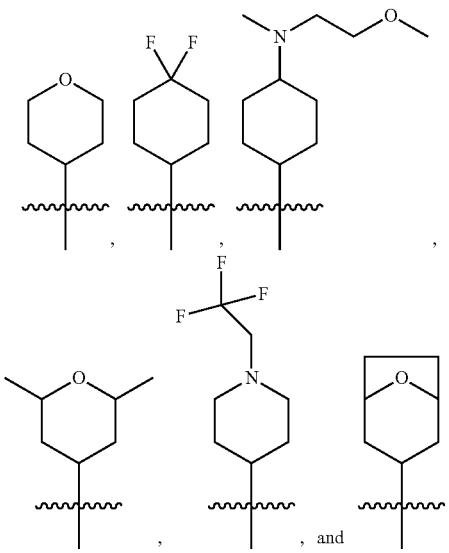

and

Q is selected from covalent bond and —$CH_2$—, and T is selected from:

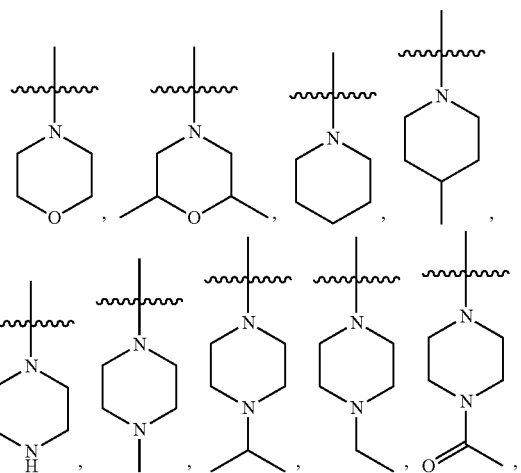

-continued

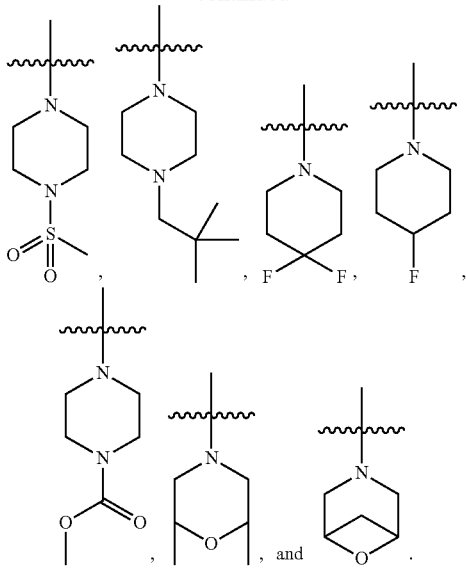

8. The compound of claim 1, comprising a structure selected from:

N-((4,6-dimethyl-2-oxo-1,2-dihydropyridin-3-yl)methyl)-3-(ethyl(tetrahydro-2H-pyran-4-yl)amino)-2-methyl-5-(trans-3-morpholinylcyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(cis-3-(morpholinylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(morpholinylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(3-(morpholinylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(cis-3-(piperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(piperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-5-(cis-3-(4-isopropylpiperazin-1-yl)cyclobutoxy)-2-methylbenzamide, N-((4,6-dimethyl-2-oxo-1,2-dihydropyridin-3-yl)methyl)-3-(ethyl(tetrahydro-2H-pyran-4-yl)amino)-5-(trans-3-(4-isopropylpiperazin-1-yl)cyclobutoxy)-2-methylbenzamide, N-((4,6-dimethyl-2-oxo-1,2-dihydropyridin-3-yl)methyl)-3-(ethyl(tetrahydro-2H-pyran-4-yl)amino)-5-(cis-3-(4-ethylpiperazin-1-yl)cyclobutoxy)-2-methylbenzamide, N-((4,6-dimethyl-2-oxo-1,2-dihydropyridin-3-yl)methyl)-3-(ethyl(tetrahydro-2H-pyran-4-yl)amino)-5-(trans-3-(4-ethylpiperazin-1-yl)cyclobutoxy)-2-methylbenzamide, cis-5-(3-(4-acetylpiperazin-1-yl)cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide, trans-5-(3-(4-acetylpiperazin-1-yl)cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide, N-((4,6-dimethyl-2-oxo-1,2-dihydropyridin-3-yl)methyl)-3-(ethyl(tetrahydro-2H-pyran-4-yl)amino)-2-methyl-5-(cis-3-(4-(methylsulfonyl)piperazin-1-yl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(4-(methylsulfonyl)piperazin-1-yl)cyclobutoxy)benzamide, 2-chloro-N-((4,6-dimethyl-2-oxo-1,2-dihydropyridin-3-yl)methyl)-3-(ethyl(tetrahydro-2H-pyran-4-yl)amino)-5-(trans-3-(morpholinylmethyl)cyclobutoxy)benzamide, 2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)benzamide, N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino)-2-methylbenzamide, N-((4,6-dimethyl-2-oxo-1,2-dihydropyridin-3-yl)methyl)-3-(ethyl(trans-4-((2-methoxyethyl)(methyl)amino)cyclohexyl)amino)-2-methyl-5-(trans-3-(morpholinylmethyl) cyclobutoxy)benzamide, N-((4,6-dimethyl-2-oxo-1,2-dihydropyridin-3-yl)methyl)-5-((cis-3-(cis-2,6-dimethylmorpholinyl)cyclobutoxy)-3-((cis-2,6-dimethyltetrahydro-2H-pyran-4-yl)(ethyl) amino)-2-methylbenzamide, N-((4,6-dimethyl-2-oxo-1,2-dihydropyridin-3-yl)methyl)-3-(ethyl(trans-4-((2-methoxyethyl)(methyl)amino)cyclohexyl)amino)-2-methyl-5-(3-morpholinylcyclobutoxy)benzamide, N-((4,6-dimethyl-2-oxo-1,2-dihydropyridin-3-yl)methyl)-5-(trans-3-(cis-2,6-dimethylmorpholinyl)cyclobutoxy)-3-((cis-2,6-dimethyltetrahydro-2H-pyran-4-yl)(ethyl) amino)-2-methylbenzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(piperidin-1-ylmethyl)cyclobutoxy)benzamide, N-((4,6-dimethyl-2-oxo-1,2-dihydropyridin-3-yl)methyl)-3-(ethyl(tetrahydro-2H-pyran-4-yl)amino)-2-methyl-5-(trans-3-(4-methylpiperidin-1-yl)cyclobutoxy)benzamide, N-((4,6-dimethyl-2-oxo-1,2-dihydropyridin-3-yl)methyl)-5-(((1S,3S)-3-((2S,6R)-2,6-dimethylmorpholinyl)cyclobutoxy)-3-(((2R,4s,6S)-2,6-dimethyltetrahydro-2H-pyran-4-yl) (ethyl)amino)-2-methylbenzamide, N-((4,6-dimethyl-2-oxo-1,2-dihydropyridin-3-yl)methyl)-5-(trans-3-(cis-2,6-dimethylmorpholinyl)cyclobutoxy)-3-((trans-2,6-dimethyltetrahydro-2H-pyran-4-yl)(ethyl) amino)-2-methylbenzamide,
2-chloro-N-((4,6-dimethyl-2-oxo-1,2-dihydropyridin-3-yl)methyl)-3-(ethyl(tetrahydro-2H-pyran-4-yl)amino)-5-(cis-3-morpholinylcyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-morpholinylcyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(cis-3-(piperazin-1-yl)cyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-(piperazin-1-yl)cyclobutoxy)benzamide,
N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)-2-methylbenzamide,
3-((4,4-difluorocyclohexyl)(ethyl)amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide,
N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydrofuran-3-yl)amino)-2-methylbenzamide,
3-((8-oxabicyclo[3.2.1]octan-3-yl)(ethyl)amino)-N-((4,6-dimethyl-2-oxo-1,2-dihydropyridin-3-yl)methyl)-5-(trans-3-(cis-2,6-dimethylmorpholinyl)cyclobutoxy)-2-methylbenzamide,
2-chloro-N-((4,6-dimethyl-2-oxo-1,2-dihydropyridin-3-yl)methyl)-5-(trans-3-(cis-2,6-dimethylmorpholinyl)cyclobutoxy)-3-(ethyl(tetrahydro-2H-pyran-4-yl)amino)benzamide,
5-(trans-3-(8-oxa-3-azabicyclo[3.2.1]octan-3-yl)cyclobutoxy)-2-chloro-N-((4,6-dimethyl-2-oxo-1,2-dihydropyridin-3-yl)methyl)-3-(ethyl(tetrahydro-2H-pyran-4-yl)amino)benzamide,
N-((4,6-dimethyl-2-oxo-1,2-dihydropyridin-3-yl)methyl)-5-(trans-3-(cis-2,6-dimethylmorpholinyl)cyclobutoxy)-3-(ethyl (1-(2,2,2-trifluoroethyl) piperidin-4-yl)amino)-2-methylbenzamide,
N-((4,6-dimethyl-2-oxo-1,2-dihydropyridin-3-yl)methyl)-3-(ethyl(tetrahydro-2H-pyran-4-yl)amino)-N,2-dimethyl-5-(trans-3-morpholinylcyclobutoxy)benzamide,
N-((4,6-dimethyl-2-oxo-1,2-dihydropyridin-3-yl)methyl)-5-(trans-3-(cis-2,6-dimethylmorpholinyl)cyclobutoxy)-3-(ethyl(trans-4-((2-methoxyethyl)(methyl)amino) cyclohexyl)amino)-2-methylbenzamide,
2-chloro-N-((4,6-dimethyl-2-oxo-1,2-dihydropyridin-3-yl)methyl)-5-(trans-3-((cis-2,6-dimethylmorpholinyl)methyl)cyclobutoxy)-3-(ethyl(tetrahydro-2H-pyran-4-yl)amino) benzamide,
5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)-2-methylbenzamide,
5-(trans-3-(6-oxa-3-azabicyclo[3.1.1]heptan-3-yl)cyclobutoxy)-N-((4,6-dimethyl-2-oxo-1,2-dihydropyridin-3-yl)methyl)-3-(ethyl(tetrahydro-2H-pyran-4-yl)amino)benzamide,
N-((4,6-dimethyl-2-oxo-1,2-dihydropyridin-3-yl)methyl)-3-(ethyl(tetrahydro-2H-pyran-4-yl)amino)-2-methyl-5-(cis-3-(4-methylpiperidin-1-yl)cyclobutoxy)benzamide,
N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydro-2H-pyran-4-yl)amino)benzamide,
N-((4,6-dimethyl-2-oxo-1,2-dihydropyridin-3-yl)methyl)-5-(trans-3-(cis-2,6-dimethylmorpholino)cyclobutoxy)-2-methyl-3-((tetrahydrofuran-3-yl)amino)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-(4-methylpiperidin-1-yl)cyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-ylmethyl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-fluoro-5-(trans-3-(morpholinomethyl)cyclobutoxy)benzamide,
N-((4,6-dimethyl-2-oxo-1,2-dihydropyridin-3-yl)methyl)-3-(ethyl(tetrahydro-2H-pyran-4-yl)amino)-2-fluoro-5-(trans-3-morpholinocyclobutoxy)benzamide,
3-((4,4-difluorocyclohexyl)(ethyl)amino)-N-((4,6-dimethyl-2-oxo-1,2-dihydropyridin-3-yl)methyl)-2-methyl-5-(trans-3-morpholinocyclobutoxy)benzamide,
N-((4,6-dimethyl-2-oxo-1,2-dihydropyridin-3-yl)methyl)-3-(ethyl(tetrahydrofuran-3-yl) amino)-2-methyl-5-(trans-3-morpholin-4-ylcyclobutoxy)benzamide,
2-chloro-3-((4,4-difluorocyclohexyl)(ethyl)amino)-N-((4,6-dimethyl-2-oxo-1,2-dihydropyridin-3-yl)methyl)-5-(trans-3-(4-methylpiperidin-1-yl)cyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-(piperidin-1-yl)cyclobutoxy)benzamide,
2-chloro-N-((4,6-dimethyl-2-oxo-1,2-dihydropyridin-3-yl)methyl)-3-(ethyl(tetrahydro-2H-pyran-4-yl)amino)-5-(trans-3-(4,4-difluoropiperidin-1-yl)cyclobutoxy)benzamide,
3-((4,4-difluorocyclohexyl)(ethyl)amino)-N-((4,6-dimethyl-2-oxo-1,2-dihydropyridin-3-yl)methyl)-2-methyl-5-(trans-3-(piperidin-1-yl)cyclobutoxy)benzamide,
2-chloro-3-((4,4-difluorocyclohexyl)(ethyl)amino)-N-((4,6-dimethyl-2-oxo-1,2-dihydropyridin-3-yl)methyl)-5-(trans-3-(cis-2,6-dimethylmorpholino)cyclobutoxy)benzamide,
2-chloro-3-((4,4-difluorocyclohexyl)(ethyl)amino)-N-((4,6-dimethyl-2-oxo-1,2-dihydropyridin-3-yl)methyl)-5-(cis-3-(4-methylpiperidin-1-yl)cyclobutoxy)benzamide,
3-((8-oxabicyclo[3.2.1]octan-3-yl)(ethyl)amino)-N-((4,6-dimethyl-2-oxo-1,2-dihydropyridin-3-yl)methyl-2-methyl-5-(trans-3-morpholinocyclobutoxy)benzamide,
3-((4,4-difluorocyclohexyl)(ethyl)amino)-5-(trans-3-(cis-2,6-dimethylmorpholino) cyclobutoxy)-N-((4-methoxy-6-methyl-2-oxo-1,2-dihydropyridin-3-yl)methyl)-2-methylbenzamide,
3-((8-oxabicyclo[3.2.1]octan-3-yl)(ethyl)amino)-N-((4-methoxy-6-methyl-2-oxo-1,2-dihydropyridin-3-yl)methyl)-5-(trans-3-(cis-2,6-dimethylmorpholino)cyclobutoxy)-2-methylbenzamide, 2-chloro-3-(ethyl(tetrahydro-2H-pyran-4-yl)amino)-N-((4-methoxy-6-methyl-2-oxo-1,2-dihydropyridin-3-yl)methyl)-5-(trans-3-(4-methylpiperazin-1-yl)cyclobutoxy)benzamide, 2-chloro-3-(ethyl(tetrahydro-2H-pyran-4-yl)amino)-N-((4-methyl-2-oxo-6-(trifluoromethyl)-1,2-dihydropyridin-3-yl)methyl)-5-(trans-3-(4-methylpiperazin-1-yl)cyclobutoxy)benzamide, 3-((4,4-difluorocyclohexyl)(ethyl)amino)-N-((4-methoxy-6-methyl-2-oxo-1,2-dihydropyridin-3-yl)methyl)-2-methyl-5-(trans-3-(piperidin-1-yl)cyclobutoxy)benzamide, N-((4,6-dimethyl-2-oxo-1,2-dihydropyridin-3-yl)methyl-3-(ethyl(tetrahydro-2H-pyran-4-yl)amino)-2-methyl-5-(trans-3 (piperidin-1-yl)cyclobutoxy)benzamide, 3-(ethyl(tetrahydro-2H-pyran-4-yl)amino)-N-((4-methoxy-6-methyl-2-oxo-1,2-dihydropyridin-3-yl)methyl)-2-methyl-5-(trans-3-(piperidin-1-yl)cyclobutoxy)benzamide, 3-((4,4-difluorocyclohexyl)(ethyl)amino)-N-((4-hydroxy-6-methyl-2-oxo-1,2-dihydropyridin-3-yl)methyl)-2-methyl-5-(trans-3-(piperidin-1-yl)cyclobutoxy)benzamide, and 3-((4,4-difluorocyclohexyl)(ethyl)amino)-N-((4-hydroxymethyl-6-methyl-2-oxo-1,2-dihydropyridin-3-yl)methyl)-2-methyl-5-(trans-3-(piperidin-1-yl)cyclobutoxy)benzamide.

* * * * *